(12) United States Patent
Trowsdale et al.

(10) Patent No.: US 8,642,728 B2
(45) Date of Patent: Feb. 4, 2014

(54) MODULATION OF THE ACTIVITY AND DIFFERENTIATION OF CELLS EXPRESSING THE OSTEOCLAST-ASSOCIATED RECEPTOR

(75) Inventors: John Trowsdale, Cambridge (GB); Alexander Barrow, Cambridge (GB); Richard Farndale, Cambridge (GB)

(73) Assignee: Cambridge Enterprise Ltd., Cambridge (GB)

( * ) Notice: Subject to any disclaimer, the term of this patent is extended or adjusted under 35 U.S.C. 154(b) by 0 days.

(21) Appl. No.: 13/122,637

(22) PCT Filed: Oct. 6, 2009

(86) PCT No.: PCT/GB2009/002382
§ 371 (c)(1),
(2), (4) Date: Oct. 6, 2011

(87) PCT Pub. No.: WO2010/040998
PCT Pub. Date: Apr. 15, 2010

(65) Prior Publication Data
US 2012/0028903 A1     Feb. 2, 2012

(51) Int. Cl.
*A61K 38/39* (2006.01)
*A61K 38/17* (2006.01)
*C07K 14/78* (2006.01)

(52) U.S. Cl.
USPC ......... 530/324; 514/16.7; 514/17.2; 514/21.3

(58) Field of Classification Search
None
See application file for complete search history.

(56) References Cited

U.S. PATENT DOCUMENTS

2005/0186283 A1*  8/2005  Geistlich et al. .............. 424/488

FOREIGN PATENT DOCUMENTS

| WO | WO 02/20718 | 3/2002 |
|---|---|---|
| WO | WO 2007/017671 | 2/2007 |
| WO | WO 2007/146401 | * 12/2007 |
| WO | WO 2008/048607 | 4/2008 |
| WO | WO 2008/048607 A2 | * 4/2008 |

OTHER PUBLICATIONS

Raynal et al., J. Biol. Chem., 2006, vol. 281(7):3821-3831.*

* cited by examiner

*Primary Examiner* — Xiaozhen Xie
(74) *Attorney, Agent, or Firm* — Michael J. Brignati

(57) ABSTRACT

This invention relates to the finding that collagen peptides bind to the osteoclast-associated receptor (OSCAR) and stimulate the activation and/or differentiation of OSCAR expressing cells, such as osteoclasts and osteoclast precursor cells. Collagen peptides are described which may be useful in the modulation of the differentiation and/or activation of OSCAR expressing cells, for example in the treatment of bone defects and disorders characterized by altered differentiation and/or activation of OS-CAR expressing cells.

7 Claims, 13 Drawing Sheets

(GPP)$_{10}$
SEQ ID NO:2

GPOGPAGFOGAO
SEQ ID NO:5

(GPP)$_{10}$
SEQ ID NO:2

GPOGPAGFOGAO
SEQ ID NO:5 hOSCAR-CD3ζ NFAT-GFP reporter cells mOSCAR-CD3ζ NFAT-GFP reporter cells

MODULATION OF THE ACTIVITY AND DIFFERENTIATION OF CELLS EXPRESSING THE OSTEOCLAST-ASSOCIATED RECEPTOR

CROSS-REFERENCE TO RELATED APPLICATIONS

This application is a 35 U.S.C. §371 national stage application of International Patent Application PCT/GB2009/002382 (published as WO 2010/040998 A1), filed Oct. 6, 2009, which claimed priority of British Patent Application 0818273.5, filed Oct. 6, 2008.

FIELD OF INVENTION

This invention relates to collagen peptides, in particular collagen peptides which modulate the activity and/or differentiation of osteoclast-associated receptor (OSCAR) expressing cells, such as osteoclasts.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Apr. 4, 2011. The Sequence Listing is made up of 164 kilobytes, and the information contained in the attached "SEQUENCE LISTING" is identical to the information in the specification as originally filed. No new matter is added.

BACKGROUND OF INVENTION

Bone is a dynamic tissue which is constantly being remodelled by osteoblasts and osteoclasts. New bone is built by osteoblasts and old bone resorbed by osteoclasts, and the development and homeostasis of skeletal systems depends on this balance between bone formation and resorption.

Insufficient osteoclast activity leads to insufficient amounts of old bone being resorbed and can cause osteopetrosis, a disease in which the bones of the sufferer become denser and harden. Similarly, increased osteoclast activity leads to increased amounts of old bone being resorbed and can also cause disease. Diseases which are associated with increased osteoclast activity include primary and secondary bone cancer, as well as osteoporosis and rheumatoid arthritis.

Osteoclasts express the osteoclast-associated receptor (OSCAR) on their cell surface (WO0220718). This receptor can modulate osteoclast activity (WO0220718) and is also expressed on osteoclast precursor cells (Kim et al., 2002) as well as on the surface of monocytes, macrophages, dendritic cells and neutrophils in humans (Merck, E. et al, 2004; Merck, E. et al, 2005; Merck, E. et al, 2006)).

SUMMARY OF INVENTION

The present inventors have discovered that collagen is the ligand of the osteoclast-associated receptor (OSCAR), and that OSCAR binding by collagen peptides stimulates the activation and/or differentiation of OSCAR expressing cells. In particular, the present inventors have shown that collagen peptides can stimulate OSCAR-mediated signalling, as well as differentiation of osteoclast precursor cells.

An aspect of the invention provides a collagen peptide which modulates the differentiation and/or activation of an osteoclast-associated receptor (OSCAR) expressing cell.

Another aspect of the invention provides a collagen peptide for use in a method of treating a bone defect or a disorder characterized by altered differentiation and/or activation of an osteoclast-associated receptor (OSCAR) expressing cell.

Another aspect of the invention provides a method of treating a bone defect or a disorder characterized by altered differentiation and/or activation of an osteoclast-associated receptor (OSCAR) expressing cell comprising;
administering a collagen peptide to an individual in need thereof.

Another aspect of the invention provides the use of a collagen peptide in the manufacture of a medicament for the treatment of a bone defect or a disorder characterized by altered differentiation and/or activation of an osteoclast-associated receptor (OSCAR) expressing cell.

Another aspect of the invention provides methods of screening for modulators of differentiation and/or activation of an osteoclast-associated receptor (OSCAR) expressing cell comprising;
contacting an OSCAR expressing cell with a collagen peptide in the presence or absence of a test compound.

Another aspect of the invention relates to the use of a collagen peptide for modulating differentiation and/or activation of an osteoclast-associated receptor (OSCAR) expressing cell in vitro.

Another aspect of the invention provides an in vitro method of modulating differentiation and/or activation of an osteoclast-associated receptor (OSCAR) expressing cell comprising;
contacting an osteoclast-associated receptor (OSCAR) expressing cell with a collagen peptide.

Another aspect of the invention provides a pharmaceutical composition comprising a collagen peptide and a pharmaceutical agent capable of altering activation and/or differentiation of an osteoclast-associated receptor (OSCAR) expressing cell, and a pharmaceutically acceptable excipient.

Other aspects of the invention provide a culture vessel for culturing an osteoclast-associated receptor (OSCAR) expressing cell comprising a surface coated with a collagen peptide, and a kit comprising such a culture vessel for example for use in characterizing an osteoclast-associated receptor (OSCAR) expressing cell. Such culture vessels and kits may be used e.g. in a screen for modulators of osteoclast-associated receptor (OSCAR) expressing cell differentiation and/or activity.

BRIEF DESCRIPTION OF FIGURES AND TABLES

FIG. 1. shows that OSCAR is a receptor for collagen. Fc-fusion proteins of human Ig-like receptors OSCAR (OSCAR-Fc), OSCAR-like transcript-2 (OLT2-Fc), TREM-like transcript-1 (TLT1-Fc), and Siglec-15 (Siglec15-Fc) were used in ELISA to assess binding to plates coated with: type I-V collagens (x-axis), Ethicon, Devro-Ethicon (Dev-Eth), Horm and ProColl CS are all different preparations of collagen-1, the integrin $\alpha 2\beta 1$ homotrimeric peptide ligand 'GFOGER' (SEQ ID NO:1) and monomeric collagen-related peptide (mCRP) were also included. Bovine serum albumin (BSA) was used as negative control protein coat (x-axis). An Fc-fusion of the platelet collagen receptor, glycoprotein VI (gpVI), was used as a positive control and purified human IgG (IgG) was used as negative control. Primary Fc-fusions were detected using HRP-conjugated rabbit anti-human secondary antibodies and absorption at an optical density of 450 nm (OD) was recorded (y-axis).

FIG. 2 shows that OSCAR-Fc does not bind appreciably to other α2β1 integrin peptide ligands. The triple-helical peptide, (GPP)$_{10}$, was used as negative control for triple-helical peptides bound by N- and C-terminal (GPP)$_5$ repeats to form the triple-helical peptide structures FIG. 3 shows that OSCAR-Fc does not bind appreciably to the extracellular matrix proteins, vitronectin and fibronectin. The triple-helical peptide, (GPP)$_{10}$, was used as negative control for triple-helical peptides bound by N- and C-terminal (GPP)$_5$ repeats to form the triple-helical peptide structures FIG. 4 shows that anti-human OSCAR mAb 11.1CN5 blocks OSCAR-Fc binding to type-I, -II and -III collagen, whereas an isotype control mAb has no effect.

Figure 7:
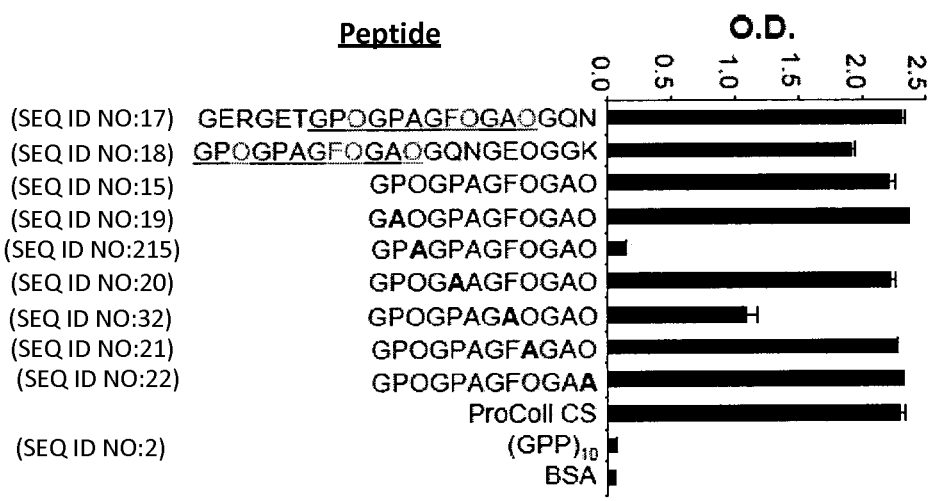

FIG. 7 shows the results of an ELISA assay of OSCAR-Fc binding to plates coated with III-36 homotrimeric peptide derivatives conforming to, the corresponding halves of III-36 containing a putative OSCAR binding sequence conforming to the predicted motif (underlined), a trimmed peptide containing only this motif, and peptides in which an alanine scan (bold) run was run through the trimmed sequence along non-helix breaking residues (Gxx').

Figure 8:
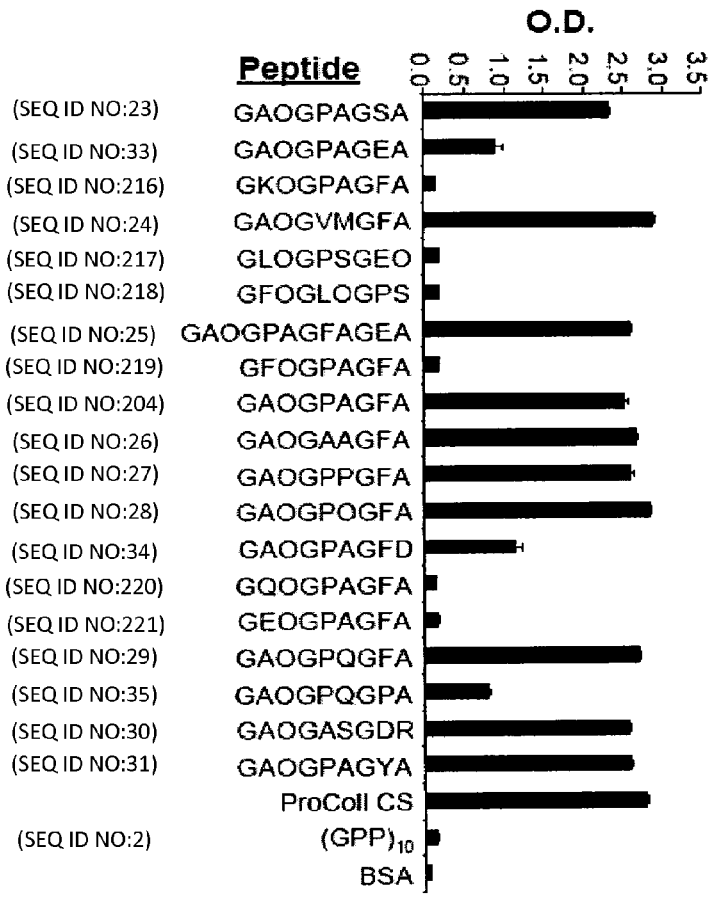

FIG. 8 shows the effect of various amino-acid substitutions on human OSCAR-Fc binding activity by ELISA.

Figure 9:
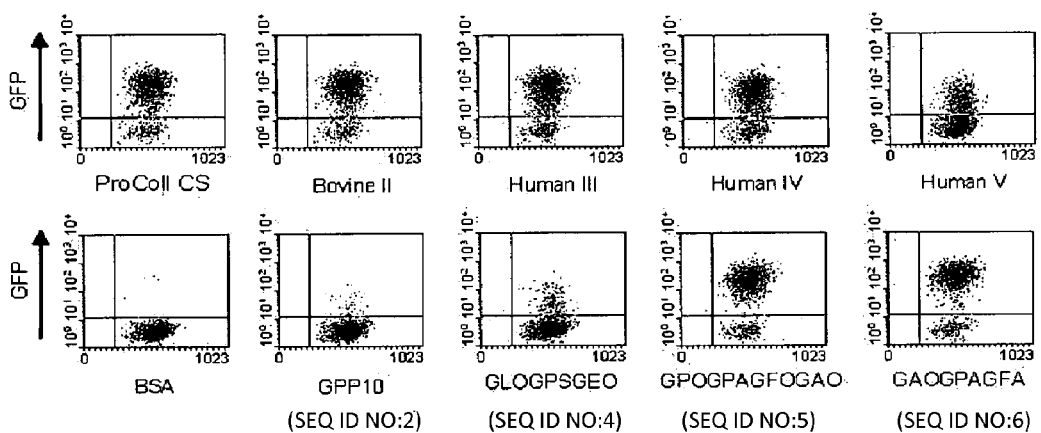

FIG. 9 shows dotplots showing GFP expression (y-axis) versus forward scatter (x-axis) of a human OSCAR-CD3ξ NFAT-GFP reporter cell-line in response to overnight culture on tissue culture plates coated with BSA, collagens type-I (ProColl CS), -II (Bovine II), -III (Human III), -IV (Human IV) and -V (Human V) and peptides, (GPP)$_{10}$(SEQ ID NO:2) , and the N- and C-terminal bound (GPP)$_5$ (SEQ ID NO:3) triple-helical peptides: (GPP)$_5$- 'GLOGPSGEO' -(GPP)$_5$ (SEQ ID NO:4), (GPP)$_5$ -GPOGPAGFOGAO(GPP)$_5$ (SEQ ID NO:5) or (GPP)$_5$-GAOGPAGFA(GPP)$_5$ (SEQ ID NO:6) . 2000 events are displayed in each dotplot.

Figure 10:
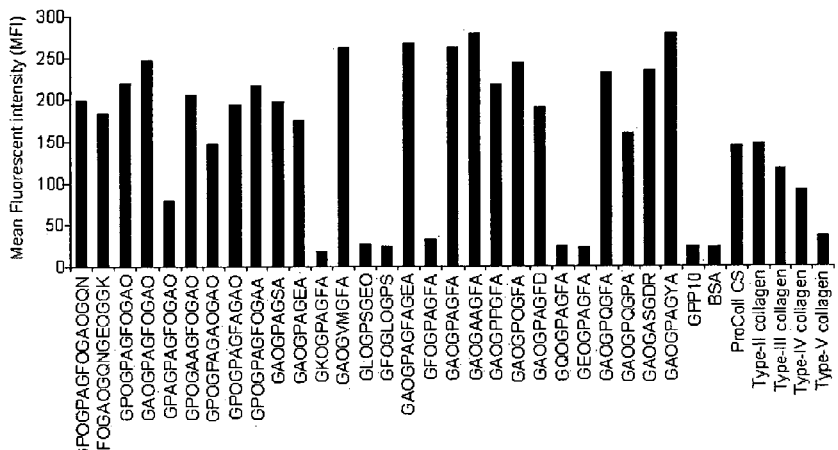

FIG. 10 shows a graph of mean fluorescent intensity (MFI) of GFP expression of the hOSCAR-CD3ξ NFAT-GFP reporter cell-line in response to Ala-scan and amino acid substitution peptides coated on tissue culture plates. Peptide sequences shown were all bound by N- and C-terminal (GPP)$_5$ repeats.

Figure 11:
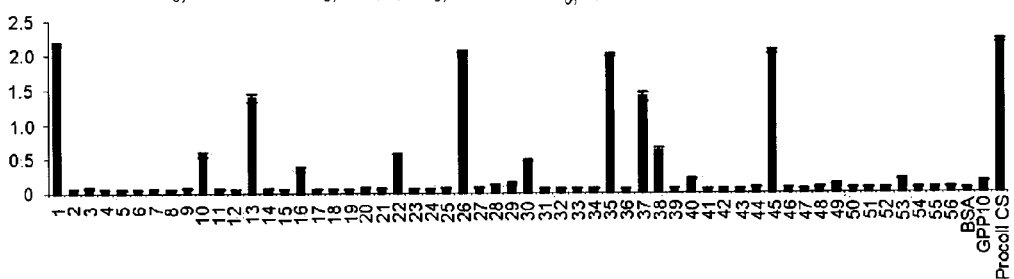

FIG. 11 shows the identification of a human OSCAR collagen binding motif. Human OSCAR-Fc was used to screen a plate-bound overlapping type-II triple-helical collagen peptide library (type-II collagen toolkit) by ELISA. Peptide sequences (peptides #1-56) from this library are shown in Table 1.

Figure 12:
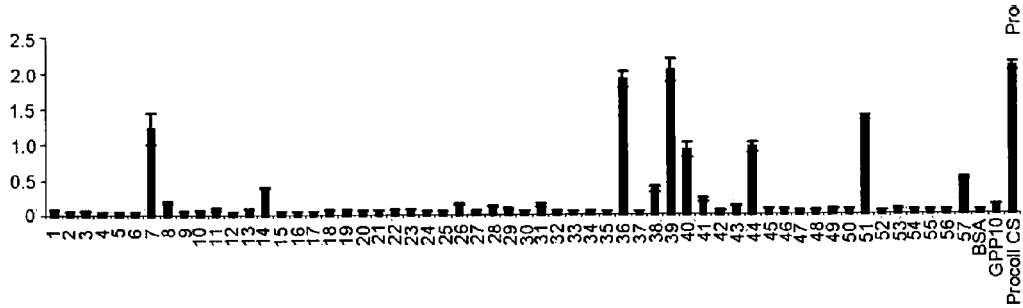

FIG. 12 shows the identification of a human OSCAR collagen binding motif. Human OSCAR-Fc was used to screen a plate-bound overlapping type-III triple-helical collagen peptide libraries (type-III collagen toolkit) by ELISA. Peptide sequences (peptides #1-57) from this library are shown in Table 2.

Figure 13:
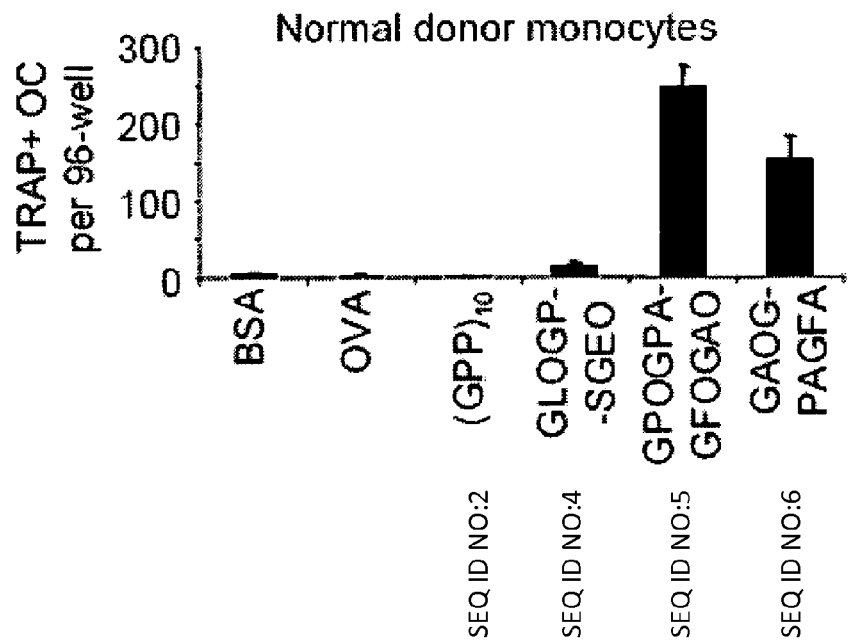

FIG. 13 shows that tissue culture plates coated with OSCAR-binding collagen peptides promote osteoclastogenesis. Human peripheral blood monocytes were cultured in flat-bottomed 96-well tissue plates coated with either BSA; control ovalbumin peptide (OVA), (GPP)$_{10}$ (SEQ ID NO:2), (GPP)$_5$-GLOGPSGEO- (GPP)$_5$ (SEQ ID NO:4), (GPP)$_5$-GPOGPAGFOGAO- (GPP)$_5$ (SEQ ID NO:5) or (GPP)$_5$-GAOGPAGFA-(GPP)$_5$ (SEQ ID NO:6) (x-axis). Cultures were stained for Tartrate-resistant acid phosphatase (TRAP) (dark red/purple staining) Giant multinuclear TRAP+osteoclasts (OC) were enumerated after 7 days culture with 100ng/ml recombinant RANK-L and 30ng/ml M-CSF (y-axis). The OSCAR-binding collagen peptides (GPP)$_5$-GPOGPAGFOGAO -(GPP)$_5$ (SEQ ID NO:5) and (GPP)$_5$-GAOGPAGFA-(GPP)$_5$ (SEQ ID NO:6) enhance osteoclastogenesis, whereas BSA, OVA, (GPP)$_{10}$(SEQ ID NO:2) and (GPP)$_5$-GLOGPSGEO-(GPP)$_5$ (SEQ ID NO:4), which bind human OSCAR-Fe, did not.

Figure 14:
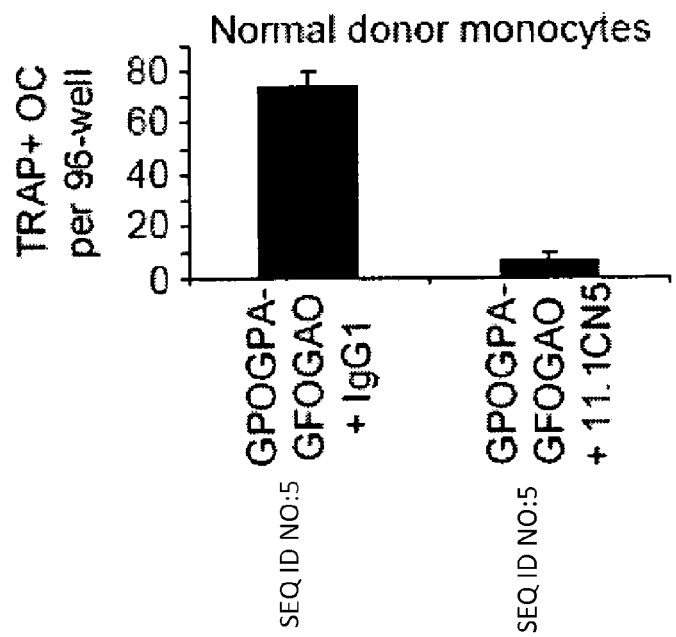

FIG. 14 shows the number of TRAP+giant multinuclear cells enumerated after 7 days in culture (y-axis) of human peripheral blood monocytes in flat-bottomed 96-well tissue plates coated with (GPP)$_5$-GPOGPAGFOGAO-(GPP)$_5$ (SEQ ID NO:5) in the presence of 2.5 µg/ml of either the mouse anti-human OSCAR mAb 11.1CN5 or the anti-MHC class I mAb (x-axis).

Figure 15:
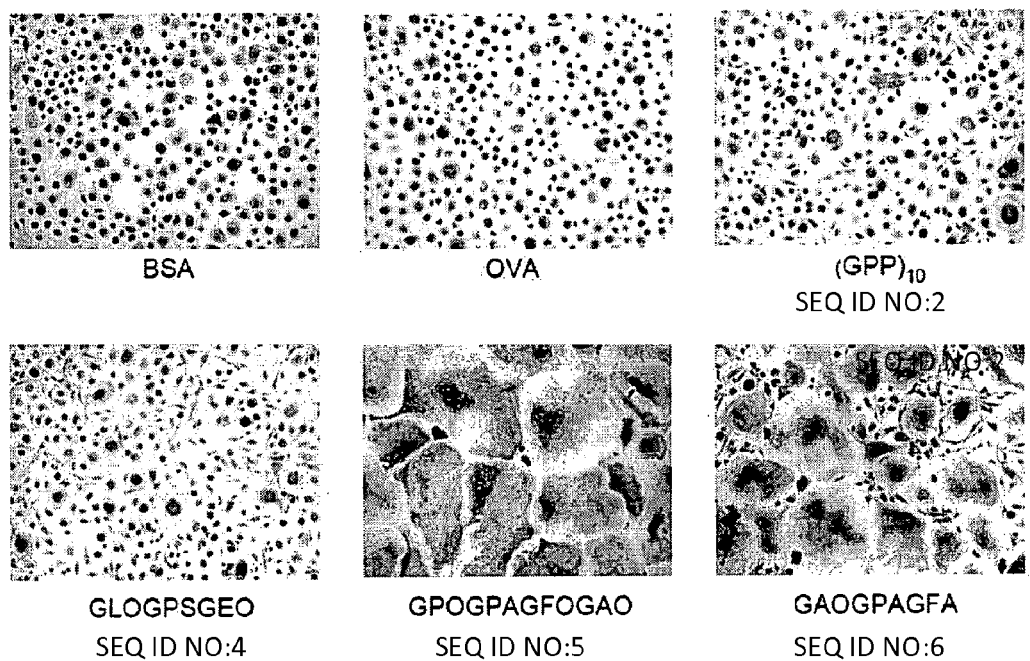

FIG. 15 shows examples of the TRAP+cells generated under the culture conditions of FIG. 14. After 7d days culture, giant TRAP+multinuclear cells are present at higher cell densities in plates coated with either (GPP)$_5$-GPOGPAGFOGAO-(GPP)$_5$ (SEQ ID NO:5) or (GPP)$_5$-GAOGPAGFA -(GPP)$_5$(SEQ ID NO:6), but BSA, OVA or (GPP)$_5$-GLOGPSGEO-(GPP)$_5$(SEQ ID NO:4).

Figure 16:
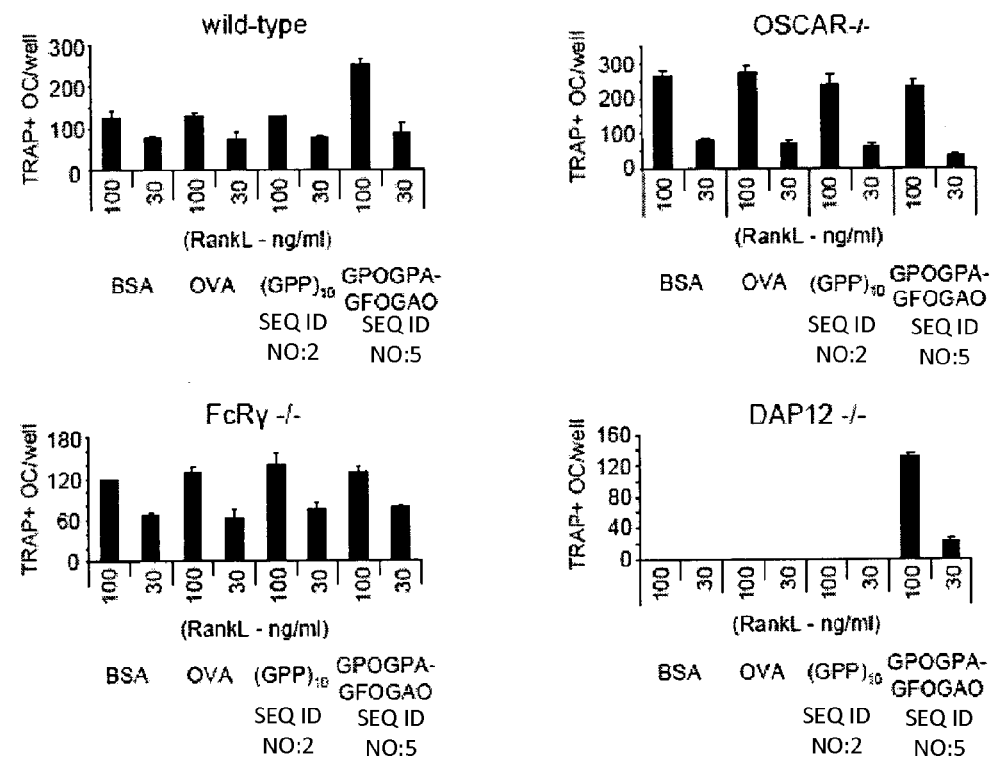

FIG. 16 shows that BMM from wild-type C57BL/6 mice also exhibit enhanced osteoclastogenesis (y-axis) in tissue culture plates coated with (GPP)$_5$-GPOGPAGFOGAO-(GPP)$_5$ (SEQ ID NO:5), but not BSA, OVA or (GPP)$_{10}$ (SEQ ID NO:2) (x-axis) (upper left panel). BMM from either OSCAR -deficient (OSCAR-/-) (upper right) or FcRγ-deficient (FcRγ-/-) (lower left) mice do not show enhanced osteoclastogenesis in plates coated with (GPP)$_5$-GPOGPAGFOGAO-(GPP)$_5$ (SEQ ID NO:5), compared to BSA, OVA or (GPP)$_{10}$. The in vitro osteoclastogeneic defect of DAP12-deficient (DAP12-/-) BMM (lower right) is rescued upon culture in plates coated with (GPP)$_5$-GPOGPAGFOGAO-(GPP)$_5$ (SEQ ID NO:5), but not BSA, OVA or (GPP)$_{10}$ (SEQ ID NO:2) at concentrations of either 30ng/mlRANK-L +10ng/ml M-CSF or 100ng/mlRANK-L +10ng/ml M -CSF).

Figure 17A:
Figure 17A:
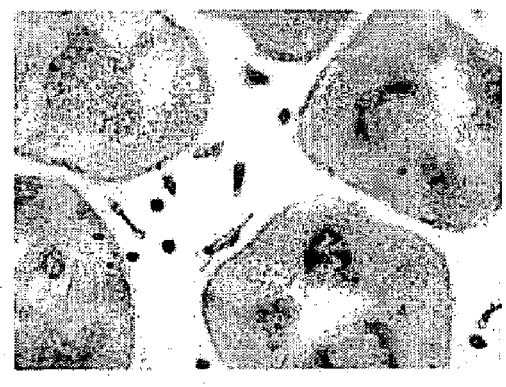
Figure 17B:
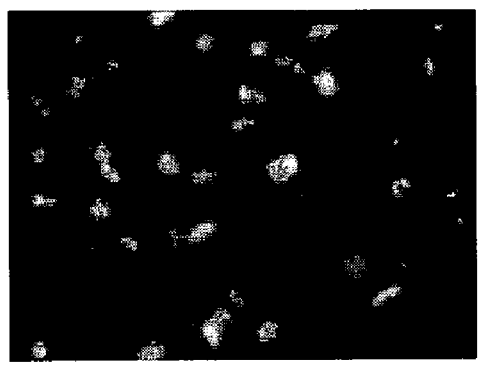
Figure 17B:
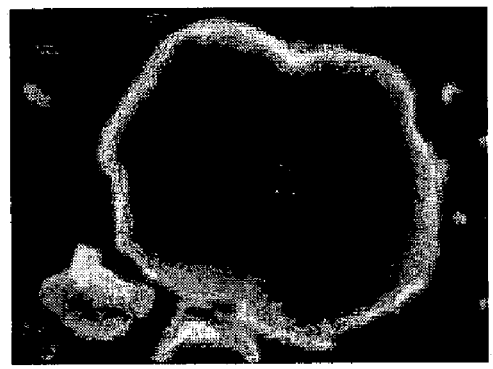

FIG. 17A shows examples of the rescued DAP12-/- giant TRAP+(red/purple histological stain) multinucleated cells formed on plates coated with (GPP)$_5$-GPOGPAGFOGAO-(GPP)$_5$ (SEQ ID NO:5) (x20 objective) . FIG. 17B shows examples of TRAP+mononuclear DAP12-/- cells cultured on (GPP)$_{10}$-coated plates (SEQ ID NO:2) for comparison. By immunofluorescence, the rescued DAP12-/- giant multinuclear (DAPI, blue staining) formed actin rings as revealed by Phalloidin-Alex 488 (green staining)

Figure 18:
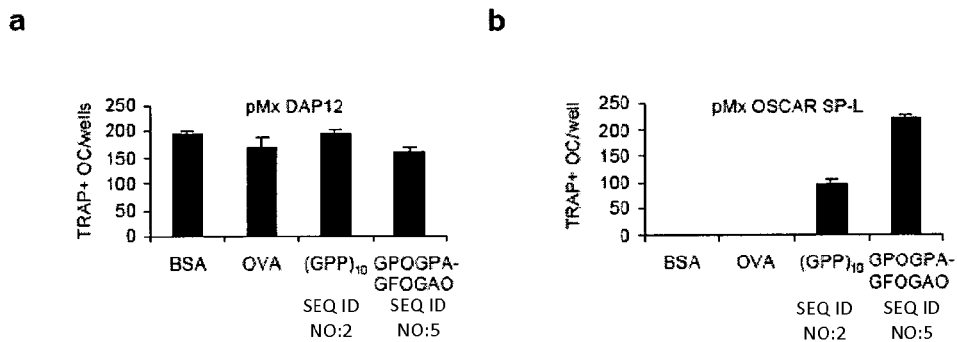

FIG. 18 shows OSCAR ligand-binding rescues the osteoclastogenesis defect in DAP12- and TREM2-deficient Nasu-Hakola patients. (RH panel) Retroviral transduction of DAP12 rescues the in vitro osteoclastogeneic defect of OSCAR-/-DAP12-/- BMM (y-axis) in plates coated with either BSA, OVA, (GPP)$_{10}$ (SEQ ID NO:2) or (GPP)$_5$-GPOGPAGFOGAO-(GPP)$_5$ (SEQ ID NO:5), whereas (LH panel) Retroviral transduction of OSCAR (long signal peptide isoform (SP-L) rescues the in vitro osteoclastogenic defect of OSCAR-/-DAP12-/- BMM only in plates coated with (GPP)$_5$-GPOGPAGFOGAO-(GPP)$_5$ (SEQ ID NO:5), but not plates coated with BSA or OVA. (GPP)$_{10}$-coated plates (SEQ ID NO:2) also developed giant TRAP+multinucleated cells to lesser extent.

Figure 19:
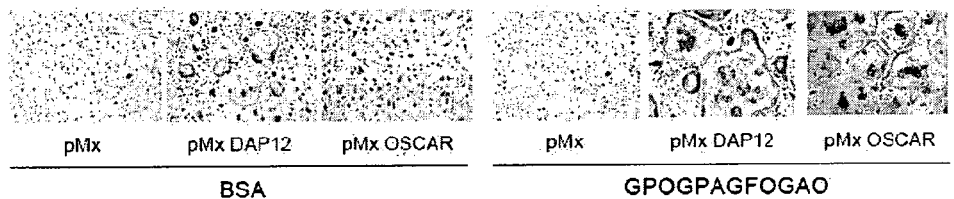

FIG. 19 shows examples of TRAP+(red/purple histological stain) cells formed on plates coated with either BSA or (GPP)$_5$-GPOGPAGFOGAO-(GPP)$_5$ (SEQ ID NO:5) upon.

Figure 20:
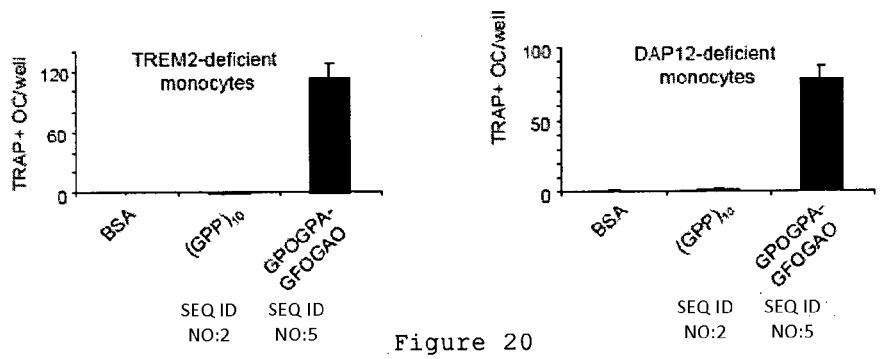

FIG. 20 shows the in vitro osteoclastogeneic defect of human peripheral blood monocytes from TREM2-deficient (LHS) or DAP12-deificient Nasu-Hakola patients (RHS) is rescued upon culture on tissue culture plates coated with (GPP)$_5$-GPOGPAGFOGAO-(GPP)$_5$ (SEQ ID NO:5), but not plates coated with BSA or (GPP)$_{10}$ (SEQ ID NO:2).

Figure 21:
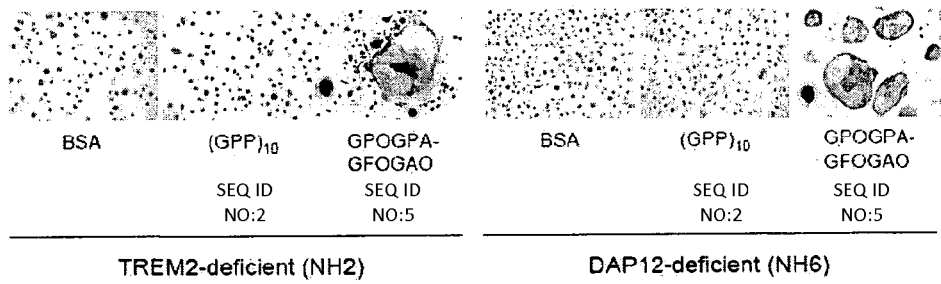

FIG. 21 shows examples of the giant TRAP+multinuclear cells rescued from TREM2-deficient (NH2) or DAP12-deficient (NH2) Nasu-Hakola patients in wells coated with (GPP)$_5$-GPOGPAGFOGAO-(GPP)$_5$ (SEQ ID NO:5) but not BSA or (GPP)$_{10}$(SEQ ID NO:2) (x20 objective)

Figure 22:
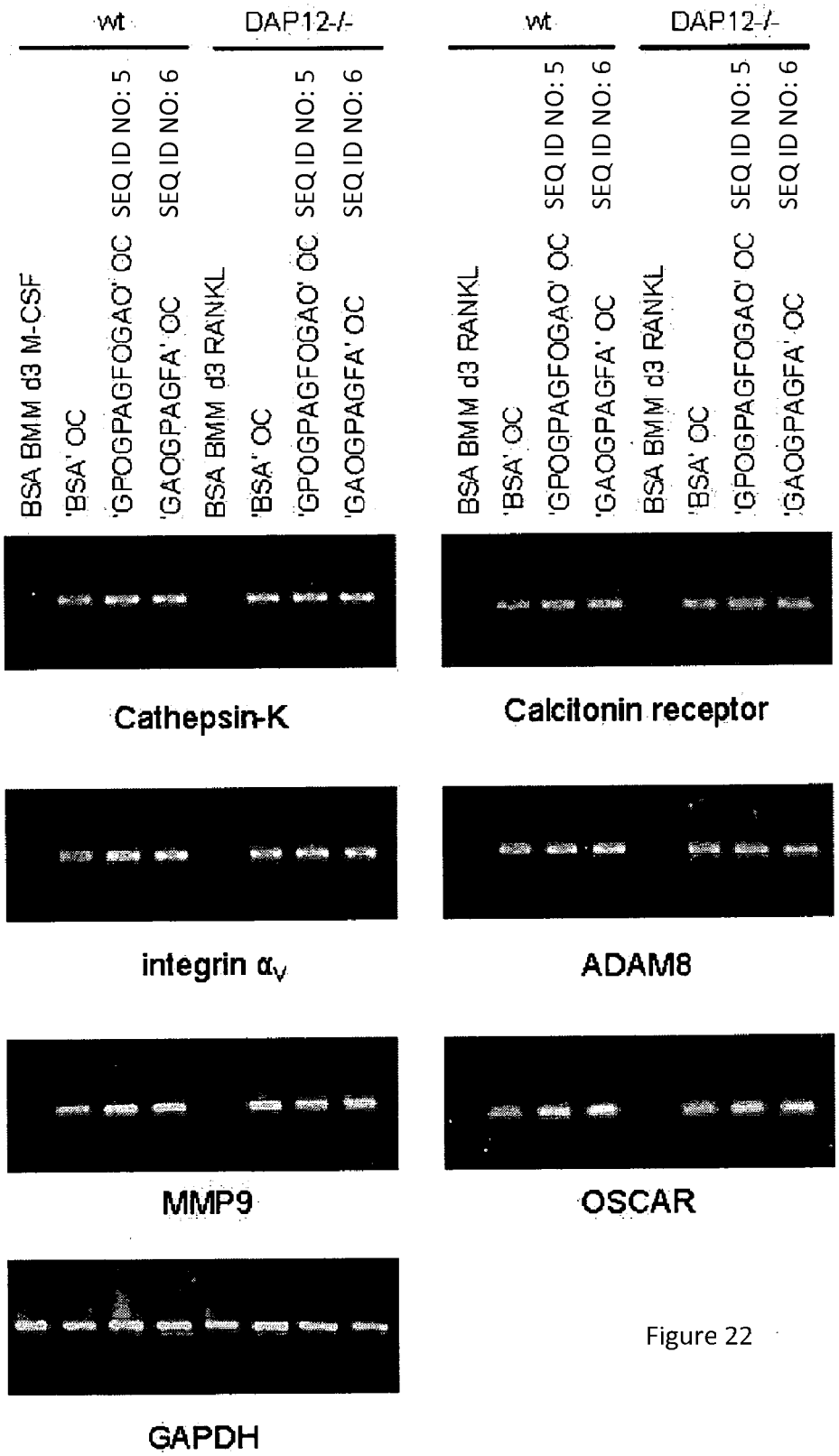

FIG. 22 shows expression of osteoclast-specific genes from DAP12- deficient BMM osteoclasts cultured on BSA-, (GPP)$_5$-GPOGPAGFOGAO-(GPP)$_5$(SEQ ID NO:5), and (GPP)$_5$-GAOGPAGFA -(GPP)$_5$-coated (SEQ ID NO:6) tissue culture plates by RT-PCR. BMM from DAP12-deficient mice were cultured on BSA-, (GPP)$_5$-GPOGPAGFOGAO-(GPP)$_5$(SEQ ID NO:5) and (GPP)$_5$-GAOGPAGFA-(GPP)$_5$ (SEQ ID NO:6)-coated tissue culture plates.

Figure 23:
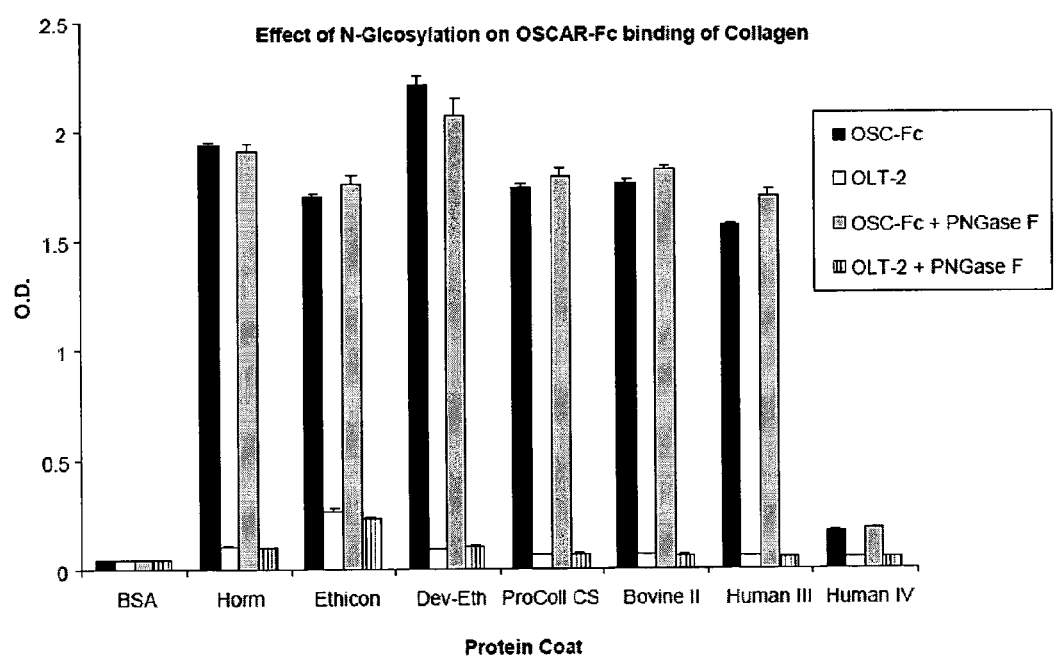

FIG. 23 shows the effect of N-glycosylation on OSCAR-Fc binding to collagen. Fc-fusions of human Ig-like receptors OSCAR (OSC-Fc), OSCAR-like transcript-2 (OLT2) were used in ELISA to assess binding to collagens type I-V in the presence and absence of Peptide-N-glycosidase F (PNGase F), which releases asparagine-linked (N-linked) oligosaccharides from glycoproteins and glycopeptides. Ethicon, Devro-Ethicon (Dev-Eth), Horm and ProColl CS are all different preparations of type-I collagen. Binding to bovine serum albumin (BSA) was used as a negative control. Black bars indicate OSCAR-Fc binding in the absence, and light grey bars in the presence, of PNGase F. Open bars indicate OSCAR-like transcript-2 binding in the absence, and dark grey bars in the presence, of PNGase F.

Figure 24:
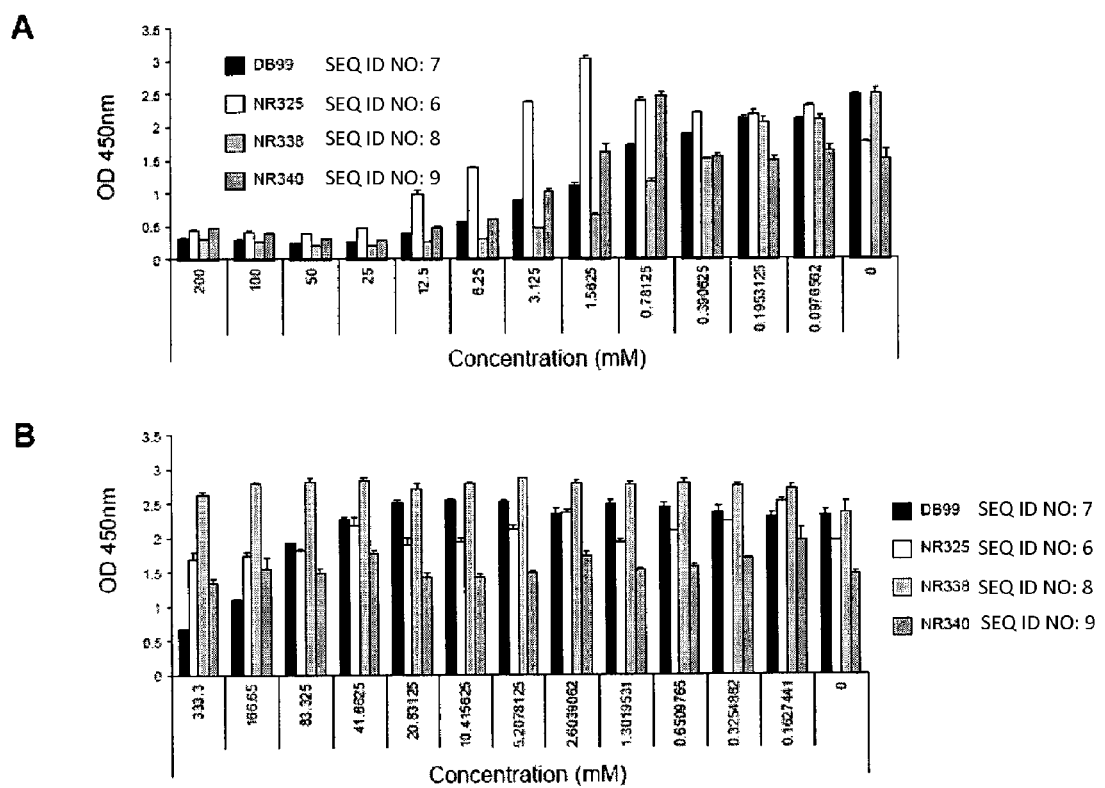

FIG. 24 shows that soluble triple-helical OSCAR-binding peptides block human OSCAR-Fc binding to immobilised triple-helical peptides. (A) The triple-helical peptides: DB99, (GPP)$_5$ -GAOGPAGSA-(GPP)$_5$(SEQ ID NO:7); NR325, (GPP)$_5$-GAOGPAGFA-(GPP)$_5$ (SEQ ID NO:6); NR338, (GPP)$_5$-GAOGASGOR-(GPP)$_5$ (SEQ ID NO:8) and NR340, (GPP)$_5$-GAOGPAGYA -(GPP)$_5$(SEQ ID NO:9) were immobilised on 96-well Nunc immunosorp plates. Human OSCAR-Fc (2.5µ/ml) was incubated for 30 mins at room temperature with soluble versions of each peptide at the indicated doubling concentration range (0-200µM, x-axis). The OSCAR-Fc:peptide complexes were then assayed for binding to their respective immobilised peptides by solid-phase assay and absorbance at an optical density at 450nM recorded (y-axis). Whilst each peptide clearly has a separate affinity for OSCAR-Fc, the increasing concentrations of each soluble peptide, clearly inhibit binding of OSCAR-Fc to the immobilised version of the same peptide. (B) Control experiment for soluble peptide blocking activity on human OSCAR-Fc. The triple-helical peptides: DB99, (GPP)$_5$-GAOGPAGSA-(GPP)$_5$ (SEQ ID NO:7); NR325, (GPP)$_5$-GAOGPAGFA-(GPP)$_5$ (SEQ ID NO:6); NR338, (GPP)$_5$-GAOGASGOR-(GPP)$_5$ (SEQ ID NO:8) and NR340, (GPP)$_5$ -GAOGPAGYA-(GPP)$_5$ (SEQ ID NO:9) were immobilised on 96-well Nunc immunosorp plates.

Figure 25:
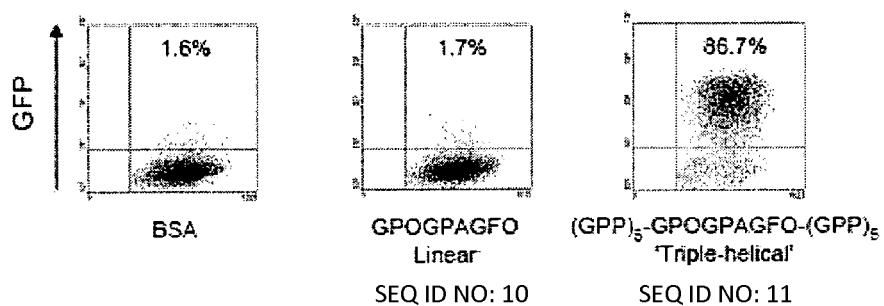
Figure 25:
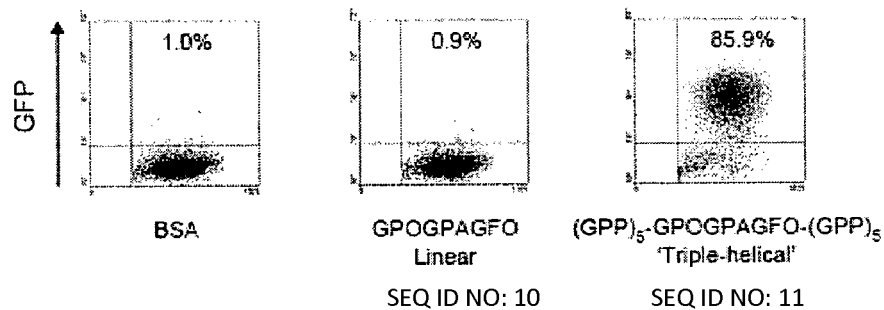

FIG. 25 shows dotplots (10,000 events) displaying the responses of the human (h) and murine (m) OSCAR-CD3Zeta NFAT-GFP reporter cell-lines to: immobilised BSA; a linear peptide containing the minimal OSCAR-binding sequence 'GPOGPAGFO'(SEQ ID NO:10) and a triple-helical peptide designed to the minimal OSCAR-binding sequence'(GPP)$_5$-GPOGPAGFO-(GPP)$_5$'(SEQ ID NO:11). GFP-expression, y-axis; Forward-scatter, x-axis.

Table 1 shows the sequences of the overlapping homotrimeric type-II collagen peptide library (collagen II toolkit) which encompasses the entire type-II collagen sequence. The mass of the peptides in Daltons (Da) is also shown.

Table 2 shows the sequences of the overlapping homotrimeric type-III collagen peptide library (collagen III toolkit) (SEQ ID NO:40) which encompasses the entire type-II collagen sequence. The mass of the peptides in Daltons (Da) is also shown.

Table 3 shows the amino acid sequences of the III-36 peptide derivatives, including their mass in Daltons (Da).

Table 4 shows an alignment of the homotrimeric collagen-based peptides sequences which bound the strongest to OSCAR-Fc Table 5 shows a prediction of the putative OSCAR binding site.

DETAILED DESCRIPTION OF EMBODIMENTS

This invention relates to collagen peptides which interact with the osteoclast-associated receptor (OSCAR) and modulate differentiation and/or activation of OSCAR expressing cells Osteoclast-associated receptor (OSCAR) is a cell-surface receptor which is expressed on the surface of mammalian osteoclasts and other cell types. Examples of osteoclast-associated receptors include the human osteoclast-associated receptor (GeneID: 126014; reference amino acid sequence AAH35023.1 GI: 23273932), the mouse osteoclast-associated receptor (GeneID: 232790; reference amino acid sequence AAI37777.1 GI: 187950779) and the rat osteoclast-associated receptor (GeneID: 292537; sequence herein).

Suitable osteoclast-associated receptors (OSCAR) may comprise the amino acid sequence of a reference sequence identified above or an allelic variant thereof. The amino acid sequence of an allelic variant may, for example, have at least 90%, at least 95%, at least 96%, at least 97%, at least 98%, or at least 99% sequence identity to the reference sequence.

Osteoclast-associated receptors may be identified using standard methods in the art, such as immunological techniques. Antibodies specific for OSCAR are commercially available and include, for example, mAb 11.1CN5 (Beckman coulter), mAb 18D440.1 (Abcam), goat OSCAR polyclonal Ab (Novus Biologicals); and OSCAR (M-17), (N-16) and (D-19) goat polyclonal IgGs (Santa Cruz Biotechnology).

Osteoclast-associated receptor (OSCAR) may be expressed by mammalian cells, for example, human cells or murine cells, such as mouse and rat cells. Cells which express osteoclast-associated receptor (OSCAR) include osteoclasts, osteoclast precursors, monocytes, macrophages, dendritic cells and neutrophils.

Any collagen peptide which forms hetero- or homo-trimers under appropriate conditions and binds OSCAR may be used as described herein.

For example, collagen peptide suitable for use as described herein may comprise the amino acid sequence;

GX$_1$OGX$_2$X$_3$GX$_4$X$_5$,       (SEQ ID NO: 12)

wherein O is a hydroxyproline residue and
X$_1$ is independently any non-polar amino acid,
X$_2$ is independently P, A, or V,
X$_3$ is independently any amino acid, $X_4$ is independently F, S, D, Y, A or E;

$X_5$ is independently any amino acid.

In some embodiments, a collagen peptide suitable for use as described herein may comprise the amino acid sequence;

GX₁OGX₂X₃GX₄X₅,                 (SEQ ID NO: 12)

wherein O is a hydroxyproline residue and $X_1$ is independently A, P or G, preferably P or A, more preferably A, $X_2$ is independently P, A, or V, more preferably P or A $X_3$ is independently A, M, P, O, Q, or S; more preferably A or S $X_4$ is independently F, S, D, Y, A or E; preferably F, S, D or Y, most preferably F, $X_5$ is independently O, A, R or Q, preferably O.

In some preferred embodiments, a collagen peptide may comprise the amino acid sequence GX₁OGPX₃GFO (SEQ ID NO:13), wherein $X_1$ and $X_3$ are as defined above.

For example, a collagen peptide may comprise the amino acid sequence GX₁OGPX₃GFOGX₆O (SEQ ID NO:14), wherein $X_1$ and $X_3$ are as defined above and $X_6$ is independently A, P, L or A.

A collagen peptide may comprise an amino acid sequence having at least 50%, at least 60%, at least 70%, at least 90% or at least 95% sequence identity to a sequence selected from the group of GPOGPAGFOGAO (SEQ ID NO:15), GAOGPAGFA (SEQ ID NO:16), GERGETGPOGPAGFOGAOGQN (SEQ ID NO:17), GPOGPAGFOGAOGQNGEOGGK (SEQ ID NO:18), GAOGPAGFOGAO (SEQ ID NO:19), GPOGAAGFOGAO (SEQ ID NO:20), GPOGPAGFAGAO (SEQ ID NO:21), GPOGPAGFOGAA (SEQ ID NO:22), GAOGPAGSA (SEQ ID NO:23), GAOGVMGFA (SEQ ID NO:24), GAOGPAGFAGEA (SEQ ID NO:25), GAOGAAGFA (SEQ ID NO:26), GAOGPPGFA (SEQ ID NO:27), GAOGPOGFA (SEQ ID NO:28), GAOGPQGFA (SEQ ID NO:29), GAOGASGDR (SEQ ID NO:30), GAOGPAGYA (SEQ ID NO:31), GPOGPAGAOGAO (SEQ ID NO:32), GAOGPAGEA (SEQ ID NO:33), GAOGPAGFD (SEQ ID NO:34), and GAOGPQGPA (SEQ ID NO:35), wherein O is a hydroxyproline residue.

Sequence identity is commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (McGinnis S et al. (2004) 32:W20-W25; Altschul et al. (1990)), FASTA (which uses the method of Pearson and Lipman 1988), or the Smith-Waterman algorithm (Smith and Waterman 1981), or the TBLASTN program, of Altschul et al. (1990) supra, generally employing default parameters. In particular, the psi-Blast algorithm may be used (Altschul et al. 1997). BLAST algorithms are available via an interface at the NCBI website (Johnson et al 2008). Sequence identity and similarity may also be determined using Genomequest™ software (Gene-IT, Worcester Mass. USA).

Sequence comparisons are preferably made over the full-length of the relevant sequence described herein.

A suitable collagen peptide may comprise an amino acid sequence selected from the group of: GPOGPAGFOGAO (SEQ ID NO:15), GAOGPAGFA (SEQ ID NO:16), GERGETGPOGPAGFOGAOGQN (SEQ ID NO:17), GPOG-PAGFOGAOGQNGEOGGK (SEQ ID NO:18), GAOGPAGFOGAO (SEQ ID NO:19), GPOGAAGFOGAO (SEQ ID NO:20), GPOGPAGFAGAO (SEQ ID NO:21), GPOGPAGFOGAA (SEQ ID NO:22), GAOGPAGSA (SEQ ID NO:23), GAOGVMGFA (SEQ ID NO:24), GAOGPAGFAGEA (SEQ ID NO:25), GAOGAAGFA (SEQ ID NO:26), GAOGPPGFA (SEQ ID NO:27), GAOGPOGFA (SEQ ID NO:28), GAOGPQGFA (SEQ ID NO:29), GAOGASGDR (SEQ ID NO:30), GAOGPAGYA (SEQ ID NO:31), GPOGPAGAOGAO (SEQ ID NO:32), GAOGPAGEA (SEQ ID NO:33), GAOGPAGFD (SEQ ID NO:34), and GAOGPQGPA (SEQ ID NO:35), wherein O is a hydroxyproline residue.

In some embodiments, a collagen peptide may comprise two or more repeats of a collagen sequence set out above.

A collagen peptide may be at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acids in length.

Alternatively, a collagen peptide may be up to 10, up to 15, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200 or up to 300 amino acids in length.

The sequence of a collagen peptide may be a naturally occurring collagen sequence (i.e. a collagen sequence which exists in nature), for example a collagen sequence found in collagen-I, -II or -III, or a non-naturally occurring collagen sequence (i.e. an artificial collagen sequence which does not exist in nature).

A collagen peptide may be comprised within a non-naturally occurring peptide and polypeptide fusions, for example wherein the collagen peptide is fused to one or more sequences which are not naturally fused to the peptide. Sequences which are not naturally fused to the collagen peptide may include artificial collagen sequences, non-collagen sequences or additional copies of the peptide sequence itself.

In some embodiments, one or more heterologous amino acids may be joined or fused to the N- and/or C-terminal end of a collagen peptide set out herein and a polypeptide or peptide may comprise a peptide as described above linked or fused to one or more heterologous amino acids.

A heterologous amino acid sequence is an amino acid sequence which is not naturally found in collagens, e.g. a non-collagen sequence. Heterologous amino acid sequences include artificial sequences, i.e. sequences not found in nature.

A heterologous amino acid sequence is a sequence not occurring in any natural collagen (e.g. collagen-I, -II or -III) joined by a peptide bond without intervening amino acids to a peptide described herein, that is to say usually a chain of amino acids which is not found naturally joined to a collagen peptide described herein at the position of fusion in the peptide. Usually, where heterologous amino acids are fused to the N or C terminal of the collagen peptide, the whole contiguous sequence of amino acids does not occur within collagen.

In some preferred embodiments, collagen peptides as described above are fused to heterologous N and C terminal amino acid sequences which support the triple-helical polyproline II helix structure, for example $GX_aX_b$ repeat sequences, where $X_a$ and $X_b$ are any amino acid other than G, preferably $X_a$ is independently any amino acid except glycine or O. Suitable triple-helical sequences include GPP and/or GPO repeats. For example, $(GPP)_n$, wherein n is 2-6 or more and $(GPO)_{n1}$ where $n_1$ is 2-6 or more.

Preferably a collagen peptide comprises multiple repeats, e.g. 2, 3, 4, 5 or 6, of the sequence 'GPP' at its N-terminal and C-terminal ends. For example, a collagen peptide may comprise the sequence (GPP)$_5$ (SEQ ID NO:3) at its N-terminal and C-terminal ends. In some embodiments, a collagen peptide may comprise one or more copies of the sequence 'GPC' to facilitate disulphide cross-linking. For example, a peptide may comprise the sequence GPC(GPP)$_5$ (SEQ ID NO:36) at its N-terminal and the sequence (GPP)$_5$GPC (SEQ ID NO:37) at its C-terminal ends.

For example, suitable collagen peptides may comprise the sequence (GPP)$_5$GPOGPAGFOGAO-(GPP)$_5$ (SEQ ID NO:5) or (GPP)$_5$-GAOGPAGFA-(GPP)$_5$ (SEQ ID NO:6) or, more preferably, GPC(GPP)$_5$-GPOGPAGFOGAO-(GPP)$_5$ GPC (SEQ ID NO:224) or GPC(GPP)$_5$-GAOGPAG FA-(GPP)$_5$GPC (SEQ ID NO:225).

Heterologous amino acids at the N or C terminal of a collagen peptide or polypeptide described herein may form an additional sequence or motif. Indeed, any desired additional amino acid sequence may be included in a fusion with a peptide described herein, including non-triple helical extensions of the triple helix formed by trimerising of the peptides. Suitable heterologous amino acid sequences include the sequences of bioactive peptides and polypeptides, including chemokines and cytokines, such as RANKL and osteoprotegrin (OPG).

Collagen peptides and polypeptides described herein preferably form trimers under appropriate conditions.

A peptidyl trimer may be a homotrimer or a heterotrimer of a collagen peptide described herein. For example, a collagen peptidyl trimer which binds OSCAR may comprise three peptides comprising the amino acid sequence;

GX$_1$OGX$_2$X$_3$GX$_4$X$_5$, (SEQ ID NO: 12)

wherein O is a hydroxyproline residue and
X$_1$ is independently any non-polar amino acid,
X$_2$ is independently P, A, or V,
X$_3$ is independently any amino acid,
X$_4$ is independently F, S, D, Y, A or E;
X$_5$ is independently any amino acid.

In some embodiments, a collagen peptidyl trimer may comprise three peptides comprising the amino acid sequence;

GX$_1$OGX$_2$X$_3$GX$_4$X$_5$, (SEQ ID NO: 12)

wherein O is a hydroxyproline residue and
X$_1$ is independently A, P or G in at least one of said peptides, preferably P or A, more preferably A,
X$_2$ is independently P, A, or V in at least one of said peptides, more preferably P or A,
X$_3$ is independently A, M, P, O, Q, or S in at least one of said peptides; more preferably A or S,
X$_4$ is independently F, S, D, Y, A or E in at least one of said peptides; preferably F, S, D or Y, most preferably F,
X$_5$ is independently O, A, R or Q in at least one of said peptides, preferably O.

For example;
X$_1$ may be A, P or G in one, two or three of said peptides of the trimer.
X$_2$ may be P, A, or V in one, two or three of said peptides of the trimer.
X$_3$ may be A, M, P, O, Q, or S in one, two or three of said peptides of the trimer.
X$_4$ may be F, S, D, Y, A or E in one, two or three of said peptides of the trimer.
X$_5$ may be O, A, R or Q in one, two or three of said peptides of the trimer.

The production of collagen heterotrimers is described, for example, in Slatter D A et al J Mol Biol. (2006) 2;359(2):289-98.

A peptide which forms a peptidyl trimer may be fused to one or more sequences which are not naturally fused to the peptide, for example one or more heterologous amino acids, to form non-naturally occurring peptide and polypeptide fusions, as described above.

In some embodiments, peptides may be cross-linked within the trimer, for example using covalent bonds e.g. hexanoic acid cross-linking (such as the lysyl-lysyl amino hexanoate cross-linking). Alternatively, a disulphide knot may be produced and selectively protected and deprotected to link three chains successively and in register.

In other embodiments, peptides may trimerise without any cross-linking, and trimers consisting of peptides as described herein may be provided without cross-linking. A peptidyl trimer may be produced by providing peptides as described herein and causing or allowing (under appropriate conditions) the peptides to associate to form a trimer.

Triple helical structure may be determined by any convenient technique, for example polarimetry or circular dichroism. Trimerization may be followed by isolation of trimers, e.g. for subsequent use and/or manipulation.

Collagen peptides as described herein and trimers thereof may be useful in modulating the activation and/or differentiation of osteoclast-associated receptor expressing cells, e.g. by activating OSCAR-mediated signalling. For example, a collagen peptide may stimulate the differentiation and/or activation of the osteoclast-associated receptor (OSCAR) expressing cell for example by specific binding to OSCAR. Alternatively, a collagen peptide may inhibit the differentiation and/or activation of the osteoclast-associated receptor (OSCAR) expressing cell, for example by blocking the binding of OSCAR to collagen ligands.

Suitable collagen peptides and trimers thereof bind to an osteoclast-associated receptor. For example, a collagen peptide may bind to an osteoclast-associated receptor with the same or better affinity than a collagen peptide comprising a sequence selected from the group of:

| | |
|---|---|
| GPOGPAGFOGAO, | (SEQ ID NO: 15) |
| GAOGPAGFA, | (SEQ ID NO: 16) |
| GERGETGPOGPAGFOGAOGQN, | (SEQ ID NO: 17) |
| GPOGPAGFOGAOGQNGEOGGK, | (SEQ ID NO: 18) |
| GAOGPAGFOGAO, | (SEQ ID NO: 19) |
| GPOGAAGFOGAO, | (SEQ ID NO: 20) |
| GPOGPAGFAGAO, | (SEQ ID NO: 21) |
| GPOGPAGFOGAA, | (SEQ ID NO: 22) |
| GAOGPAGSA, | (SEQ ID NO: 23) |
| GAOGVMGFA, | (SEQ ID NO: 24) |
| GAOGPAGFAGEA, | (SEQ ID NO: 25) |
| GAOGAAGFA, | (SEQ ID NO: 26) |
| GAOGPPGFA, | (SEQ ID NO: 27) |
| GAOGPOGFA, | (SEQ ID NO: 28) |
| GAOGPQGFA, | (SEQ ID NO: 29) |

```
GAOGASGDR,                    (SEQ ID NO: 30)

GAOGPAGYA,                    (SEQ ID NO: 31)

GPOGPAGAOGAO,                 (SEQ ID NO: 32)

GAOGPAGEA,                    (SEQ ID NO: 33)

GAOGPAGFD, and                (SEQ ID NO: 34)

GAOGPQGPA.                    (SEQ ID NO: 35)
``` wherein O is a hydroxyproline residue.

Preferably, a collagen peptide binds to an osteoclast-associated receptor with the same or better affinity than a collagen peptide comprising an amino acid sequence selected from the group of: GPOGPAGFOGAO (SEQ ID NO:15) and GAOGPAGFA (SEQ ID NO:16). For example, a collagen peptide may bind to an osteoclast-associated receptor with the same or better affinity than collagen peptides GPC(GPP)$_5$-GPOG-PAGFOGAO-(GPP)$_5$GPC (SEQ ID NO:224) or GPC (GPP)$_5$-GAOGPAGFA-(GPP)$_5$GPC (SEQ ID NO:225).

A collagen peptide or trimer as described herein may show no binding or substantially no binding to known collagen receptors, such as integrin $\alpha_2\beta_1$, the discoidin domain receptors DDR1 and DDR2 or platelet glycoprotein VI.

Methods for determining the affinity of a collagen peptide for an osteoclast-associated receptor are well-known in the art and are also described elsewhere herein.

A collagen peptide or trimer as described herein may be provided in an isolated and/or purified form i.e. devoid of other collagen peptides or fragments or other biological molecules which are naturally found in association with collagen.

Collagen peptides for use as described herein are preferably synthetic i.e. produced by a synthetic or recombinant process.

For example, collagen peptides described herein may be generated wholly or partly by chemical synthesis. The peptides can be readily prepared, for example, according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); in J. H. Jones, The Chemical Synthesis of Peptides. Oxford University Press, Oxford 1991; in Applied Biosystems 430A Users Manual, ABI Inc., Foster City, Calif., in G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof. For example, peptides may be synthesized by Fmoc (N-(9-fluorenyl)methoxycarbonyl) chemistry as C-terminal amides on TentaGel R RAM resin in an automated synthesizer (e.g. Applied Biosystems Pioneer™).

Another convenient way of producing the collagen peptides described herein is to express nucleic acid encoding a precursor wherein proline appears in place of the desired hydroxyproline, by use of nucleic acid in an expression system. Production of GPO-containing peptides may be achieved for example by co-expression of an appropriate hydroxylase, as has been done with lysyl residues (Nokelainen et al. 1998 Matrix Biol. 16(6):329-38). For peptides containing Pro residues to be post-translationally converted by hydroxylation to Hyp (O), prolyl-hydroxylase may be co-expressed. Myllyharju, J. et al. *Biochem Soc trans* 2000, 4 353-7 describes an efficient expression system for recombinant human collagens which may be useful in providing peptides as described herein. This system uses the methylotrophic yeast *Pichia pastoris*, with co-expression of the desired peptides chains with the alpha- and beta-subunits of prolyl 4-hydroxylase.

In some embodiments, a collagen peptide or polypeptide as described herein may be chemically modified, for example, by addition of one or more polyethylene glycol molecules, sugars, phosphates, and/or other such molecules, where the molecule or molecules are not naturally attached to wild-type collagen proteins. Suitable chemical modifications are well known to those of skill in the art. The same type of modification may be present in the same or varying degree at several sites in the peptide or polypeptide. Also, a given the peptide or polypeptide may contain many types of modifications.

Modifications can occur anywhere in the peptide sequence, including the peptide backbone, the amino acid side-chains, and the amino or carboxyl termini. Modifications include, for example, acetylation, acylation, ADP-ribosylation, amidation, covalent attachment of flavin, covalent attachment of a haem moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *Proteins-Structure And Molecular Properties*, 2nd Ed., T. E. Creighton, W. H. Freeman and Company, New York (1993) and Wold, F., "Posttranslational Protein Modifications: Perspectives and Prospects," pgs. 1-12 in *Posttranslational Covalent Modification Of Proteins*, B. C. Johnson, Ed., Academic Press, New York (1983); Seifter et al., *Meth. Enzymol.* 182:626-646 (1990) and Rattan et al., "Protein Synthesis: Posttranslational Modifications and Aging," Ann. N.Y. Acad. Sci. 663: 48-62 (1992).

In some embodiments, a protecting group may be coupled to the N- and/or C-terminal end of a collagen peptide to protect the collagen peptide from enzymatic digestion. Suitable protecting groups are well-known in the art.

Collagen peptides or polypeptides as described herein may be structurally modified. A structurally modified peptide is substantially similar in both three-dimensional shape and biological activity to a collagen peptide described herein and preferably comprises a spatial arrangement of reactive chemical moieties that closely resembles the three-dimensional arrangement of active groups in the peptide sequence. Examples of structurally modified peptides include pseudo-peptides, semi-peptides and peptoids.

Collagen peptides or polypeptides as described herein may be structurally modified to include one or more non-peptidyl bonds, for example pseudopeptide bonds. A number of suitable pseudopeptide bonds are known in the art, including retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.,* 41:561-566), reduced isostere pseudopeptide bonds (Couder, et al. (1993), *Int. J. Peptide Protein Res.,* 41:181-184), ketomethylene and methylsulfide bonds.

Collagen peptides or polypeptides comprising pseudopeptide bonds may have an identical amino acid sequence to the sequence described above, except that one or more of the peptide bonds are replaced by a pseudopeptide bond. In some embodiments, the most N-terminal peptide bond is substituted, since such a substitution will confer resistance to proteolysis by exopeptidases acting on the N-terminus. Further modifications also can be made by replacing chemical groups of the amino acids with other chemical groups of similar structure.

Collagen peptides or polypeptides as described herein may be structurally modified to eliminate peptide bonds. Suitable structurally modified peptides include peptoids (Simon, et al., 1992, *Proc. Natl. Acad. Sci. USA,* 89:9367-9371), which are oligomers of N-substituted glycines. The N-alkyl group of each glycine residue corresponds to the side chain of a natural amino acid. Some or all of the amino acids of a peptide may be replaced with the N-substituted glycine corresponding to the replaced amino acid.

Collagen peptides or polypeptides as described herein may be structurally modified to comprise one or more D-amino acids. For example, a peptide may be an enantiomer in which one or more L-amino acid residues in the amino acid sequence of the peptide is replaced with the corresponding D-amino acid residue or a reverse-D peptide, which is a peptide consisting of D-amino acids arranged in a reverse order as compared to the L-amino acid sequence described above. (Smith C. S. et al., *Drug Development Res.,* 15, pp. 371-379 (1988).

Methods of producing suitable structurally modified peptides are well known in the art.

A collagen peptide or polypeptide as described herein may be linked to a coupling partner, e.g. an effector molecule, a label, a marker, a drug, a toxin and/or a carrier or transport molecule, and/or a targeting molecule such as an antibody or binding fragment thereof or other ligand. Techniques for coupling peptides to both peptidyl and non-peptidyl coupling partners are well-known in the art.

For example, a collagen peptide or polypeptide may be conjugated to an active agent which exerts a biological effect, such as a pharmaceutical agent. A suitable pharmaceutical agent may produce a therapeutic effect on a disease condition. For example, a collagen peptide may be conjugated to a pharmaceutical agent which alters the activation and/or differentiation of an osteoclast-associated receptor (OSCAR) expressing cell. Exemplary pharmaceutical agents capable of altering the activation and/or differentiation of an OSCAR expressing cell include adjuvants, chemokines, cytokines e.g. RANKL, osteoprotegrin (OPG), fluorescent dyes, recombinant enzymes and proteins or protein fusions.

In some embodiments, a collagen peptide or peptidyl trimer may be attached or coated on to a solid surface or insoluble support. Methods for fixing peptides or polypeptides to insoluble supports are known to those skilled in the art. For example, collagen peptides or peptidyl trimers may be immobilised on the surface of a culture vessel. A culture vessel with a collagen peptide or trimer immobilised on its surface may be useful for culturing cells which express osteoclast-associated receptors (OSCAR).

Suitable culture vessels are well known in the art and include tissue culture plates, for example multi-well tissue culture plates such as 48- or 96-well plates.

A culture vessel with immobilised collagen peptides or peptidyl trimers may, for example, be useful in a method of screening for modulators of osteoclast-associated receptor (OSCAR) expressing cell differentiation and/or activity.

Culture vessels with immobilised collagen peptides or peptidyl trimers may be provided as part of a kit. In addition to culture vessels, such kits may comprise reagents for characterizing OSCAR expressing cells. For example, osteoclasts can be characterised by reagents suitable for detection of tartrate resistant acid phosphatase (TRAP). Reagents suitable for detecting tartrate resistant acid phosphatase (TRAP) are well known in the art and are commercially available (e.g. TRAP-staining kit #386A-1KT Sigma-Aldrich).

Collagen peptides and peptidyl trimers as described herein may also be useful in a method of treatment. For example, a collagen peptide may be used in a method of treating a bone defect or a disorder characterized by altered differentiation and/or activation of an osteoclast-associated receptor (OSCAR) expressing cell.

A collagen peptide or peptidyl trimer may also be useful in the manufacture of a medicament for the treatment of a bone defect or a disorder characterized by altered differentiation and/or activation of an osteoclast-associated receptor (OSCAR) expressing cell.

A method of treating a disorder characterized by altered differentiation and/or activation of an OSCAR expressing cell may comprise administering a collagen peptide or peptidyl trimer to an individual in need thereof.

Disorders characterized by altered differentiation and/or activation of an osteoclast-associated receptor (OSCAR) expressing cell include: osteopetrosis, primary bone cancer, secondary bone cancer, osteoporosis, rheumatoid arthritis, acute myeloid leukaemia, multiple myeloma, osteoarthritis and other osteolytic diseases.

In some preferred embodiments, collagen peptides or peptidyl trimers described herein may be useful in the treatment of disorders characterized by altered differentiation and/or activation of osteoclasts or osteoclast precursor cells, such as osteopetrosis, primary bone cancer, secondary bone cancer, osteoporosis, and rheumatoid arthritis.

For example, collagen peptides or peptidyl trimers described herein may be useful in the treatment of disorders characterized by decreased differentiation and/or activation of osteoclasts or osteoclast precursor cells, such as osteopetrosis, by increasing the differentiation of osteoclast precursor cells and/or increasing the activation of osteoclasts.

Collagen peptides or peptidyl trimers described herein may also be useful in the treatment of disorders characterized by increased differentiation and/or activation of osteoclasts or osteoclast precursor cells, such as primary bone cancer, secondary bone cancer, osteoporosis, and rheumatoid arthritis. Collagen peptides or peptidyl trimers described herein may, for example, decrease the differentiation of osteoclast precursor cells and/or decrease the activation of (mature) osteoclasts by blocking the binding of OSCAR to collagen ligands and reducing OSCAR-mediated cell signalling.

In other embodiments, collagen peptides described herein may be useful in the treatment of disorders characterized by altered differentiation and/or activation of myeloid cells, monocytes, and/or macrophages, such as acute myeloid leukaemia and multiple myeloma. Collagen peptides described herein may, for example, modulate the differentiation and/or activation of these cells.

Collagen peptides or peptidyl trimers described herein may also be useful in the treatment of bone defects. For example, a method of treating a bone defect in an individual may comprise administering a collagen peptide or peptidyl trimer to an individual in need thereof.

The peptide or peptidyl trimer may for example be administered locally at the site of the bone defect by any convenient technique. The peptide or peptidyl trimer increases the recruitment of osteoclasts to the site of bone defect. This recruitment may improve bone turnover and coupling between bone resorption and formation thereby facilitating the repair of bone tissue at the site of bone defect.

A bone defect may be any site at which the structure of the bone is disrupted or damaged. Defects may include cracks, discontinuities, fractures, non-unions or sites of bone implants.

Bone implants are commonly used for a range of medical applications and may include autologous or allopathic bone tissue or implants from artificial materials, such as stainless steel, titanium or ceramic. In some embodiments, a bone implant may be coated with a peptide or peptidyl trimer as described herein to facilitate bone repair at the site of implantation.

Collagen peptides or peptidyl trimers, as referred to herein, may also be used for modulating differentiation and/or activation of an osteoclast-associated receptor (OSCAR) expressing cell in vitro. For example, a method of modulating differentiation and/or activation of an osteoclast-associated receptor (OSCAR) expressing cell in vitro may comprise:

contacting an osteoclast-associated receptor (OSCAR) expressing cell with a collagen peptide as described herein.

The collagen peptide or peptidyl trimer modulates differentiation and/or activation of the OSCAR expressing cell.

In some embodiments, the differentiation and/or activation of the OSCAR expressing cell may be increased in the presence of a collagen peptide, compared with the level of differentiation and/or activation in the absence of the collagen peptide.

In other embodiments, the differentiation and/or activation of the OSCAR expressing cell may be decreased in the presence of a collagen peptide or peptidyl trimer, compared with the level of differentiation and/or activation in the absence of the collagen peptide.

The collagen peptide may be immobilized on a solid support. Conveniently, the solid support may be within a culture vessel for example, a multi-well tissue culture plate, as described above.

The differentiation of the OSCAR expressing cell, e.g. an osteoclast precursor cell, may be determined by any convenient technique, for example by staining for tartrate resistant acid phosphatase (TRAP), e.g. using a TRAP-staining kit (SIGMA), as described herein.

The activation of an OSCAR expressing cell may be determined by any convenient technique, for example by determining the level or amount of OSCAR signalling using a suitable reporter cell line. Conveniently, the OSCAR-CD3ξ NFAT-GFP reporter cell line described herein may be used to determine the effect of the collagen peptide on OSCAR signalling in osteoclasts.

Other suitable approaches for determining the differentiation and/or activation of OSCAR expressing cells include: western blotting for the post-translational activation of signalling pathways e.g. phosphorylation, assays for production of proteins induced or downregulated e.g. chemokines or cytokine production by ELISA or flow cytometry (Merck et al 2004, 2005 & 2006), calcium flux experiments (see for example, Merck et al 2004, 2005 & 2006); cellular activation as defined by respiratory burst and production of free oxygen radicals (Merck et al 2006); cell trafficking during receptor-mediated endocytosis or phagocytosis and antigen presentation assays in monocytes, macrophages, neutrophils, dendritic cells or osteoclasts (Merck et al., 2004 & 2005); cell trafficking of collagens in osteoclasts during bone resorption (Nesbitt & Horton, 1997; Stenbeck & Horton 2004); microscopical determination of multinucleation and protein expression in OSCAR expressing cells; RT-PCR for genes induced or down-regulated through activation or differentiation; western blotting determination of proteins induced or down-regulated through activation or differentiation; and northern blotting determination of RNA molecules induced or down-regulated e.g. mRNA, micro RNA induced after activation or differentiation.

Other aspects of the invention relate to methods of screening for modulators, e.g. activators or inhibitors, of collagen-mediated differentiation and/or activation of cells which express osteoclast-associated receptors (OSCAR). Such modulators may, for example, be useful in the development of treatments for disorders characterized by altered differentiation and/or activation of OSCAR expressing cells, as described herein.

Methods of screening for modulators of collagen-mediated differentiation and/or activation of an OSCAR expressing cell may comprise contacting the OSCAR expressing cell with a collagen peptide as described herein in the presence or absence of a test compound and determining the differentiation and/or activation of the cell.

In some embodiments, the collagen peptide may have a positive effect on differentiation and/or activation of the OSCAR expressing cell, in the absence of test compound.

A change in the differentiation and/or activation of the OSCAR expressing cell which is mediated by the collagen peptide in the presence relative to the absence of the test compound is indicative that the test compound is a modulator of differentiation and/or activation.

An increase in collagen-mediated differentiation and/or activation of the OSCAR expressing cell in the presence of the test compound relative to its absence may be indicative that the test compound is an activator of collagen-mediated differentiation and/or activation of the OSCAR expressing cell.

A decreased in collagen-mediated differentiation and/or activation of the OSCAR expressing cell in the presence of the test compound relative to its absence may be indicative that the test compound inhibits or blocks collagen-mediated differentiation and/or activation of the OSCAR expressing cell. For example, a inhibitory compound may inhibit or block the binding of the collagen peptide to OSCAR.

The differentiation and/or activation of an OSCAR expressing cell may be determine as described above.

Suitable test compounds which may be screened using the methods described herein may be natural or synthetic chemical compounds used in drug screening programmes. Extracts of plants, microbes or other organisms which contain several characterised or uncharacterised components may also be used.

Combinatorial library technology provides an efficient way of testing a potentially vast number of different compounds for ability to modulate an interaction. Such libraries and their use are known in the art, for all manner of natural products, small molecules and peptides, among others. The use of peptide libraries may be preferred in certain circumstances.

The amount of test compound or compounds which may be added to a method of the invention will normally be determined by trial and error depending upon the type of compound used. Typically, from about 0.001 nM to 1 mM or more of putative inhibitor compound may be used, for example from 0.01 nM to 100 µM, e.g. 0.1 to 50 µM, such as about 10 µM.

Suitable test compounds for screening include compounds known to modulate differentiation and/or activation of OSCAR expressing cells. Such compounds include collagen peptides as described herein, TNF-family members (e.g. TNF, TRAIL etc.), RANKL, osteoprotegrin (OPG), M-CSF, GM-CSF, Interleukins: IL-1, IL-4, IL-6 family (e.g. IL-6, IL-11, Leukaemia inhibitory factor, oncostatin M etc.), IL-7, IL-8, IL-10, IL-12, IL-15, IL-17, IL-23 (Lorenzo and Choi, 2008), toll-like receptor (TLR) ligands and other inflammatory mediators e.g. LPS and anti-inflammatory mediators e.g. TGF-Beta and IL-10.

Suitable test compounds also include analogues, derivatives, variants and mimetics of any of the compounds listed above, for example compounds produced using rational drug design to provide test candidate compounds with particular molecular shape, size and charge characteristics suitable for modulating differentiation and/or activation of OSCAR expressing cells.

A test compound may be isolated and/or purified or alternatively, it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals for the treatment of a disorder characterized by altered osteoclast differentiation and/or activation, as described herein, or for preventing or delaying the onset of such a disorder. Methods described herein may thus comprise formulating the test compound in a pharmaceutical composition with a pharmaceutically acceptable excipient, vehicle or carrier for therapeutic application, as discussed further below.

Following identification of a compound which modulates the collagen-mediated differentiation and/or activation of an osteoclast-associated receptor (OSCAR) expressing cell, a method may further comprise modifying the compound to optimise its pharmaceutical properties.

The modification of a 'lead' compound identified as biologically active is a known approach to the development of pharmaceuticals and may be desirable where the active compound is difficult or expensive to synthesise or where it is unsuitable for a particular method of administration, e.g. peptides are not well suited as active agents for oral compositions as they tend to be quickly degraded by proteases in the alimentary canal. Modification of a known active compound (for example, to produce a mimetic) may be used to avoid randomly screening large number of molecules for a target property.

Modification of a 'lead' compound to optimise its pharmaceutical properties commonly comprises several steps. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR.

Computational analysis, similarity mapping (which models the charge, hydrophobicity/hydrophilicity and/or volume of a pharmacophore, rather than the bonding between atoms) and other techniques can be used in this modelling process.

In a variant of this approach, the three-dimensional structure of the compound which modulates differentiation and/or activation of an osteoclast-associated receptor (OSCAR) expressing cell is modelled. This can be especially useful where the compound changes conformation, allowing the model to take account of this in the optimisation of the lead compound.

A template molecule is then selected, onto which chemical groups that mimic the pharmacophore can be grafted. The template molecule and the chemical groups grafted on to it can conveniently be selected so that the modified compound is easy to synthesise, is likely to be pharmacologically acceptable, and does not degrade in vivo, while retaining the biological activity of the lead compound. The modified compounds found by this approach can then be screened to see whether they have the target property, or to what extent they exhibit it. Modified compounds include mimetics of the lead compound.

Further optimisation or modification can then be carried out to arrive at one or more final compounds for in vivo or clinical testing.

A compound identified and/or obtained using the present methods may be formulated into a pharmaceutical composition as described elsewhere herein.

While it is possible for an active compound such as a collagen peptide to be administered alone, it is preferable to present it as a pharmaceutical composition (e.g. formulation) comprising a collagen peptide, together with one or more pharmaceutically acceptable carriers, adjuvants, excipients, diluents, fillers, buffers, stabilisers, preservatives, lubricants, or other materials well known to those skilled in the art.

For example, a pharmaceutical composition may comprise a collagen peptide and a pharmaceutically acceptable excipient.

In addition, a pharmaceutical composition may comprise one or more additional active agents, including for example a pharmaceutical agent capable of modulating activation and/or differentiation of an OSCAR expressing cell.

For example, a pharmaceutical composition may comprise a collagen peptide, a pharmaceutical agent capable of activation and/or differentiation of an osteoclast-associated receptor (OSCAR) expressing cell, and a pharmaceutically acceptable excipient.

Pharmaceutical compositions comprising a collagen peptide or trimer as described herein, for example, admixed or formulated together with one or more pharmaceutically acceptable carriers, excipients, buffers, adjuvants, stabilisers, or other materials, as described herein, may be used in the methods described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio (an acceptably high chemotherapeutic index). Each carrier, excipient, etc.

must also be "acceptable" in the sense of being compatible with the other ingredients of the formulation.

Suitable carriers, excipients, etc. can be found in standard pharmaceutical texts, for example, Remington's Pharmaceutical Sciences, 21st edition, Mack Publishing Company, Easton, Pa., 2005.

The formulations may conveniently be presented in unit dosage form and may be prepared by any methods well-known in the art of pharmacy. Such methods include the step of bringing the active compound into association with a carrier which may constitute one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The collagen peptide or trimer or pharmaceutical composition comprising the collagen peptide or trimer may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly; or by non-absorbable enteric slow release.

Pharmaceutical compositions suitable for oral administration may be in tablet, powder liquid, solution, suspension, emulsion, syrup, or capsule form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Formulations suitable for parenteral administration include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example, from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Examples of techniques and protocols mentioned above can be found in Remington's Pharmaceutical Sciences, 21st edition, Mack Publishing Company, Easton, Pa., 2005.

It will be appreciated that appropriate dosages of the collagen peptide or trimer can vary from patient to patient. Determining the optimal dosage will generally involve the balancing of the level of diagnostic benefit against any risk or deleterious side effects of the administration. The selected dosage level will depend on a variety of factors including, but not limited to, the route of administration, the time of administration, the rate of excretion of the collagen peptide, other drugs, compounds, and/or materials used in combination, and the age, sex, weight, condition, general health, and prior medical history of the patient. The amount of synthetic collagen peptide or trimer and route of administration will ultimately be at the discretion of the physician, although generally the dosage will be to achieve concentrations of the collagen peptide or trimer at a lesion site without causing substantial harmful or deleterious side-effects.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

The collagen peptide, trimer or composition comprising a collagen peptide or trimer may be administered in a localised manner to a desired site or may be delivered in a manner in which it targets particular cells or tissues. For example, it may be administered directly to a tissue comprising OSCAR expressing cells.

Various further aspects and embodiments of the present invention will be apparent to those skilled in the art in view of the present disclosure. All documents and database entries mentioned in this specification are incorporated herein by reference in their entirety.

In the amino acid sequences set out herein, O denotes a hydroxyproline residue.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described above.

Experiments

Materials and Methods
Peptide Synthesis

The sequences of peptides used in this study are shown in Tables 1, 2 and 3. Peptides were synthesized by Fmoc (N-(9-fluorenyl)methoxycarbonyl) chemistry as C-terminal amides on TentaGel R RAM resin in an Applied Biosystems Pioneer automated synthesizer and purified as described (Merck et al 2004). All peptides were verified by mass spectrometry and shown to adopt triple-helical conformation by polarimetry. Briefly, The host-guest strategy (Arase H et al Science. 2002. 296(5571):1323-6) was applied, as in our previous studies (Raynal N, et al J Biol Chem. 2006. 281(7):3821-31), where the guest (primary) sequence of interest is placed between $(GPP)_5$ hosts, inert flanking sequences, that impart triple-helical conformation on the whole peptide. Each Toolkit peptide contains a guest sequence of 27 amino acids, the C-terminal 9 amino acids of which form the first 9 guest amino acids of the next peptide. Thus, the guest sequence of the Toolkit advances 18 amino acids along the triple-helical domains of type-II and -III collagen with each successive peptide, and a 9-amino-acid overlap is included between adjacent peptides.

Solid Phase Binding Assays 10 ug/ml of different collagens, proteins and peptides were resuspended in 0.01M Acetic-acid and immobilised overnight in Maxisorp 96-well ELISA plates (Nunc) at 4 degrees. Excess protein was then washed off and wells were blocked in 5% BSA in Tyrodes buffer +0.05% Tween (Ty-T) for 1 hour at room temperature (RT). The block was then removed and 100 µl purified Fc-fusion proteins (5 µg/ml) were incubated for 1 hour at RT. Fc-fusions were washed 5 times with 200 µl Ty-T, before detection with 100 µl goat anti-human-HRP conjugate (Sigma) diluted 1:10,000 in Ty-T for 1 hour at RT. Wells were then washed a further 5 times before development with peroxidise substrate +H202 (Pierce). Reactions were stopped with 2M H2SO4 before being read by a plate reader at 450 nm.

mAb Blocking Experiments

Fc-fusion proteins were pre-incubated with either 2.5 µg/ml anti-OSCAR mAb 11.1CN5 (Beckman coulter) or an IgG1 isotype-matched control mAb (Dako) for 1 hour at RT prior assessment of collagen-binding activity by ELISA. RBL-2H3 cells were incubated with 2.5 µg/ml anti-OSCAR mAb 11.1CN5 or an IgG1 isotype-matched control mAb before binding to 5 µg/ml type-I collagen-FITC before analysis by flow cytometry.

Bone Marrow Stromal Cells and Calvarial Osteoblasts

Bone marrow was flushed from the femur and tibia of C57/B6 mice and adherent bone marrow stromal cells (BMS) were cultured in α-MEM supplemented with 10% foetal calf serum (FCS) and 100 U/ml Penicillin and streptomycin. Calvarial osteoblasts (OB) were isolated from the calvariae of neonatal pups using standard procedures and cultured in DMEM supplemented with 10% foetal calf serum (FCS), 100 U/ml Penicillin and streptomycin, 100 µg/ml ascorbate, $10^{-8}$M vitamin 1,25-$(OH)_2D_3$ and $10^{-6}$M prostaglandin $E_2$ (ref). mOSCAR-Fc and hOSCAR-Fc binding to CD45-BMS and OB was assessed before and after collagenase treatment (30 minutes at 37° C.) by flow cytometry. Fc-fusion proteins were detected using goat-anti human IgG-PE (Southern biotechnologies).

OSCAR-CD3ξ NFAT-GFP Reporter 2B4 Cells

2B4 NFAT-GFP reporter cells were a kind gift from Lewis Lanier (Arase et al., Science. 2002. 296(5571):1323-6). The extracellular domain of human OSCAR was cloned into pDISPLAY, a construct which encodes an N-terminal HA tag and the transmembrane domain of the PDGF receptor (Invitrogen). The N-terminal tagged OSCAR and PDGFR transmembrane domain were then subcloned in frame with the cytoplasmic tail of the human CD3ξ chain encoded in the pMx puro retroviral vector. Phoenix cells were transfected with the resulting pMx puro OSCAR-CD3ξ construct and resulting virus was used to infect 2B4 NFAT-GFP reporter cells before selection single clones with 2.5 µg/ml puromycin. In OSCAR-CD3ξ reporter cell assays, tissue culture plates were coated overnight with different proteins and peptides in 0.01M acetic acid at 4° C. Excess proteins and peptides were washed 3 times with PBS and blocked for 1 hour in RPMI-1640 supplemented with 100 U/ml penicillin and streptomycin and 10% FCS before addition of OSCAR-CD3ξ reporter cells.

Osteoclast Cultures 48-well or 96-well tissue culture plates were coated with 10 µg/ml of different proteins and peptides in 0.01M acetic-acid overnight at 4° C. Excess protein and peptides were washed with three times with PBS before blocking in complete medium. Murine bone marrow was flushed from the tibias and fibias of 2-3 week old mice. Bone marrow was incubated overnight to removed adherent stromal cells and the non-adherent fraction (free of stromal cells and osteoblasts) was removed and cultured as bone marrow macrophages (BMM) for 3 days in 100 ng/ml murine M-CSF prior to osteoclast differentiation with 10 ng/ml M-CSF and either 30 ng/ml or 100 ng/ml murine RANK-L in coated tissue culture plates. Human osteoclasts were derived from healthy donors or from frozen PBMC from Nasu-Hakola (NH) patients deficient in TREM2 (patient 'NH2') or DAP12-deficient (patient 'NH6'). Peripheral blood monocytes were initially cultured as monocyte-derived dendritic cells in IL-4 and GM-CSF before differentiating into osteoclasts with 30 ng/ml human M-CSF and 100 ng/ml human RANK-L (Peprotech). Giant multi-nucleated osteoclasts were fixed with 4% paraformaldehyde before staining for tartrate resistant acid phosphatase (TRAP) with a TRAP-staining kit (Sigma).

Expression of Osteoclast-specific Genes by RT-PCR

Total RNA was isolated from murine osteoclast cultures incubated in the presence of BSA or OSCAR-binding triple-helical collagen peptides and reverse-transcribed into cDNA using superscript-III (Invitrogen). The following primers were used in RT-PCR to assess expression of murine osteoclast-specific genes; Cathepsin-K, 5'-GCAGTATAACAG-CAAGGTGG-3'(SEQ ID NO:39) and 5'-TTCATCCTGGC-CCACATATG-3'(SEQ ID NO:183); Matrix metalloproteinase-9, 5'TATCTGTATGGTCGTGGCTC-3' (SEQ ID NO:184) and 5'-CAAGTCGAATCTCCAGACAC-3'(SEQ ID NO:185); Calcitonin receptor, 5'-AGGAGGTC-CAGAGTGAAAAG-3'(SEQ ID NO:186) and 5'-TCTGGCAGCTAAGGTTCTTG-3' (SEQ ID NO:187); Integrin αV, 5'-CAACGAAGCCTTAGCAA-GAC-3'(SEQ ID NO:188) and 5'-ATTCCACAGCCCAAAGTGTG-3' (SEQ ID NO:189); A disintegrin and metalloproteinase domain 8, 5'-TGAATGCAAGGTGAAGCCAG-3'(SEQ ID NO:190) and 5'-GTAGACGCTGCTTGTTCATC-3'(SEQ ID NO:191); Glyceraldehyde-3-phosphate dehydrogenase, 5'-AAGGGCTCATGACCACAGTC-3'(SEQ ID NO:192) and 5'-GGCCCCTCCTGTTATTATGG-3'(SEQ ID NO:193); and OSCAR, 5'-ACTGCTGGTAACGGATCAGC-3'(SEQ ID NO:194) and 5'-TCCAAGGAGCCAGAA-CCTTC-3' (SEQ ID NO:195).

Results

OSCAR Binds Strongly to Collagens-I, -II and -III and Weakly to Collagen-IV

Figure 1:
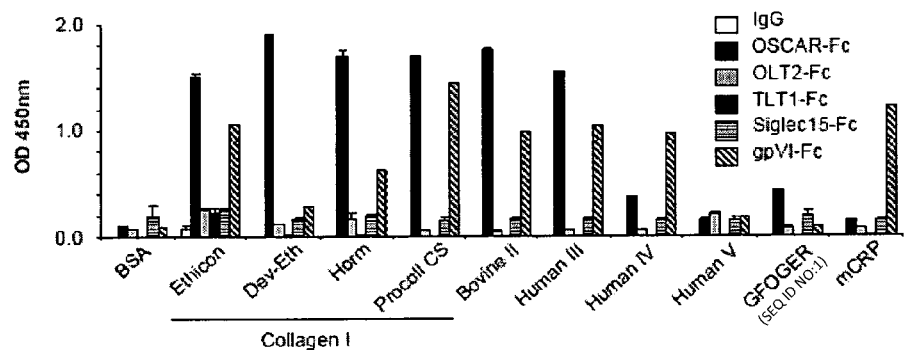
Figure 2:
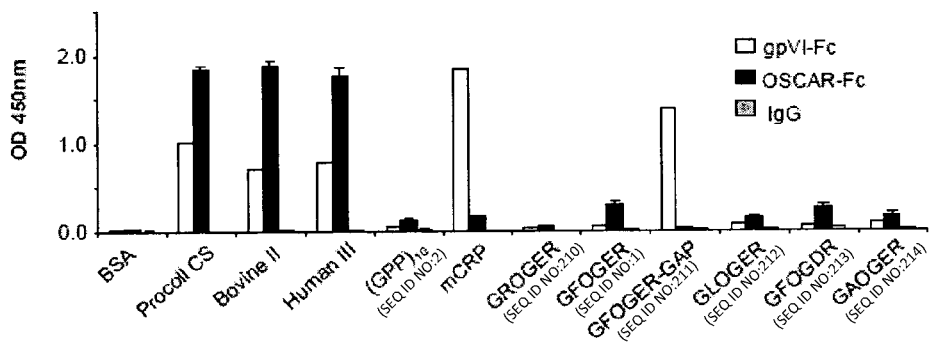
Figure 3:
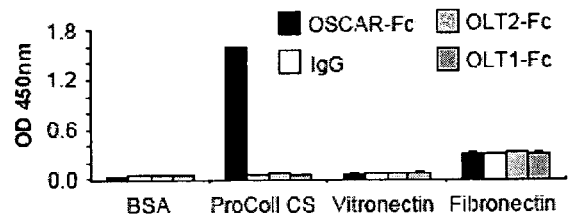
Figure 4:
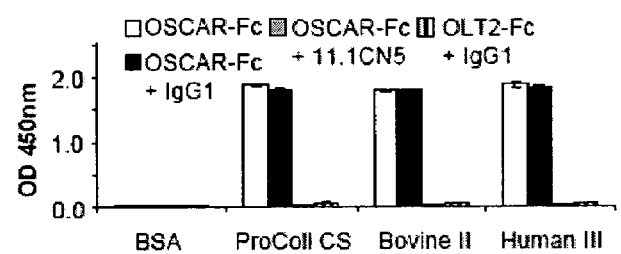
Figure 5:
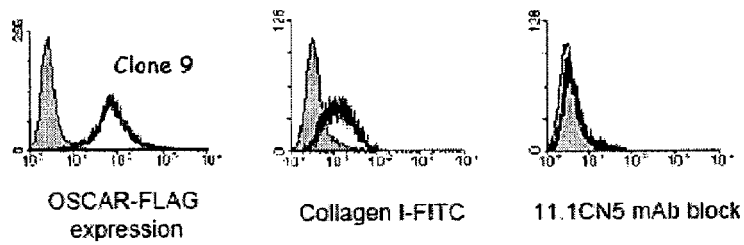
FIG. 5 shows that FITC-conjugated type-I collagen (type-I Collagen-FITC, 5 µg/ml) binds to an RBL-2H3 stable cell-line expressing OSCAR-FLAG (open histograms) but not untransfected cells (grey-shaded). This interaction is blocked with 2 µg/ml of anti-human OSCAR mAb 11.1CN5.
Figure 6:
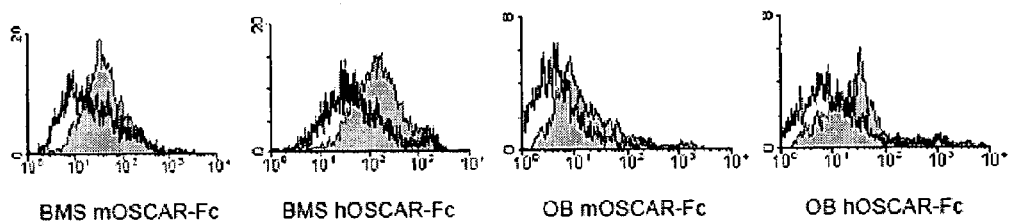
FIG. 6 shows that collagenase treatment (open histograms) removes the putative OSCAR ligand from prostaglandin-E2 and vitamin D3 stimulated murine bone marrow stromal cells (BMSC) and murine calvarial osteoblasts (OB) (grey-shaded histograms).

To search for an OSCAR ligand, we initially screened the ability of different extracellular matrix proteins to bind human OSCAR-Fc fusion protein by ELISA (FIGS. 1-6). Human OSCAR-Fc bound strongly to plates coated with collagens I, II and III, weakly to collagen IV and not at all to collagen V (FIGS. 1 & 2) or to the extracellular matrix proteins vitronectin or fibronectin (FIG. 3). Human OSCAR-Fc did not bind appreciably to triple-helical peptide ligands for known collagen receptors, such as integrin $\alpha_2\beta_1$ ('GFOGER' and peptide derivatives) or the ligand for GpVI, monomeric collagen related peptide (mCRP), providing indication that OSCAR has a distinct and specific collagen-binding motif (FIGS. 1 & 2). In contrast to gpVI, N-glycosylation had no effect on the collagen binding activity of human OSCAR-Fc (FIG. 20). Pre-incubation of OSCAR-Fc with the anti-human OSCAR mAb 11.1CN5 abolished binding of human OSCAR-Fc to collagens I, II and III, whereas an isotype matched control antibody had no effect (FIG. 4). In addition, type-I Collagen-FITC bound to RBL-2H3 cells stably expressing human OSCAR, but not to untransfected RBL-2H3 (FIG. 5). Type-I collagen-FITC binding was inhibited by pre-incubation of human OSCAR expressing RBL-2H3 cell with blocking anti-human OSCAR mAb 11.1CN5 (FIG. 5). Collagenase treatment removed the putative OSCAR ligand from murine bone marrow stromal cells and from murine calvarial osteoblasts activated with prostaglandin-E2 and Vitamin D3 (FIG. 6).

To establish a sequence-specific binding site for human OSCAR, the human OSCAR-Fc protein was screened against a library of overlapping triple-helical peptides encompassing the entire type-II and type-III collagen sequences (Tables 1 and 2).

OSCAR-Fc specifically bound to several peptides from the Toolkits II and -III. Alignment of the six Toolkit peptides that bound most strongly to OSCAR-Fc is shown in Table 4, from which a consensus OSCAR-binding motif was deduced (Table 5).

To test the specificity of this interaction, we synthesized derivatives of peptide III-36 encompassing the two halves of III-36 containing the amino-acid sequence 'GPOGPAG-FOGAO'(SEQ ID NO: 15); (underlined) which conforms to the predicted OSCAR-binding motif. . We also synthesized peptides trimmed to this putative minimal OSCAR binding motif, and performed an Alanine scan through the x and x' position of the Gxx' polymer (sequences of III-36 peptide and these derivatives are shown in Table 3). These peptides were used to assess the specificity of human OSCAR-Fc binding, and demonstrated a crucial role for the side chains of hydroxyproline at position (P) 3 and phenylalanine at P8 (FIG. 7). Additional amino-acid substitutions allowed us to explore the determinants of binding of this motif to human OSCAR-Fc (FIG. 8). We found that truncation of the C-terminal triplet (GAO) from the putative motif did not impair binding, leading the establishment of GxOGPx'GFO as a minimal OCP sequence. It is interesting that Phe is a determinant of OSCAR-binding, as also occurs with integrins, DDR2 and SPARC (osteonectin), but not GpVI or LAIR-1. This bulky, aromatic sidechain appears to offer a generic means of attachment to other proteins, but it can be substituted with Tyr, Asp or Ser (but not Pro or Glu) without loss of OSCAR-binding capacity. This might be explained if OSCAR interacted with collagen through an Arg-Phe or Arg-Tyr cation-n bond, so that alternatively, OSCAR Arg might interact with Asp or Ser by electrostatic or hydrogen bonding. Replacement of the N-terminal x residue with polar amino acids, Lys, Glu or Gln impairs binding, as does the insertion of the charged Asp (but not Arg) adjacent to F in the C-terminal triplet. These data, shown in FIG. 8, are consistent with a largely non-polar binding trench on OSCAR, from which triple-helices are excluded if they contain bulky or polar sidechains at their N-terminus.

OSCAR Peptide Ligands Induce Signalling

A human OSCAR-CD3ξ NFAT-GFP reporter cell-line was used to assess whether the OSCAR-binding collagen peptides (OCPs) identified above could transduce intracellular signals. GFP was expressed when OSCAR-CD3ξ NFAT-GFP reporter cells were plated onto tissue culture plates coated with collagens-I, -II, -III and -IV and to plates coated with the majority of OCPs recognised by human OSCAR-Fc, but not plates coated with BSA or (GPP)$_{10}$ (FIGS. 9 and 10). Weak GFP expression was observed when OSCAR-CD3ξ, NFAT-GFP reporter cells were cultured on plates coated collagen-V or with triple-helical peptides that did not bind appreciably to human OSCAR-Fc by ELISA (FIGS. 9 and 10).

The hOSCAR-CD3ξ NFAT-GFP reporter cell-line was also screened against the collagen-II and collagen-III overlapping homotrimeric collagen peptide libraries (FIGS. 11 and 12). Signalling generally paralleled that of OSCAR-Fc binding, although there were some exceptions to this. The reasons for the imprecise fit between binding and activation signalling are not known. They may relate to threshold or sensitivity differences between the two assays e.g. addition of 0.05% Tween-20 in ELISA or the dimeric nature of OSCAR-Fc. Although repeatable, the differences are not substantive. These results show that OSCAR binds to a sequence-specific collagen motif and OSCAR recognition of this motif can induce intracellular signalling.

Ligand Binding to OSCAR Enhances Osteoclastogenesis

Given the costimulatory effect of OSCAR and FcRγ on osteoclastogenesis, it was tested whether OCPs that induces OSCAR signalling would also enhance osteoclastogenesis.

OCPs enhanced in vitro osteoclastogenesis of human peripheral blood monocytes after 7 days culture with RANKL in wells coated with the OCPs, (GPP)$_5$-GPOGPAG-FOGAO-(GPP)$_5$ (SEQ ID NO:5) and (GPP)$_5$-GAOG-PAGFA-(GPP)$_5$ (SEQ ID NO:6), compared to wells coated with BSA-, (GPP)$_{10}$-(SEQ ID NO:2), or the control triple-helical peptide (GPP)$_5$-GLOGPSGEO-(GPP)$_5$ (SEQ ID NO:4) (FIG. 13).

This enhanced osteoclastogenesis was inhibited when the same OC cultures were treated with blocking mAb 11.1CN5 but not an isotype control mAb to MHC class I, showing that this effect was specific to the OSCAR/OCP interaction (FIG. 14). Examples of the giant TRAP+ multinuclear cells generated under these conditions are shown in FIG. 15

The costimulatory effect of plate-bound OCP also promoted the in vitro osteoclastogenesis of wild-type mouse BMMs (FIG. 16), but was not observed with cultures from OSCAR-deficient (OSCAR-/-) BMM or with cultures from FcRγ-/- BMMs (FIG. 15), the adaptor through which OSCAR is known to signal.

Remarkably, OCPs rescued the in vitro osteoclastogenic defect in OC cultures from murine DAP12-/- BMMs (FIG. 16) but not BMM from FcRγ-/- DAP12-/- mice, which did not develop OCs under any of the culture conditions analysed. The giant multinuclear DAP12 -/- cells rescued by OCP stained for TRAP (FIG. 17A), formed actin rings (FIG. 17B), and expressed OC-specific genes, such as cathepsin K, calcitonin receptor, integrin α$_v$, a disintegrin and metalloproteinase domain 8 (ADAM8), matrix metalloproteinase 9 (MMP9) and OSCAR by RT-PCR, compared to BM cells treated with M-CSF for 3 days in the absence of RANK-L.

To show definitively that the OCP-mediated rescue of DAP12-deficient cells was specifically due to OSCAR, and not another collagen binding receptor, we generated OSCAR-/-DAP12-/- mice and compared the rate of osteoclastogenesis to OSCAR+/+DAP12-/- littermates in the presence or absence of OCP. OSCAR+/+DAP12+/+ littermates displayed enhanced osteoclastogenesis in a similar fashion to wild-type C5BL/6 and 129 mice. Similarly to DAP12-/- cells, OSCAR+/+DAP12-/- precursors developed giant TRAP+ multinuclear cells in the presence of OCP, whereas OSCAR-/-DAP12-/- did not develop OC, similar to FcRγ-/-DAP12-/- cells.

To show that this effect was OSCAR-specific and not due to an unidentified collagen binding receptor, we retrovirally transduced OSCAR-/-DAP12-/- BMM with OSCAR and included DAP12, as a positive control, and backbone empty pMx vector, as a negative control. Retroviral transduction of DAP12 restored osteoclastogenesis in all conditions tested, as expected (FIGS. 18 & 19), whereas control transduction with the backbone pMx retroviral vector did not (FIG. 19). Retroviral transduction with mouse OSCAR rescued osteoclastogenesis in OCP-coated wells, but not OVA- or BSA-coated wells (FIGS. 18 & 19), showing the rescue of DAP12−/− cells was due to the OSCAR/OCP interaction. Giant TRAP+ multinuclear cells also developed in (GPP)$_{10}$-coated wells but to a lesser extent. These results occurred because of retroviral overexpression of murine OSCAR, since NFAT-GFP reporter cells retrovirally transduced with mouse OSCAR express GFP after incubation in wells coated with (GPP)$_{10}$. This also occured upon retroviral transduction of both the 'long' signal peptide (SP-L) isoform of mouse OSCAR (FIG. 18) or the 'short' signal peptide isoform (SP-S), showing this effect was due to retroviral overexpression and not the differences present in the murine OSCAR isoforms expressed. It is notable that neither DAP12−/− (FIG. 16) or OSCAR+/+ DAP12−/− cells, which express endogenous RANKL-induced OSCAR, do not form giant TRAP+ multinucleated cells in plates coated with (GPP)$_{10}$ and that this was only exhibited after retroviral transduction of OSCAR in OC and 2B4 NFAT-GFP reporter cells.

Ligand Binding to OSCAR Rescues Osteoclastogenesis of Nasu-Hakola Patients.

We assessed whether OSCAR OCPs could rescue the in vitro osteoclastogenic defect in cultures of peripheral blood monocytes from Nasu-Hakola (NH) patients supplemented with M-CSF and RANKL from either TREM2—(FIG. 20 RHS) and DAP12-deficient (FIG. 20 LHS) NH patients. Giant TRAP+ multinuclear cells developed from monocytes isolated from both TREM2-deficient (NH2) and DAP12-deficient (NH6) NH patients in OCP-coated wells, but not in wells coated with BSA or (GPP)$_{10}$ (FIG. 21).

We also assessed whether soluble triple-helical OSCAR-binding peptides would block the binding of human OSCAR-Fc binding to immobilised triple-helical peptides. FIG. 24 shows that soluble triple-helical peptides can block OSCAR-Fc binding to the same immobilised peptide. This shows soluble triple-helical peptides can be used to block OSCAR binding, and therefore signalling, in vitro or in vivo.

Triple-helical conformation of the OSCAR-binding motif was shown to be essential for signalling by determining the responses of the human and murine OSCAR-CD3Zeta NFAT-GFP reporter cell-lines to: immobilised BSA; a linear peptide containing the minimal OSCAR-binding sequence 'GPOG-PAGFO'(SEQ ID NO:10) (GPCGPOGPAGFOGPC-NH2, Mass =1,341.54 Da); and a triple-helical peptide designed to the minimal OSCAR-binding sequence' (GPP)$_5$-GPOG-PAGFO -(GPP)(SEQ ID NO:11) (GPC(GPP)$_5$-GPOG-PAGFO-(GPP)5GPC-NH2, Mass =3,854.42 Da). The linear and triple-helical status of these peptides was confirmed by polarimetry.

The results are shown in FIG. 25. Both the human and murine OSCARCD3Zeta NFAT-GFP reporter cell-lines were found to express GFP only in response to the triple-helical conformation of the minimal OSCAR-binding sequence. This confirms that, like the triple-helical conformation of native collagen, only triple-helical peptides containing an OSCAR-binding motif are recognised by OSCAR and not a linear motif.

The above data demonstrate that OSCAR binds to a specific collagen signature to promote osteoclastogenesis by a DAP12-independent pathway. Elucidation of the OSCAR:collagen pathway has important implications, not just for the alternative pathways of osteoclastogenesis that may be operating in TREM2- and DAP12-deficient osteoporotic pathologies, such as Nasu-Hakola disease, but also for understanding the molecular signals promoting osteoclastogenesis, and hence bone resorption, operating within the Bone Remodelling Compartment (BRC). The OSCAR:collagen axis, in conjunction with RANKL, may deliver costimulatory extracellular matrix signals that would drive osteoclastogenesis specifically on remodelling bone surfaces as defined by the expression of these ligands within the BRC. We show above that OSCAR can specifically bind to collagen II and induce signalling. OSCAR may therefore be a versatile collagen receptor that can recognise different types of collagens to sense the nature of the extracellular matrix environment to promote osteoclastogenesis.

Human OSCAR is widely expressed amongst haematopoietic cells, where it may serve other roles. OSCAR may also contribute to altered leukocyte function when collagens are exposed to the circulation, for example in the recruitment of macrophages to atherosclerotic lesions, or in other inflammatory compartments.

TABLE 1

| # | Peptide Sequence | Mass (Da) | SEQ ID NO: |
|---|---|---|---|
| 1 | GPC-(GPP)5-GPMGPMGPRGPOGPAGAOGPQGFQGNO-(GPP)5-GPC-NH2 | 5558 | 40 |
| 2 | GPC-(GPP)5-GPQGFQGNOGEOGEOGVSGPMGPRGPO-(GPP)5-GPC-NH2 | 5648 | 41 |
| 3 | GPC-(GPP)5-GPMGPRGPOGPOGKOGDDGEAGKOGKA-(GPP)5-GPC-NH2 | 5572 | 42 |
| 4 | GPC-(GPP)5-GEAGKOGKAGERGPOGPQGARGFOGTO-(GPP)5-GPC-NH2 | 5621 | 43 |
| 5 | GPC-(GPP)5-GARGFOGTOGLOGVKGHRGYOGLDGAK-(GPP)5-GPC-NH2 | 5710 | 44 |
| 6 | GPC-(GPP)5-GYOGLDGAKGEAGAOGVKGESGSOGEN-(GPP)5-GPC-NH2 | 5533 | 45 |
| 7 | GPC-(GPP)5-GESGSOGENGSOGPMGPRGLOGERGRT-(GPP)5-GPC-NH2 | 5668 | 46 |
| 8 | GPC-(GPP)5-GLOGERGRTGPAGAAGARGNDGQOGPA-(GPP)5-GPC-NH2 | 5503 | 47 |
| 9 | GPC-(GPP)5-GNDGQOGPAGPOGPVGPAGGOGFOGAO-(GPP)5-GPC-NH2 | 5385 | 48 |
| 10 | GPC-(GPP)5-GGOGFOGAOGAKGEAGPTGARGPEGAQ-(GPP)5-GPC-NH2 | 5423 | 49 |
| 11 | GPC-(GPP)5-GARGPEGAQGPRGEOGTOGSOGPAGAS-(GPP)5-GPC-NH2 | 5447 | 50 |

TABLE 1-continued

| # | Peptide Sequence | Mass (Da) | SEQ ID NO: |
|---|---|---|---|
| 12 | GPC-(GPP)5-GSOGPAGASGNOGTDGIOGAKGSAGAO-(GPP)5-GPC-NH2 | 5295 | 51 |
| 13 | GPC-(GPP)5-GAKGSAGAOGIAGAOGFOGPRGPOGPQ-(GPP)5-GPC-NH2 | 5417 | 52 |
| 14 | GPC-(GPP)5-GPRGPOGPQGATGPLGPKGQTGEOGIA-(GPP)5-GPC-NH2 | 5510 | 53 |
| 15 | GPC-(GPP)5-GQTGEOGIAGFKGEQGPKGEOGPAGPQ-(GPP)5-GPC-NH2 | 5607 | 54 |
| 16 | GPC-(GPP)5-GEOGPAGPQGAOGPAGEEGKRGARGEO-(GPP)5-GPC-NH2 | 5558 | 55 |
| 17 | GPC-(GPP)5-GKRGARGEOGGVGPIGPOGERGAOGNR-(GPP)5-GPC-NH2 | 5628 | 56 |
| 18 | GPC-(GPP)5-GERGAOGNRGFOGQDGLAGPKGAOGER-(GPP)5-GPC-NH2 | 5680 | 57 |
| 19 | GPC-(GPP)5-GPKGAOGERGPSGLAGPKGANGDOGRO-(GPP)5-GPC-NH2 | 5529 | 58 |
| 20 | GPC-(GPP)5-GANGDOGROGEOGLOGARGLTGROGDA-(GPP)5-GPC-NH2 | 5606 | 59 |
| 21 | GPC-(GPP)5-GLTGROGDAGPQGKVGPSGAOGEDGRO-(GPP)5-GPC-NH2 | 5562 | 60 |
| 22 | GPC-(GPP)5-GAOGEDGROGPOGPQGARGQOGVMGFO-(GPP)5-GPC-NH2 | 5650 | 61 |
| 23 | GPC-(GPP)5-GQOGVMGFOGPKGANGEOGKAGEKGLO-(GPP)5-GPC-NH2 | 5625 | 62 |
| 24 | GPC-(GPP)5-GKAGEKGLOGAOGLRGLOGKDGETGAA-(GPP)5-GPC-NH2 | 5536 | 63 |
| 25 | GPC-(GPP)5-GKDGETGAAGPOGPAGPAGERGEQGAO-(GPP)5-GPC-NH2 | 5447 | 64 |
| 26 | GPC-(GPP)5-GERGEQGAOGPSGFQGLOGPOGPOGEG-(GPP)5-GPC-NH2 | 5577 | 65 |
| 27 | GPC-(GPP)5-GPOGPOGEGGKOGDQGVOGEAGAOGLV-(GPP)5-GPC-NH2 | 5458 | 66 |
| 28 | GPC-(GPP)5-GEAGAOGLVGPRGERGFOGERGSOGAQ-(GPP)5-GPC-NH2 | 5638 | 67 |
| 29 | GPC-(GPP)5-GERGSOGAQGLQGPRGLOGTOGTDGPK-(GPP)5-GPC-NH2 | 5917 | 68 |
| 30 | GPC-(GPP)5-GTOGTDGPKGASGPAGPOGAQGPOGLQ-(GPP)5-GPC-NH2 | 5401 | 69 |
| 31 | GPC-(GPP)5-GAQGPOGLQGMOGERGAAGIAGPKGDR-(GPP)5-GPC-NH2 | 5561 | 70 |
| 32 | GPC-(GPP)5-GIAGPKGDRGDVGEKGPEGAOGKDGGR-(GPP)5-GPC-NH2 | 5525 | 71 |
| 33 | GPC-(GPP)5-GAOGKDGGRGLTGPIGPOGPAGANGEK-(GPP)5-GPC-NH2 | 5444 | 72 |
| 34 | GPC-(GPP)5-GPAGANGEKGEVGPOGPAGSAGARGAO-(GPP)5-GPC-NH2 | 5344 | 73 |
| 35 | GPC-(GPP)5-GSAGARGAOGERGETGPOGPAGFAGPO-(GPP)5-GPC-NH2 | 5450 | 74 |
| 36 | GPC-(GPP)5-GPAGFAGPOGADGQOGAKGEQGEAGQK-(GPP)5-GPC-NH2 | 5495 | 75 |
| 37 | GPC-(GPP)5-GEQGEAGQKGDAGAOGPQGPSGAOGPQ-(GPP)5-GPC-NH2 |  | 76 |
| D37E | GPC-(GPP)5-GEQGEAGQKGEAGAOGPQGPSGAOGPQ-(GPP)5-GPC-NH2 | 5475 | 77 |
| 38 | GPC-(GPP)5-GPSGAOGPQGPTGVTGPKGARGAQGPO-(GPP)5-GPC-NH2 | 5412 | 78 |
| 39 | GPC-(GPP)5-GARGAQGPOGATGFOGAAGRVGPOGSN-(GPP)5-GPC-NH2 | 5436 | 79 |
| 40 | GPC-(GPP)5-GRVGPOGSNGNOGPOGPOGPSGKDGPK-(GPP)5-GPC-NH2 | 5525 | 80 |
| 41 | GPC-(GPP)5-GPSGKDGPKGARGDSGPOGRAGEOGLQ-(GPP)5-GPC-NH2 | 5561 | 81 |
| 42 | GPC-(GPP)5-GRAGEOGLQGPAGPOGEKGEOGDDGPS-(GPP)5-GPC-NH2 | 5561 | 82 |
| 43 | GPC-(GPP)5-GEOGDDGPSAEGPOGPQGLAGQRGIV-(GPP)5-GPC-NH2 | 5531 | 83 |
| 44 | GPC-(GPP)5-GLAGQRGIVGLOGQRGERGFOGLOGPS-(GPP)5-GPC-NH2 | 5705 | 84 |
| 45 | GPC-(GPP)5-GFOGLOGPSGEOGKQGAOGASGDRGPO-(GPP)5-GPC-NH2 | 5551 | 85 |
| 46 | GPC-(GPP)5-GASGDRGPOGPVGPOGLTGPAGEOGRE-(GPP)5-GPC-NH2 | 5514 | 86 |
| 47 | GPC-(GPP)5-GPAGEOGREGSOGADGPOGRDGAAGVK-(GPP)5-GPC-NH2 | 5491 | 87 |
| 48 | GPC-(GPP)5-GRDGAAGVKGDRGETGAVGAOGAOGPO-(GPP)5-GPC-NH2 | 5449 | 88 |
| 49 | GPC-(GPP)5-GAOGAOGPOGSOGPAGPTGKQGDRGEA-(GPP)5-GPC-NH2 | 5431 | 89 |

TABLE 1-continued

| # | Peptide Sequence | Mass (Da) | SEQ ID NO: |
|---|---|---|---|
| 50 | GPC-(GPP)5-GKQGDRGEAGAQGPMGPSGPAGARGIQ-(GPP)5-GPC-NH2 | 5534 | 90 |
| 51 | GPC-(GPP)5-GPAGARGIQGPQGPRGDKGEAGEOGER-(GPP)5-GPC-NH2 | 5644 | 91 |
| 52 | GPC-(GPP)5-GEAGEOGERGLKGHRGFTGLQGLOGPO-(GPP)5-GPC-NH2 | 5746 | 92 |
| 53 | GPC-(GPP)5-GLQGLOGPOGPSGDQGASGPAGPSGPR-(GPP)5-GPC-NH2 | 5427 | 93 |
| 54 | GPC-(GPP)5-GPAGPSGPRGPOGPVGPSGKDGANGIO-(GPP)5-GPC-NH2 | 5409 | 94 |
| 55 | GPC-(GPP)5-GKDGANGIOGPIGPOGPRGRSGETGPA-(GPP)5-GPC-NH2 | 5528 | 95 |
| 56 | GPC-(GPP)5-GPRGRSGETGPAGPOGNOGPOGPOGPO-(GPP)5-GPC-NH2 | 5521 | 96 |

TABLE 2

| # | Peptide Sequence | Mass (Da) | Melting Temp(° C.) | SEQ ID NO: |
|---|---|---|---|---|
| 1 | GPC(GPP)$_5$-GLAGYOGPAGPOGPOGPOGTSGHOGSO-(GPP)$_5$GPC-NH$_2$ | 5456 | 41.90 | 97 |
| 2 | GPC(GPP)$_5$-GTSGHOGSOGSOGYQGPOGEOGQAGPS-(GPP)$_5$GPC-NH$_2$ | 5524 | 35.20 | 98 |
| 3 | GPC(GPP)$_5$-GEOGQAGPSGPOGPOGAIGPSGPAGKD-(GPP)$_5$GPC-NH$_2$ | 5383 | 45.80 | 99 |
| 4 | GPC(GPP)$_5$-GPSGPAGKDGESGROGROGERGLOGPO-(GPP)$_5$GPC-NH$_2$ | 5634 | 43.50 | 100 |
| 5 | GPC(GPP)$_5$-GERGLOGPOGIKGPAGIOGFOGMKGHR-(GPP)$_5$GPC-NH$_2$ | 5728 | 36.50 | 101 |
| 6 | GPC(GPP)$_5$-GFOGMKGHRGFDGRNGEKGETGAOGLK-(GPP)$_5$GPC-NH$_2$ | 5816 | / | 102 |
| 7 | GPC(GPP)$_5$-GETGAOGLKGENGLOGENGAOGPMGPR-(GPP)$_5$GPC-NH$_2$ | 5592 | 43.00 | 103 |
| 8 | GPC(GPP)$_5$-GAOGPMGPRGAOGERGROGLOGAAGAR-(GPP)$_5$GPC-NH$_2$ | 5558 | 48.60 | 104 |
| 9 | GPC(GPP)$_5$-GLOGAAGARGNDGARGSDGQOGPOGPO-(GPP)$_5$GPC-NH$_2$ | 5474 | 38.80 | 105 |
| 10 | GPC(GPP)$_5$-GQOGPOGPOGTAGFOGSOGAKGEVGPA-(GPP)$_5$GPC-NH$_2$ | 5448 | 45.70 | 106 |
| 11 | GPC(GPP)$_5$-GAKGEVGPAGSOGSNGAOGQRGEOGPQ-(GPP)$_5$GPC-NH$_2$ | 5491 | 35.50 | 107 |
| 12 | GPC(GPP)$_5$-GQRGEOGPQGHAGAQGPOGPOGINGSO-(GPP)$_5$GPC-NH$_2$ | 5565 | 45.50 | 108 |
| 13 | GPC(GPP)$_5$-GPOGINGSOGGKGEMGPAGIOGAOGLM-(GPP)$_5$GPC-NH$_2$ | 5464 | 41.50 | 109 |
| 14 | GPC(GPP)$_5$-GIOGAOGLMGARGPOGPAGANGAOGLR-(GPP)$_5$GPC-NH$_2$ | 5457 | 44.50 | 110 |
| 15 | GPC(GPP)$_5$-GANGAOGLRGGAGEOGKNGAKGEOGPR-(GPP)$_5$GPC-NH$_2$ | 5504 | 38.57 | 111 |
| 16 | GPC(GPP)$_5$-GAKGEOGPRGERGEAGIOGVOGAKGED-(GPP)$_5$GPC-NH$_2$ | 5620 | 39.00 | 112 |
| 17 | GPC(GPP)$_5$-GVOGAKGEDGKDGSOGEOGANGLOGAA-(GPP)$_5$GPC-NH$_2$ | 5453 | 38.50 | 113 |
| 18 | GPC(GPP)$_5$-GANGLOGAAGERGAOGFRGPAGPNGIO-(GPP)$_5$GPC-NH$_2$ | 5490 | 37.00 | 114 |
| 19 | GPC(GPP)$_5$-GPAGPNGIOGEKGPAGERGAOGPAGPR-(GPP)$_5$GPC-NH$_2$ | 5480 | 45.00 | 115 |
| 20 | GPC(GPP)$_5$-GAOGPAGPRGAAGEOGRDGVOGGOGMR-(GPP)$_5$GPC-NH$_2$ | 5489 | 43.00 | 116 |
| 21 | GPC(GPP)$_5$-GVOGGOGMRGMOGSOGGOGSDGKOGPO-(GPP)$_5$GPC-NH$_2$ | 5496 | 41.00 | 117 |
| 22 | GPC(GPP)$_5$-GSDGKOGPOGSQGESGROGPOGPSGPR-(GPP)$_5$GPC-NH$_2$ | 5560 | 41.00 | 118 |
| 23 | GPC(GPP)$_5$-GPOGPSGPRGQOGVMGFOGPKGNDGAO-(GPP)$_5$GPC-NH$_2$ | 5576 | 46.10 | 119 |
| 24 | GPC(GPP)$_5$-GPKGNDGAOGKNGERGGOGGOGPQGPO-(GPP)$_5$GPC-NH$_2$ | 5500 | 38.80 | 120 |
| 25 | GPC(GPP)$_5$-GGOGPQGPOGKNGETGPQGPOGPTGPG-(GPP)$_5$GPC-NH$_2$ | 5424 | 49.00 | 121 |
| 26 | GPC(GPP)$_5$-GPOGPTGPGGDKGDTGPOGPQGLQGLO-(GPP)$_5$GPC-NH$_2$ | 5483 | 39.00 | 122 |
| 27 | GPC(GPP)$_5$-GPQGLQGLOGTGGPOGENGKOGEOGPK-(GPP)$_5$GPC-NH$_2$ | 5571 | 44.00 | 123 |

TABLE 2-continued

| # | Peptide Sequence | Mass (Da) | Melting Temp(° C.) | SEQ ID NO: |
|---|---|---|---|---|
| 28 | GPC(GPP)$_5$-GKOGEOGPKGDAGAOGAOGGKGDAGAO-(GPP)$_5$GPC-NH$_2$ | 5376 | 44.49 | 124 |
| 29 | GPC(GPP)$_5$-GGKGDAGAOGERGPOGLAGAOGLRGGA-(GPP)$_5$GPC-NH$_2$ | 5375 | 45.40 | 125 |
| 30 | GPC(GPP)$_5$-GAOGLRGGAGPOGPEGGKGAAGPOGPO-(GPP)$_5$GPC-NH$_2$ | 5324 | 42.90 | 126 |
| 31 | GPC(GPP)$_5$-GAAGPOGPOGAAGTOGLQGMOGERGGL-(GPP)$_5$GPC-NH$_2$ | 5418 | 46.30 | 127 |
| 32 | GPC(GPP)$_5$-GMOGERGGLGSOGPKGDKGEOGGOGAD-(GPP)$_5$GPC-NH$_2$ | 5525 | 43.20 | 128 |
| 33 | GPC(GPP)$_5$-GEOGGOGADGVOGKDGPRGPTGPIGPO-(GPP)$_5$GPC-NH$_2$ | 5484 | 38.83 | 129 |
| 34 | GPC(GPP)$_5$-GPTGPIGPOGPAGQOGDKGEGGAOGLO-(GPP)$_5$GPC-NH$_2$ | 5426 | 46.27 | 130 |
| 35 | GPC(GPP)$_5$-GEGGAOGLOGIAGPRGSOGERGETGPO-(GPP)$_5$GPC-NH$_2$ | 5518 | 41.00 | 131 |
| 36 | GPC(GPP)$_5$-GERGETGPOGPAGFOGAOGQNGEOGGK-(GPP)$_5$GPC-NH$_2$ | 5566 | 40.93 | 132 |
| 37 | GPC(GPP)$_5$-GQNGEOGGKGERGAOGEKGEGGPOGVA-(GPP)$_5$GPC-NH$_2$ | 5521 | 30.79 | 133 |
| 38 | GPC(GPP)$_5$-GEGGPOGVAGPOGGSGPAGPOGPQGVK-(GPP)$_5$GPC-NH$_2$ | 5310 | 42.00 | 134 |
| 39 | GPC(GPP)$_5$-GPOGPQGVKGERGSOGGOGAAGFOGAR-(GPP)$_5$GPC-NH$_2$ | 5506 | 41.70 | 135 |
| 40 | GPC(GPP)$_5$-GAAGFOGARGLOGPOGSNGNOGPOGPS-(GPP)$_5$GPC-NH$_2$ | 5447 | 42.70 | 136 |
| 41 | GPC(GPP)$_5$-GNOGPOGPSGSOGKDGPOGPAGNTGAO-(GPP)$_5$GPC-NH$_2$ | 5400 | 46.00 | 137 |
| 42 | GPC(GPP)$_5$-GPAGNTGAOGSOGVSGPKGDAGQOGEK-(GPP)$_5$GPC-NH$_2$ | 5422 | 37.00 | 138 |
| 43 | GPC(GPP)$_5$-GDAGQOGEKGSOGAQGPOGAOGPLGIA-(GPP)$_5$GPC-NH$_2$ | 5431 | 35.80 | 139 |
| 44 | GPC(GPP)$_5$-GAOGPLGIAGITGARGLAGPOGMOGPR-(GPP)$_5$GPC-NH$_2$ | 5470 | 35.90 | 140 |
| 45 | GPC(GPP)$_5$-GPOGMOGPRGSOGPQGVKGESGKOGAN-(GPP)$_5$GPC-NH$_2$ | 5561 | 46.70 | 141 |
| 46 | GPC(GPP)$_5$-GESGKOGANGLSGERGPOGPQGLOGLA-(GPP)$_5$GPC-NH$_2$ | 5532 | 34.90 | 142 |
| 47 | GPC(GPP)$_5$-GPQGLOGLAGTAGEOGRDGNOGSDGLO-(GPP)$_5$GPC-NH$_2$ | 5535 | 35.92 | 143 |
| 48 | GPC(GPP)$_5$-GNOGSDGLOGRDGSOGGKGDRGENGSO-(GPP)$_5$GPC-NH$_2$ | 5585 | 33.09 | 144 |
| 49 | GPC(GPP)$_5$-GDRGENGSOGAOGAOGHOGPOGPVGPA-(GPP)$_5$GPC-NH$_2$ | 5466 | 43.50 | 145 |
| 50 | GPC(GPP)$_5$-GPOGPVGPAGKSGDRGESGPAGPAGAO-(GPP)$_5$GPC-NH$_2$ | 5356 | 43.45 | 146 |
| 51 | GPC(GPP)$_5$-GPAGPAGAOGPAGSRGAOGPQGPRGDK-(GPP)$_5$GPC-NH$_2$ | 5396 | 49.10 | 147 |
| 52 | GPC(GPP)$_5$-GPQGPRGDKGETGERGAAGIKGHRGFO-(GPP)$_5$GPC-NH$_2$ | 5732 | / | 148 |
| 53 | GPC(GPP)$_5$-GIKGHRGFOGNOGAOGSOGPAGQQGAI-(GPP)$_5$GPC-NH$_2$ | 5573 | 30.47 | 149 |
| 54 | GPC(GPP)$_5$-GPAGQQGAIGSOGPAGPRGPVGPSGPO-(GPP)$_5$GPC-NH$_2$ | 5379 | 47.50 | 150 |
| 55 | GPC(GPP)$_5$-GPVGPSGPOGKDGTSGHOGPIGPOGPR-(GPP)$_5$GPC-NH$_2$ | 5504 | 49.10 | 151 |
| 56 | GPC(GPP)$_5$-GPIGPOGPRGNRGERGSEGSOGHOGQO-(GPP)$_5$GPC-NH$_2$ | 5695 | 44.10 | 152 |
| 57 | GPC(GPP)$_5$-GERGSEGSOGHOGQOGPOGPOGAOGPC-(GPP)$_5$GPC-NH$_2$ | 5556 | 44.10 | 153 |
| GPP10 | GPC(GPP)$_{10}$GPC-NH$_2$ | 3044 | 48.2 | 154 |

TABLE 3

| Code | Peptide Sequence | Mass (Da) | SEQ ID NO: |
|---|---|---|---|
| GAOGPAGEAinGPP | GPC(GPP)5GAOGPAGEA(GPP)5GPC-NH2 | 3768 | 155 |
| GKOGPAGFAinGPP | GPC(GPP)5GKOGPAGFA(GPP)5GPC-NH2 | 3843 | 156 |
| GAOGVMGFAinGPP | GPC(GPP)5GAOGVMGFA(GPP)5GPC-NH2 | 3848 | 157 |
| GLOGPSGEOinGPP | GPC(GPP)5GLOGPSGEO(GPP)5GPC-NH2 | 3868 | 158 |

TABLE 3-continued

| Code | Peptide Sequence | Mass (Da) | SEQ ID NO: |
|---|---|---|---|
| GFOGLOGPSinGPP | GPC(GPP)5GFOGLOGPS(GPP)5GPC-NH2 | 3886 | 159 |
| GAOGPAGFAGEAinGPP | GPC(GPP)5GAOGPAGFAGEA(GPP)5GPC-NH2 | 4043 | 160 |
| GFOGPAGFAinGPP | GPC(GPP)5GFOGPAGFA(GPP)5GPC-NH2 | 3862 | 161 |
| ColIII-36GPOtoGAO | GPC(GPP)5-GPOGPAGFOGAO-(GPP)5GPC-NH2 | 4095.67 | 162 |
| ColIII-36GPOtoGAO-A2 | GPC(GPP)5-GAOGPAGFOGAO-(GPP)5GPC-NH2 | 4069.63 | 163 |
| ColIII-36GPOtoGAO-A9 | GPC(GPP)5-GPOGPAGFAGAO-(GPP)5GPC-NH2 | 4053.63 | 164 |
| GAOGPAGSAinGPP | GPC(GPP)5GAOGPAGSA(GPP)5GPC-NH2 | 3726 | 165 |
| ColIII-36GERtoGQN | GPC(GPP)5-GERGETGPOGPAGFOGAOGQN-(GPP)5GPC-NH2 | 5024 | 166 |
| ColIII-36GPOtoGGk | GPC(GPP)5-GPOGPAGFOGAOGQNGEOGGK-(GPP)5GPC-NH2 | 4936 | 167 |
| ColIII-36GPOtoGAO-A5 | GPC(GPP)5-GPOGAAGFOGAO-(GPP)5GPC-NH2 | 4069 | 168 |
| ColIII-36GPOtoGAO-A8 | GPC(GPP)5-GPOGPAGAOGAO-(GPP)5GPC-NH2 | 4019 | 169 |
| ColIII-36GPOtoGAO-A12 | GPC(GPP)5-GPOGPAGFOGAA-(GPP)5GPC-NH2 | 4053 | 170 |
| GAOGPAGFAinGPP | GPC(GPP)-5GAOGPAGFA-(GPP)5GPC-NH2 | 3786 | 171 |
| GAOGAAGFAinGPP | GPC(GPP)5GAOGAAGFA(GPP)5GPC-NH2 | 3760 | 172 |
| GAOGPPGFAinGPP | GPC(GPP)5GAOGPPGFA(GPP)5GPC-NH2 | 3812 | 173 |
| GAOGPOGFAinGPP | GPC(GPP)5GAOGPOGFA(GPP)5GPC-NH2 | 3828 | 174 |
| GAOGPAGFDinGPP | GPC(GPP)5GAOGPAGFD(GPP)5GPC-NH2 | 3754 | 175 |
| GQOGPAGFAinGPP | GPC(GPP)5GQOGPAGFA(GPP)5GPC-NH2 | 3843 | 176 |
| GEOGPAGFAinGPP | GPC(GPP)5GEOGPAGFA(GPP)5GPC-NH2 | 3844 | 177 |
| GAOGPQGFAinGPP | GPC(GPP)5GAOGPQGFA(GPP)5GPC-NH2 | 3843 | 178 |
| GAOGPQGPAinGPP | GPC(GPP)5GAOGQAGPA(GPP)5GPC-NH2 | 3793 | 179 |
| GAOGASGDRinGPP | GPC(GPP)5GAOGASGDR(GPP)5GPC-NH2 | 3829 | 180 |
| GAOGPAGYAinGPP | GPC(GPP)5GAOGPAGYA(GPP)5GPC-NH2 | 3802 | 181 |
| GPP10 | GPC-(GPP)10-GPCG-NH2 | 3044 | 154 |

TABLE 4

Highest affinity Toolkit peptides:

| | | |
|---|---|---|
| II-1 | GPMGPMGPRGPOGPAGAOGPQGFQGNO | (SEQ ID NO: 197) |
| II-26 | GERGEQGAOGPSGFQGLOGPOGPOGEG | (SEQ ID NO: 198) |
| II-35 | GSAGARGAOGERGETGPOGPAGFAGPO | (SEQ ID NO: 199) |
| II-45 | GFOGLOGPSGEOGKQGAOGASGDRGPO | (SEQ ID NO: 200) |
| III-36 | GERGETGPOGPAGFOGAOGQNGEOGGK | (SEQ ID NO: 201) |
| III-39 | GPOGPQGVKGERGSOGGOGAAGFOGAR | (SEQ ID NO: 202) |
| Consensus: | GxOGPxGFOGxO | (SEQ ID NO: 203) |

TABLE 5

Minimum motif and OSCAR-binding variants:

```
              GAOGPAGFA (SEQ ID NO: 204)

P   AS DR

G       SO

YQ
```

References:
Walsh, M. C. et al. Annu Rev Immunol 24, 33 (2006)
Takayanagi, H. et al Nat Rev Immunol 7 (4), 292 (2007).
Mundy, G. R., Osteoporosis and inflammation. Nutr Rev 65 (12 Pt 2), S147 (2007);
Teitelbaum, S. L. Arthritis Res Ther 8 (1), 201 (2006);
Wada, T. et al. Trends Mol Med 12 (1), 17 (2006).
Eriksen, E. F. et al J Bone Miner Res 22 (1), 1 (2007).
Hauge, E. M. et al. J Bone Miner Res 16 (9), 1575 (2001).
Matsuo, K. et al Arch Biochem Biophys 473 (2), 201 (2008);
Parfitt, A. M. J Bone Miner Res 16 (9), 1583 (2001).
Lacey, D. L. et al. Cell 93 (2), 165 (1998); Yasuda, H. et al. Proc Natl Acad Sci USA 95 (7), 3597 (1998);
Kong, Y. Y. et al. Nature 397 (6717), 315 (1999).
Hamdy, N. A. Curr Opin Investig Drugs 8 (4), 299 (2007);
Roodman, G. D et al. Cancer Treat Rev 34 (1), 92 (2008).
Boyle, W. J. et al Nature 423 (6937), 337 (2003).
Koga, T. et al. Nature 428 (6984), 758 (2004).
Mocsai, A. et al. Proc Natl Acad Sci USA 101 (16), 6158 (2004);
Zou, W. et al. J Cell Biol 176 (6), 877 (2007).
Bouchon, A. et al J Exp Med 194 (8), 1111 (2001).
Kondo, T. et al. Neurology 59 (7), 1105 (2002);
Paloneva, J. et al Nat Genet 25 (3), 357 (2000); Paloneva, J. et al. Am J Hum Genet 71 (3), 656 (2002).
Cella, M. et al. J Exp Med 198 (4), 645 (2003)
Humphrey, M. B. et al. J Bone Miner Res 19 (2), 224 (2004)
Paloneva, J. et al. J Exp Med 198 (4), 669 (2003).
Takegahara, N. et al. Nat Cell Biol 8 (6), 615 (2006).
Kim, N. et al. J Exp Med 195 (2), 201 (2002).
Kim, Y. et al. J Biol Chem 280 (38), 32905 (2005).
Masuyama, R. et al. J Clin Invest 116 (12), 3150 (2006)
Usui, M. et al. J Bone Miner Res 23 (3), 314 (2008).
Ishikawa, S. et al. Int Immunol 16 (7), 1019 (2004).
Merck, E. et al. Blood 104 (5), 1386 (2004).
Kim, G. S. et al. J Bone Miner Res 20 (8), 1342 (2005).
Merck, E. et al. Blood 105 (9), 3623 (2005);
Merck, E. et al. J Immunol 176 (5), 3149 (2006).
Nesbitt S A, et al Science. 276(5310):266-9 (1997).
Stenbeck G, et al. J Cell Sci. 117(Pt 6):827-36 (2004).
Lorenzo J, et al. Endocr Rev. 29(4):403-40 (2008).
Raynal N, et al. J Biol Chem. 281(7):3821-31 (2006).
Arase H, et al Science. 296(5571):1323-6 (2002).
Slatter D A et al J Mol Biol. 359(2):289-98 (2006).

Sequences (SEQ ID NO: 196)

MVLLLILQLSTLCELSLPWPVCHADFTSPVPLASYPKPWLGAHPAAIVTPG
INVTLICRAPQPAWGFGLFKTGLATPLLLRNVSIGLAEFFLEKVTSVQEGS
YHCRYRKTDWGPGVWSQPSNALELLVTDQLPRPSLVAIPGPVVAPETTVSL
RCAGRIPGMSFALYRADVATPLQYIDSVQPWADFLLNSANAPGTYYCYYHT
PSSPYVLSERSQPLVISSEGSGSLDYTQGNLVRLGLAGLVLICLGIIVTFD
WHSRRSAFVRLLPQQNWV

OSCAR Hattus Norvegicus
From Bat Genome databae (http://rgd.mcw.edu/) weblink to Rat OSCAR (predicted):
http://rgd.mcw.edu/tools/genes/genes view.cgi?id=1559897
Ensembl (www.ensembl.org) Gene ID: ENSRNOG00000036776.

The invention claimed is:

1. An isolated collagen peptide for modulating differentiation and/or activation of an osteoclast-associated receptor (OSCAR) expressing cell, the collagen peptide comprising the amino acid sequence:

$GX_1OGPX_3GFOGX_6O$ (SEQ ID NO.14), wherein, $X_1$ is independently A, P or G, $X_3$ is independently A, M, P, O, Q, or S, $X_6$ is independently A, P or L, and O is a hydroxyproline residue, and wherein said amino acid sequence is fused directly at its N-terminus and C-terminus to a triple helical sequence selected from the group consisting of: $(GPP)_n$, where $n$ is 2-6, and $(GPO)_{n1}$, where $n1$ is 2-6.

2. The isolated collagen peptide according to claim 1 wherein the collagen peptide is conjugated to a coupling partner.

3. An isolated peptidyl trimer comprising the collagen peptide according to claim 1, wherein the peptidyl trimer comprises a homotrimer or a heterotrimer.

4. The isolated peptidyl trimer according to claim 3, wherein the collagen peptide in the trimer is cross-linked to another collagen peptide in the trimer.

5. The isolated collagen peptide of claim 1, comprising SEQ ID. NO:5.

6. The isolated collagen peptide of claim 1, wherein the triple helical sequence further comprises a GPC sequence, such that the triple helical sequence fused at the N-terminus is selected from the group consisting of $GPC(GPP)_n$ and $GPC(GPO)_{n1}$, and the triple helical sequence fused at the C-terminus is selected from the group consisting of $(GPP)_nGPC$ and $(GPO)_{n1}GPC$, where $n$ is 2-6, and $n1$ is 2-6.

7. The isolated collagen peptide of claim 6, comprising SEQ ID NO:224.

* * * * *

UNITED STATES PATENT AND TRADEMARK OFFICE
CERTIFICATE OF CORRECTION

| | | |
|---|---|---|
| PATENT NO. | : 8,642,728 B2 | Page 1 of 1 |
| APPLICATION NO. | : 13/122637 | |
| DATED | : February 4, 2014 | |
| INVENTOR(S) | : John Trowsdale et al. | |

It is certified that error appears in the above-identified patent and that said Letters Patent is hereby corrected as shown below:

On the Title Page, Item (57) in the Abstract:

At last line (line number 9): "OS-CAR" should read --OSCAR--.

Signed and Sealed this
Second Day of September, 2014

Michelle K. Lee
*Deputy Director of the United States Patent and Trademark Office*

SEQUENCE LISTING

```
<160> NUMBER OF SEQ ID NOS: 225

<210> SEQ ID NO 1
<211> LENGTH: 6
<212> TYPE: PRT
<213> ORGANISM: Artificial sequence
<220> FEATURE:
<223> OTHER INFORMATION: Synthetic sequence: Integrin alpha-2-beta-1
      homotrimeric peptide ligand
<220> FEATURE:
<221> NAME/KEY: MOD_RES
<222> LOCATION: (3)..(3)
<223> OTHER INFORMATION: 4Hyp

<400> SEQUENCE: 1

Gly Phe Pro Gly Glu Arg
1               5

<210> SEQ ID NO 2
<211> LENGTH: 30
<212> TYPE: PRT
<213> ORGANISM: Artificial sequence
<220> FEATURE:
```

```
<223> OTHER INFORMATION: Synthetic sequence: Triple-helical peptide used
      as a negative control

<400> SEQUENCE: 2

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30

<210> SEQ ID NO 3
<211> LENGTH: 15
<212> TYPE: PRT
<213> ORGANISM: Artificial sequence
<220> FEATURE:
<223> OTHER INFORMATION: Synthetic sequence

<400> SEQUENCE: 3

Gly Pro Pro Gly Pro Pro Gly Pro Pro Gly Pro Pro Gly Pro Pro
1               5                   10                  15

<210> SEQ ID NO 4
<211> LENGTH: 39
<212> TYPE: PRT
<213> ORGANISM: Artificial sequence
<220> FEATURE:
<223> OTHER INFORMATION: Synthetic sequence: N- and C- terminal bound
      (GPP)5 triple-helical peptide
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 4

Gly Pro Pro Gly Pro Pro Gly Pro Pro Gly Pro Pro Gly Pro Pro Gly
1               5                   10                  15

Leu Pro Gly Pro Ser Gly Glu Pro Gly Pro Pro Gly Pro Pro Gly Pro
            20                  25                  30

Pro Gly Pro Pro Gly Pro Pro
        35

<210> SEQ ID NO 5
<211> LENGTH: 42
<212> TYPE: PRT
<213> ORGANISM: Artificial sequence
<220> FEATURE:
<223> OTHER INFORMATION: Synthetic sequence: N- and C- terminal bound
      (GPP)5 triple-helical peptide
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 5

Gly Pro Pro Gly Pro Pro Gly Pro Pro Gly Pro Pro Gly Pro Pro Gly
1               5                   10                  15

Pro Pro Gly Pro Ala Gly Phe Pro Gly Ala Pro Gly Pro Pro Gly Pro
            20                  25                  30
```

```
Pro Gly Pro Pro Gly Pro Pro Gly Pro Pro
        35                  40

<210> SEQ ID NO 6
<211> LENGTH: 39
<212> TYPE: PRT
<213> ORGANISM: Artificial sequence
<220> FEATURE:
<223> OTHER INFORMATION: Synthetic sequence: N- and C- terminal bound
      (GPP)5 triple-helical peptide NR325
<220> FEATURE:
<221> NAME/KEY: MOD_RES
<222> LOCATION: (18)..(18)
<223> OTHER INFORMATION: 4Hyp

<400> SEQUENCE: 6

Gly Pro Pro Gly Pro Pro Gly Pro Pro Gly Pro Pro Gly Pro Pro Gly
1               5                   10                  15

Ala Pro Gly Pro Ala Gly Phe Ala Gly Pro Pro Gly Pro Pro Gly Pro
            20                  25                  30

Pro Gly Pro Pro Gly Pro Pro
        35

<210> SEQ ID NO 7
<211> LENGTH: 39
<212> TYPE: PRT
<213> ORGANISM: Artificial sequence
<220> FEATURE:
<223> OTHER INFORMATION: Synthetic sequence: Triple-helical peptide DB99
<220> FEATURE:
<221> NAME/KEY: MOD_RES
<222> LOCATION: (18)..(18)
<223> OTHER INFORMATION: 4Hyp

<400> SEQUENCE: 7

Gly Pro Pro Gly Pro Pro Gly Pro Pro Gly Pro Pro Gly Pro Pro Gly
1               5                   10                  15

Ala Pro Gly Pro Ala Gly Ser Ala Gly Pro Pro Gly Pro Pro Gly Pro
            20                  25                  30

Pro Gly Pro Pro Gly Pro Pro
        35

<210> SEQ ID NO 8
<211> LENGTH: 39
<212> TYPE: PRT
<213> ORGANISM: Artificial sequence
<220> FEATURE:
<223> OTHER INFORMATION: Synthetic sequence: Triple-helical peptide
      NR338
<220> FEATURE:
<221> NAME/KEY: MOD_RES
<222> LOCATION: (18)..(18)
<223> OTHER INFORMATION: 4Hyp

<400> SEQUENCE: 8

Gly Pro Pro Gly Pro Pro Gly Pro Pro Gly Pro Pro Gly Pro Pro Gly
1               5                   10                  15

Ala Pro Gly Ala Ser Gly Asp Arg Gly Pro Pro Gly Pro Pro Gly Pro
            20                  25                  30

Pro Gly Pro Pro Gly Pro Pro
        35

<210> SEQ ID NO 9
<211> LENGTH: 39
<212> TYPE: PRT
<213> ORGANISM: Artificial sequence
```

```
<220> FEATURE:
<223> OTHER INFORMATION: Synthetic sequence: Triple-helical peptide
      NR340
<220> FEATURE:
<221> NAME/KEY: MOD_RES
<222> LOCATION: (18)..(18)
<223> OTHER INFORMATION: 4Hyp

<400> SEQUENCE: 9

Gly Pro Pro Gly Pro Pro Gly Pro Pro Gly Pro Pro Gly Pro Pro Gly
1               5                   10                  15

Ala Pro Gly Pro Ala Gly Tyr Ala Gly Pro Pro Gly Pro Pro Gly Pro
            20                  25                  30

Pro Gly Pro Pro Gly Pro Pro
            35

<210> SEQ ID NO 10
<211> LENGTH: 9
<212> TYPE: PRT
<213> ORGANISM: Artificial sequence
<220> FEATURE:
<223> OTHER INFORMATION: Synthetic sequence: Minimal OSCAR-binding
      sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp

<400> SEQUENCE: 10

Gly Pro Pro Gly Pro Ala Gly Phe Pro
1               5

<210> SEQ ID NO 11
<211> LENGTH: 39
<212> TYPE: PRT
<213> ORGANISM: Artificial sequence
<220> FEATURE:
<223> OTHER INFORMATION: Synthetic sequence: triple-helical peptide
      designed to the minimal OSCAR-binding sequence
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 11

Gly Pro Pro Gly Pro Pro Gly Pro Pro Gly Pro Pro Gly Pro Pro Gly
1               5                   10                  15

Pro Pro Gly Pro Ala Gly Phe Pro Gly Pro Pro Gly Pro Pro Gly Pro
            20                  25                  30

Pro Gly Pro Pro Gly Pro Pro
            35

<210> SEQ ID NO 12
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: VARIANT
<222> LOCATION: (2)..(2)
<223> OTHER INFORMATION: Xaa is independently any non-polar amino acid
```

-continued

```
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (5)..(5)
<223> OTHER INFORMATION: Xaa is independently Pro, Ala, or Val
<220> FEATURE:
<221> NAME/KEY: VARIANT
<222> LOCATION: (6)..(6)
<223> OTHER INFORMATION: Xaa is independently any amino acid
<220> FEATURE:
<221> NAME/KEY: VARIANT
<222> LOCATION: (8)..(8)
<223> OTHER INFORMATION: Xaa is independently Phe, Ser, Asp, Tyr, Ala or
      Glu
<220> FEATURE:
<221> NAME/KEY: VARIANT
<222> LOCATION: (9)..(9)
<223> OTHER INFORMATION: Xaa is independently any amino acid

<400> SEQUENCE: 12

Gly Xaa Pro Gly Xaa Xaa Gly Xaa Xaa
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: VARIANT
<222> LOCATION: (2)..(2)
<223> OTHER INFORMATION: Xaa is independently any non-polar amino acid
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (6)..(6)
<223> OTHER INFORMATION: Xaa is independently any amino acid
<220> FEATURE:
<221> NAME/KEY: MOD_RES
<222> LOCATION: (9)..(9)
<223> OTHER INFORMATION: 4Hyp

<400> SEQUENCE: 13

Gly Xaa Pro Gly Pro Xaa Gly Phe Pro
1               5

<210> SEQ ID NO 14
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: VARIANT
<222> LOCATION: (2)..(2)
<223> OTHER INFORMATION: Xaa is independently any non-polar amino acid;
      in some embodiments Xaa is independently Ala, Pro or Gly,
      preferably Pro or Ala, more preferably Ala
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (6)..(6)
<223> OTHER INFORMATION: Xaa is independently any amino acid; in some
      embodiments Xaa is independently Ala, Met, Pro, hydroxyproline,
      Gln, or Ser; more preferably Ala or Ser
<220> FEATURE:
```

```
<221> NAME/KEY: MOD_RES
<222> LOCATION: (9)..(9)
<223> OTHER INFORMATION: 4Hyp
<220> FEATURE:
<221> NAME/KEY: VARIANT
<222> LOCATION: (11)..(11)
<223> OTHER INFORMATION: Xaa is independently Ala, Pro, Leu or Ala
<220> FEATURE:
<221> NAME/KEY: MOD_RES
<222> LOCATION: (12)..(12)
<223> OTHER INFORMATION: 4Hyp

<400> SEQUENCE: 14

Gly Xaa Pro Gly Pro Xaa Gly Phe Pro Gly Xaa Pro
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp

<400> SEQUENCE: 15

Gly Pro Pro Gly Pro Ala Gly Phe Pro Gly Ala Pro
1               5                   10

<210> SEQ ID NO 16
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 16

Gly Ala Pro Gly Pro Ala Gly Phe Ala
1               5

<210> SEQ ID NO 17
<211> LENGTH: 21
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp

<400> SEQUENCE: 17
```

```
Gly Glu Arg Gly Glu Thr Gly Pro Pro Gly Pro Ala Gly Phe Pro Gly
1               5                   10                  15

Ala Pro Gly Gln Asn
            20

<210> SEQ ID NO 18
<211> LENGTH: 21
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (18)..(18)
<223> OTHER INFORMATION: 4Hyp

<400> SEQUENCE: 18

Gly Pro Pro Gly Pro Ala Gly Phe Pro Gly Ala Pro Gly Gln Asn Gly
1               5                   10                  15

Glu Pro Gly Gly Lys
            20

<210> SEQ ID NO 19
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp

<400> SEQUENCE: 19

Gly Ala Pro Gly Pro Ala Gly Phe Pro Gly Ala Pro
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
```

```
<221> NAME/KEY: MOD_RES
<222> LOCATION: (12)..(12)
<223> OTHER INFORMATION: 4Hyp

<400> SEQUENCE: 20

Gly Pro Pro Gly Ala Ala Gly Phe Pro Gly Ala Pro
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (12)..(12)
<223> OTHER INFORMATION: 4Hyp

<400> SEQUENCE: 21

Gly Pro Pro Gly Pro Ala Gly Phe Ala Gly Ala Pro
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp

<400> SEQUENCE: 22

Gly Pro Pro Gly Pro Ala Gly Phe Pro Gly Ala Ala
1               5                   10

<210> SEQ ID NO 23
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 23

Gly Ala Pro Gly Pro Ala Gly Ser Ala
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
```

```
<400> SEQUENCE: 24

Gly Ala Pro Gly Val Met Gly Phe Ala
1               5

<210> SEQ ID NO 25
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 25

Gly Ala Pro Gly Pro Ala Gly Phe Ala Gly Glu Ala
1               5                   10

<210> SEQ ID NO 26
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 26

Gly Ala Pro Gly Ala Ala Gly Phe Ala
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 27

Gly Ala Pro Gly Pro Pro Gly Phe Ala
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp

<400> SEQUENCE: 28

Gly Ala Pro Gly Pro Pro Gly Phe Ala
1               5

<210> SEQ ID NO 29
<211> LENGTH: 9
```

```
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 29

Gly Ala Pro Gly Pro Gln Gly Phe Ala
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 30

Gly Ala Pro Gly Ala Ser Gly Asp Arg
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 31

Gly Ala Pro Gly Pro Ala Gly Tyr Ala
1               5

<210> SEQ ID NO 32
<211> LENGTH: 12
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: 4Hyp

<400> SEQUENCE: 32

Gly Pro Pro Gly Pro Ala Gly Ala Pro Gly Ala Pro
1               5                   10

<210> SEQ ID NO 33
<211> LENGTH: 9
<212> TYPE: PRT
<213> ORGANISM: Artificial sequence
<220> FEATURE:
<223> OTHER INFORMATION: Synthetic sequence: Collagen peptide
```

```
<220> FEATURE:
<221> NAME/KEY: MOD_RES
<222> LOCATION: (3)..(3)
<223> OTHER INFORMATION: 4Hyp

<400> SEQUENCE: 33

Gly Ala Pro Gly Pro Ala Gly Glu Ala
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 34

Gly Ala Pro Gly Pro Ala Gly Phe Asp
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: MOD_RES
<222> LOCATION: (3)..(3)
<223> OTHER INFORMATION: 4Hyp

<400> SEQUENCE: 35

Gly Ala Pro Gly Pro Gln Gly Pro Ala
1               5

<210> SEQ ID NO 36
<211> LENGTH: 18
<212> TYPE: PRT
<213> ORGANISM: Artificial sequence
<220> FEATURE:
<223> OTHER INFORMATION: Synthetic sequence: N-terminal sequence

<400> SEQUENCE: 36

Gly Pro Cys Gly Pro Pro Gly Pro Pro Gly Pro Pro Gly Pro Pro Gly
1               5                   10                  15

Pro Pro

<210> SEQ ID NO 37
<211> LENGTH: 18
<212> TYPE: PRT
<213> ORGANISM: Artificial sequence
<220> FEATURE:
<223> OTHER INFORMATION: Synthetic sequence: C-terminal sequence

<400> SEQUENCE: 37

Gly Pro Pro Gly Pro Pro Gly Pro Pro Gly Pro Pro Gly Pro Pro Gly
1               5                   10                  15

Pro Cys

<210> SEQ ID NO 38
<211> LENGTH: 45
<212> TYPE: PRT
<213> ORGANISM: Artificial sequence
<220> FEATURE:
```

```
<223> OTHER INFORMATION: Synthetic sequence: Collagen peptide
<220> FEATURE:
<221> NAME/KEY: MOD_RES
<222> LOCATION: (21)..(21)
<223> OTHER INFORMATION: 4Hyp

<400> SEQUENCE: 38

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 39
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 39
gcagtataac agcaaggtgg                                              20

<210> SEQ ID NO 40
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 40

Gly Pro Cys Gly Pro Pro Gly Pro Pro Gly Pro Pro Gly Pro Pro Gly
1               5                   10                  15

Pro Pro Gly Pro Met Gly Pro Met Gly Pro Arg Gly Pro Pro Gly Pro
            20                  25                  30

Ala Gly Ala Pro Gly Pro Gln Gly Phe Gln Gly Asn Pro Gly Pro Pro
        35                  40                  45

Gly Pro Pro Gly Pro Pro Gly Pro Pro Gly Pro Pro Gly Pro Cys
    50                  55                  60

<210> SEQ ID NO 41
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
```

```
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 41

Gly Pro Cys Gly Pro Pro Gly Pro Pro Gly Pro Pro Gly Pro Pro Gly
1               5                   10                  15

Pro Pro Gly Pro Gln Gly Phe Gln Gly Asn Pro Gly Glu Pro Gly Glu
            20                  25                  30

Pro Gly Val Ser Gly Pro Met Gly Pro Arg Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 42
<211> LENGTH: 63
<212> TYPE: PRT
<213> ORGANISM: Artificial sequence
<220> FEATURE:
<223> OTHER INFORMATION: Synthetic sequence: Sequence of the
      overlapping homotrimeric type-II collagen peptide library
      (collagen II toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 42

Gly Pro Cys Gly Pro Pro Gly Pro Pro Gly Pro Pro Gly Pro Pro Gly
1               5                   10                  15

Pro Pro Gly Pro Met Gly Pro Arg Gly Pro Pro Gly Pro Pro Gly Lys
            20                  25                  30

Pro Gly Asp Asp Gly Glu Ala Gly Lys Pro Gly Lys Ala Gly Pro Pro
        35                  40                  45

Gly Pro Pro Gly Pro Pro Gly Pro Pro Gly Pro Pro Gly Pro Cys
    50                  55                  60

<210> SEQ ID NO 43
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
```

<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 43

Gly Pro Cys Gly Pro Pro Gly Pro Pro Gly Pro Pro Gly Pro Pro Gly
1               5                   10                  15

Pro Pro Gly Glu Ala Gly Lys Pro Gly Lys Ala Gly Glu Arg Gly Pro
            20                  25                  30

Pro Gly Pro Gln Gly Ala Arg Gly Phe Pro Gly Thr Pro Gly Pro Pro
        35                  40                  45

Gly Pro Pro Gly Pro Pro Gly Pro Pro Gly Pro Pro Gly Pro Cys
    50                  55                  60

<210> SEQ ID NO 44
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 44

Gly Pro Cys Gly Pro Pro Gly Pro Pro Gly Pro Pro Gly Pro Pro Gly
1               5                   10                  15

Pro Pro Gly Ala Arg Gly Phe Pro Gly Thr Pro Gly Leu Pro Gly Val
            20                  25                  30

Lys Gly His Arg Gly Tyr Pro Gly Leu Asp Gly Ala Lys Gly Pro Pro
        35                  40                  45

Gly Pro Pro Gly Pro Pro Gly Pro Pro Gly Pro Pro Gly Pro Cys
    50                  55                  60

<210> SEQ ID NO 45
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES -continued

```
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 45

Gly Pro Cys Gly Pro Pro Gly Pro Pro Gly Pro Pro Gly Pro Pro Gly
1               5                   10                  15

Pro Pro Gly Tyr Pro Gly Leu Asp Gly Ala Lys Gly Glu Ala Gly Ala
            20                  25                  30

Pro Gly Val Lys Gly Glu Ser Gly Ser Pro Gly Glu Asn Gly Pro Pro
        35                  40                  45

Gly Pro Pro Gly Pro Pro Gly Pro Pro Gly Pro Pro Gly Pro Cys
    50                  55                  60

<210> SEQ ID NO 46
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 46

Gly Pro Cys Gly Pro Pro Gly Pro Pro Gly Pro Pro Gly Pro Pro Gly
1               5                   10                  15

Pro Pro Gly Glu Ser Gly Ser Pro Gly Glu Asn Gly Ser Pro Gly Pro
            20                  25                  30

Met Gly Pro Arg Gly Leu Pro Gly Glu Arg Gly Arg Thr Gly Pro Pro
        35                  40                  45

Gly Pro Pro Gly Pro Pro Gly Pro Pro Gly Pro Pro Gly Pro Cys
50                  55                  60

<210> SEQ ID NO 47
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 47

Gly Pro Cys Gly Pro Pro Gly Pro Pro Gly Pro Pro Gly Pro Pro Gly
1               5                   10                  15
```

```
Pro Pro Gly Leu Pro Gly Glu Arg Gly Arg Thr Gly Pro Ala Gly Ala
            20                  25                  30

Ala Gly Ala Arg Gly Asn Asp Gly Gln Pro Gly Pro Ala Gly Pro Pro
        35                  40                  45

Gly Pro Pro Gly Pro Pro Gly Pro Pro Gly Pro Pro Gly Pro Cys
    50                  55                  60
```

<210> SEQ ID NO 48
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 48

```
Gly Pro Cys Gly Pro Pro Gly Pro Pro Gly Pro Pro Gly Pro Pro Gly
1               5                   10                  15

Pro Pro Gly Asn Asp Gly Gln Pro Gly Pro Ala Gly Pro Pro Gly Pro
            20                  25                  30

Val Gly Pro Ala Gly Gly Pro Gly Phe Pro Gly Ala Pro Gly Pro Pro
        35                  40                  45

Gly Pro Pro Gly Pro Pro Gly Pro Pro Gly Pro Pro Gly Pro Cys
    50                  55                  60
```

<210> SEQ ID NO 49
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 49

```
Gly Pro Cys Gly Pro Pro Gly Pro Pro Gly Pro Pro Gly Pro Pro Gly
1               5                   10                  15
```

-continued

Pro Pro Gly Gly Pro Gly Phe Pro Gly Ala Pro Gly Ala Lys Gly Glu
                20                  25                  30

Ala Gly Pro Thr Gly Ala Arg Gly Pro Glu Gly Ala Gln Gly Pro Pro
            35                  40                  45

Gly Pro Pro Gly Pro Pro Gly Pro Pro Gly Pro Pro Gly Pro Cys
        50                  55                  60

<210> SEQ ID NO 50
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 50

Gly Pro Cys Gly Pro Pro Gly Pro Pro Gly Pro Pro Gly Pro Pro Gly
1               5                   10                  15

Pro Pro Gly Ala Arg Gly Pro Glu Gly Ala Gln Gly Pro Arg Gly Glu
            20                  25                  30

Pro Gly Thr Pro Gly Ser Pro Gly Pro Ala Gly Ala Ser Gly Pro Pro
        35                  40                  45

Gly Pro Pro Gly Pro Pro Gly Pro Pro Gly Pro Pro Gly Pro Cys
    50                  55                  60

<210> SEQ ID NO 51
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 51

Gly Pro Cys Gly Pro Pro Gly Pro Pro Gly Pro Pro Gly Pro Pro Gly
1               5                   10                  15

Pro Pro Gly Ser Pro Gly Pro Ala Gly Ala Ser Gly Asn Pro Gly Thr
            20                  25                  30

Asp Gly Ile Pro Gly Ala Lys Gly Ser Ala Gly Ala Pro Gly Pro Pro

```
                      35                  40                  45
Gly Pro Pro Gly Pro Pro Gly Pro Pro Gly Pro Pro Gly Pro Cys
         50                  55                  60

<210> SEQ ID NO 52
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 52

Gly Pro Cys Gly Pro Pro Gly Pro Pro Gly Pro Pro Gly Pro Pro Gly
1               5                  10                  15

Pro Pro Gly Ala Lys Gly Ser Ala Gly Ala Pro Gly Ile Ala Gly Ala
            20                  25                  30

Pro Gly Phe Pro Gly Pro Arg Gly Pro Pro Gly Pro Gln Gly Pro Pro
        35                  40                  45

Gly Pro Pro Gly Pro Pro Gly Pro Pro Gly Pro Pro Gly Pro Cys
         50                  55                  60

<210> SEQ ID NO 53
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 53

Gly Pro Cys Gly Pro Pro Gly Pro Pro Gly Pro Pro Gly Pro Pro Gly
1               5                  10                  15

Pro Pro Gly Pro Arg Gly Pro Pro Gly Pro Gln Gly Ala Thr Gly Pro
            20                  25                  30

Leu Gly Pro Lys Gly Gln Thr Gly Glu Pro Gly Ile Ala Gly Pro Pro
        35                  40                  45

Gly Pro Pro Gly Pro Pro Gly Pro Pro Gly Pro Pro Gly Pro Cys
         50                  55                  60

<210> SEQ ID NO 54
<211> LENGTH: 63
```

```
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 54

Gly Pro Cys Gly Pro Pro Gly Pro Pro Gly Pro Pro Gly Pro Pro Gly
1               5                   10                  15

Pro Pro Gly Gln Thr Gly Glu Pro Gly Ile Ala Gly Phe Lys Gly Glu
            20                  25                  30

Gln Gly Pro Lys Gly Glu Pro Gly Pro Ala Gly Pro Gln Gly Pro Pro
        35                  40                  45

Gly Pro Pro Gly Pro Pro Gly Pro Pro Gly Pro Pro Gly Pro Cys
    50                  55                  60

<210> SEQ ID NO 55
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library
      (collagen II toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 55

Gly Pro Cys Gly Pro Pro Gly Pro Pro Gly Pro Pro Gly Pro Pro Gly
1               5                   10                  15

Pro Pro Gly Glu Pro Gly Pro Ala Gly Pro Gln Gly Ala Pro Gly Pro
            20                  25                  30

Ala Gly Glu Glu Gly Lys Arg Gly Ala Arg Gly Glu Pro Gly Pro Pro
        35                  40                  45

Gly Pro Pro Gly Pro Pro Gly Pro Pro Gly Pro Pro Gly Pro Cys
    50                  55                  60

<210> SEQ ID NO 56
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library
      (collagen II toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
```

```
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 56

Gly Pro Cys Gly Pro Pro Gly Pro Pro Gly Pro Pro Gly Pro Pro Gly
1               5                  10                  15

Pro Pro Gly Lys Arg Gly Ala Arg Gly Glu Pro Gly Val Gly Pro
            20                  25                  30

Ile Gly Pro Pro Gly Glu Arg Gly Ala Pro Gly Asn Arg Gly Pro Pro
        35                  40                  45

Gly Pro Pro Gly Pro Pro Gly Pro Pro Gly Pro Pro Gly Pro Cys
    50                  55                  60

<210> SEQ ID NO 57
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 57

Gly Pro Cys Gly Pro Pro Gly Pro Pro Gly Pro Pro Gly Pro Pro Gly
1               5                  10                  15

Pro Pro Gly Glu Arg Gly Ala Pro Gly Asn Arg Gly Phe Pro Gly Gln
            20                  25                  30

Asp Gly Leu Ala Gly Pro Lys Gly Ala Pro Gly Glu Arg Gly Pro Pro
        35                  40                  45

Gly Pro Pro Gly Pro Pro Gly Pro Pro Gly Pro Pro Gly Pro Cys
    50                  55                  60

<210> SEQ ID NO 58
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 58
```

```
Gly Pro Cys Gly Pro Pro Gly Pro Pro Gly Pro Pro Gly
1               5                   10                  15

Pro Pro Gly Pro Lys Gly Ala Pro Gly Glu Arg Gly Pro Ser Gly Leu
            20                  25                  30

Ala Gly Pro Lys Gly Ala Asn Gly Asp Pro Gly Arg Pro Gly Pro Pro
        35                  40                  45

Gly Pro Pro Gly Pro Pro Gly Pro Pro Gly Pro Cys
    50                  55                  60
```

<210> SEQ ID NO 59
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 59

```
Gly Pro Cys Gly Pro Pro Gly Pro Pro Gly Pro Pro Gly
1               5                   10                  15

Pro Pro Gly Ala Asn Gly Asp Pro Gly Arg Pro Gly Glu Pro Gly Leu
            20                  25                  30

Pro Gly Ala Arg Gly Leu Thr Gly Arg Pro Gly Asp Ala Gly Pro Pro
        35                  40                  45

Gly Pro Pro Gly Pro Pro Gly Pro Pro Gly Pro Cys
    50                  55                  60
```

<210> SEQ ID NO 60
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 60

```
Gly Pro Cys Gly Pro Pro Gly Pro Pro Gly Pro Pro Gly
1               5                   10                  15

Pro Pro Gly Leu Thr Gly Arg Pro Gly Asp Ala Gly Pro Gln Gly Lys
            20                  25                  30

Val Gly Pro Ser Gly Ala Pro Gly Glu Asp Gly Arg Pro Gly Pro Pro
        35                  40                  45

Gly Pro Pro Gly Pro Pro Gly Pro Pro Gly Pro Cys
    50                  55                  60
```

<210> SEQ ID NO 61
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-II collagen peptide library (collagen II toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 61

```
Gly Pro Cys Gly Pro Pro Gly Pro Pro Gly Pro Pro Gly
1               5                   10                  15

Pro Pro Gly Ala Pro Gly Glu Asp Gly Arg Pro Gly Pro Gly
            20                  25                  30

Gln Gly Ala Arg Gly Gln Pro Gly Val Met Gly Phe Pro Gly Pro Pro
        35                  40                  45

Gly Pro Pro Gly Pro Pro Gly Pro Pro Gly Pro Cys
    50                  55                  60
```

<210> SEQ ID NO 62
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-II collagen peptide library (collagen II toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES

```
<222> LOCATION: (45)..(45)
<223> OTHER INFORMATION: 4Hyp

<400> SEQUENCE: 62

Gly Pro Cys Gly Pro Pro Gly Pro Pro Gly Pro Pro Gly Pro Pro Gly
1               5                   10                  15

Pro Pro Gly Gln Pro Gly Val Met Gly Phe Pro Gly Pro Lys Gly Ala
            20                  25                  30

Asn Gly Glu Pro Gly Lys Ala Gly Glu Lys Gly Leu Pro Gly Pro Pro
        35                  40                  45

Gly Pro Pro Gly Pro Pro Gly Pro Pro Gly Pro Pro Gly Pro Cys
    50                  55                  60

<210> SEQ ID NO 63
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 63

Gly Pro Cys Gly Pro Pro Gly Pro Pro Gly Pro Pro Gly Pro Pro Gly
1               5                   10                  15

Pro Pro Gly Lys Ala Gly Glu Lys Gly Leu Pro Gly Ala Pro Gly Leu
            20                  25                  30

Arg Gly Leu Pro Gly Lys Asp Gly Glu Thr Gly Ala Ala Gly Pro Pro
        35                  40                  45

Gly Pro Pro Gly Pro Pro Gly Pro Pro Gly Pro Pro Gly Pro Cys
    50                  55                  60

<210> SEQ ID NO 64
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 64

Gly Pro Cys Gly Pro Pro Gly Pro Pro Gly Pro Pro Gly Pro Pro Gly
1               5                   10                  15

Pro Pro Gly Lys Asp Gly Glu Thr Gly Ala Ala Gly Pro Pro Gly Pro
            20                  25                  30

Ala Gly Pro Ala Gly Glu Arg Gly Glu Gln Gly Ala Pro Gly Pro Pro
```

```
                35                  40                  45
Gly Pro Pro Gly Pro Pro Gly Pro Pro Gly Pro Pro Gly Pro Cys
    50                  55                  60

<210> SEQ ID NO 65
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 65

Gly Pro Cys Gly Pro Pro Gly Pro Pro Gly Pro Pro Gly Pro Pro Gly
1               5                   10                  15

Pro Pro Gly Glu Arg Gly Glu Gln Gly Ala Pro Gly Pro Ser Gly Phe
            20                  25                  30

Gln Gly Leu Pro Gly Pro Pro Gly Pro Pro Gly Glu Gly Gly Pro Pro
        35                  40                  45

Gly Pro Pro Gly Pro Pro Gly Pro Pro Gly Pro Pro Gly Pro Cys
    50                  55                  60

<210> SEQ ID NO 66
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 66

Gly Pro Cys Gly Pro Pro Gly Pro Pro Gly Pro Pro Gly Pro Pro Gly
1               5                   10                  15
```

```
Pro Pro Gly Pro Pro Gly Pro Pro Gly Glu Gly Gly Lys Pro Gly Asp
            20                  25                  30

Gln Gly Val Pro Gly Glu Ala Gly Ala Pro Gly Leu Val Gly Pro Pro
        35                  40                  45

Gly Pro Pro Gly Pro Pro Gly Pro Pro Gly Pro Pro Gly Pro Cys
    50                  55                  60
```

<210> SEQ ID NO 67
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 67

```
Gly Pro Cys Gly Pro Pro Gly Pro Pro Gly Pro Pro Gly Pro Pro Gly
1               5                   10                  15

Pro Pro Gly Glu Ala Gly Ala Pro Gly Leu Val Gly Pro Arg Gly Glu
            20                  25                  30

Arg Gly Phe Pro Gly Glu Arg Gly Ser Pro Gly Ala Gln Gly Pro Pro
        35                  40                  45

Gly Pro Pro Gly Pro Pro Gly Pro Pro Gly Pro Pro Gly Pro Cys
    50                  55                  60
```

<210> SEQ ID NO 68
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 68

```
Gly Pro Cys Gly Pro Pro Gly Pro Pro Gly Pro Pro Gly Pro Pro Gly
1               5                   10                  15

Pro Pro Gly Glu Arg Gly Ser Pro Gly Ala Gln Gly Leu Gln Gly Pro
            20                  25                  30

Arg Gly Leu Pro Gly Thr Pro Gly Thr Asp Gly Pro Lys Gly Pro Pro
        35                  40                  45

Gly Pro Pro Gly Pro Pro Gly Pro Pro Gly Pro Pro Gly Pro Cys
    50                  55                  60
```

```
<210> SEQ ID NO 69
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 69

Gly Pro Cys Gly Pro Pro Gly Pro Pro Gly Pro Pro Gly Pro Pro Gly
1               5                   10                  15

Pro Pro Gly Thr Pro Gly Thr Asp Gly Pro Lys Gly Ala Ser Gly Pro
            20                  25                  30

Ala Gly Pro Pro Gly Ala Gln Gly Pro Pro Gly Leu Gln Gly Pro Pro
        35                  40                  45

Gly Pro Pro Gly Pro Pro Gly Pro Pro Gly Pro Pro Gly Pro Cys
    50                  55                  60

<210> SEQ ID NO 70
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 70

Gly Pro Cys Gly Pro Pro Gly Pro Pro Gly Pro Pro Gly Pro Pro Gly
1               5                   10                  15

Pro Pro Gly Ala Gln Gly Pro Pro Gly Leu Gln Gly Met Pro Gly Glu
            20                  25                  30

Arg Gly Ala Ala Gly Ile Ala Gly Pro Lys Gly Asp Arg Gly Pro Pro
        35                  40                  45

Gly Pro Pro Gly Pro Pro Gly Pro Pro Gly Pro Pro Gly Pro Cys
    50                  55                  60

<210> SEQ ID NO 71
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
```

```
<222> LOCATION: (39)..(39)
<223> OTHER INFORMATION: 4Hyp

<400> SEQUENCE: 71

Gly Pro Cys Gly Pro Pro Gly Pro Pro Gly Pro Pro Gly Pro Pro Gly
1               5                   10                  15

Pro Pro Gly Ile Ala Gly Pro Lys Gly Asp Arg Gly Asp Val Gly Glu
            20                  25                  30

Lys Gly Pro Glu Gly Ala Pro Gly Lys Asp Gly Arg Gly Pro Pro
        35                  40                  45

Gly Pro Pro Gly Pro Pro Gly Pro Pro Gly Pro Pro Gly Pro Cys
    50                  55                  60

<210> SEQ ID NO 72
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 72

Gly Pro Cys Gly Pro Pro Gly Pro Pro Gly Pro Pro Gly Pro Pro Gly
1               5                   10                  15

Pro Pro Gly Ala Pro Gly Lys Asp Gly Gly Arg Gly Leu Thr Gly Pro
            20                  25                  30

Ile Gly Pro Pro Gly Pro Ala Gly Ala Asn Gly Glu Lys Gly Pro Pro
        35                  40                  45

Gly Pro Pro Gly Pro Pro Gly Pro Pro Gly Pro Pro Gly Pro Cys
    50                  55                  60

<210> SEQ ID NO 73
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 73

Gly Pro Cys Gly Pro Pro Gly Pro Pro Gly Pro Pro Gly Pro Pro Gly
1               5                   10                  15

Pro Pro Gly Pro Ala Gly Ala Asn Gly Glu Lys Gly Glu Val Gly Pro
            20                  25                  30

Pro Gly Pro Ala Gly Ser Ala Gly Ala Arg Gly Ala Pro Gly Pro Pro
        35                  40                  45

Gly Pro Pro Gly Pro Pro Gly Pro Pro Gly Pro Pro Gly Pro Cys
    50                  55                  60
```

```
<210> SEQ ID NO 74
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 74

Gly Pro Cys Gly Pro Pro Gly Pro Pro Gly Pro Pro Gly Pro Pro Gly
1               5                   10                  15

Pro Pro Gly Ser Ala Gly Ala Arg Gly Ala Pro Gly Glu Arg Gly Glu
            20                  25                  30

Thr Gly Pro Pro Gly Pro Ala Gly Phe Ala Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 75
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp

<400> SEQUENCE: 75

Gly Pro Cys Gly Pro Pro Gly Pro Pro Gly Pro Pro Gly Pro Pro Gly
1               5                   10                  15

Pro Pro Gly Pro Ala Gly Phe Ala Gly Pro Pro Gly Ala Asp Gly Gln
            20                  25                  30

Pro Gly Ala Lys Gly Glu Gln Gly Glu Ala Gly Gln Lys Gly Pro Pro
        35                  40                  45

Gly Pro Pro Gly Pro Pro Gly Pro Pro Gly Pro Pro Gly Pro Cys
    50                  55                  60

<210> SEQ ID NO 76
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
```

```
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 76

Gly Pro Cys Gly Pro Pro Gly Pro Pro Gly Pro Pro Gly Pro Pro Gly
1               5                   10                  15

Pro Pro Gly Glu Gln Gly Glu Ala Gly Gln Lys Gly Asp Ala Gly Ala
            20                  25                  30

Pro Gly Pro Gln Gly Pro Ser Gly Ala Pro Gly Pro Gln Gly Pro Pro
        35                  40                  45

Gly Pro Pro Gly Pro Pro Gly Pro Pro Gly Pro Pro Gly Pro Cys
    50                  55                  60

<210> SEQ ID NO 77
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 77

Gly Pro Cys Gly Pro Pro Gly Pro Pro Gly Pro Pro Gly Pro Pro Gly
1               5                   10                  15

Pro Pro Gly Glu Gln Gly Glu Ala Gly Gln Lys Gly Glu Ala Gly Ala
            20                  25                  30

Pro Gly Pro Gln Gly Pro Ser Gly Ala Pro Gly Pro Gln Gly Pro Pro
        35                  40                  45

Gly Pro Pro Gly Pro Pro Gly Pro Pro Gly Pro Pro Gly Pro Cys
    50                  55                  60

<210> SEQ ID NO 78
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 78

Gly Pro Cys Gly Pro Pro Gly Pro Pro Gly Pro Pro Gly Pro Pro Gly
1               5                   10                  15

Pro Pro Gly Pro Ser Gly Ala Pro Gly Pro Gln Gly Pro Thr Gly Val
            20                  25                  30

Thr Gly Pro Lys Gly Ala Arg Gly Ala Gln Gly Pro Pro Gly Pro Pro
```

```
                35            40            45
Gly Pro Pro Gly Pro Pro Gly Pro Pro Gly Pro Cys
    50              55              60

<210> SEQ ID NO 79
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 79

Gly Pro Cys Gly Pro Pro Gly Pro Pro Gly Pro Pro Gly
1               5                   10              15

Pro Pro Gly Ala Arg Gly Ala Gln Gly Pro Pro Gly Ala Thr Gly Phe
            20                  25                  30

Pro Gly Ala Ala Gly Arg Val Gly Pro Pro Gly Ser Asn Gly Pro Pro
            35                  40                  45

Gly Pro Pro Gly Pro Pro Gly Pro Pro Gly Pro Cys
    50              55              60

<210> SEQ ID NO 80
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 80

Gly Pro Cys Gly Pro Pro Gly Pro Pro Gly Pro Pro Gly
1               5                   10              15

Pro Pro Gly Arg Val Gly Pro Pro Gly Ser Asn Gly Asn Pro Gly Pro
            20                  25                  30

Pro Gly Pro Pro Gly Pro Ser Gly Lys Asp Gly Pro Lys Gly Pro Pro
            35                  40                  45

Gly Pro Pro Gly Pro Pro Gly Pro Pro Gly Pro Pro Gly Pro Cys
    50              55              60
```

```
<210> SEQ ID NO 81
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 81

Gly Pro Cys Gly Pro Pro Gly Pro Pro Gly Pro Pro Gly Pro Pro Gly
1               5                   10                  15

Pro Pro Gly Pro Ser Gly Lys Asp Gly Pro Lys Gly Ala Arg Gly Asp
            20                  25                  30

Ser Gly Pro Pro Gly Arg Ala Gly Glu Pro Gly Leu Gln Gly Pro Pro
        35                  40                  45

Gly Pro Pro Gly Pro Pro Gly Pro Pro Gly Pro Pro Gly Pro Cys
    50                  55                  60

<210> SEQ ID NO 82
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 82

Gly Pro Cys Gly Pro Pro Gly Pro Pro Gly Pro Pro Gly Pro Pro Gly
1               5                   10                  15

Pro Pro Gly Arg Ala Gly Glu Pro Gly Leu Gln Gly Pro Ala Gly Pro
            20                  25                  30

Pro Gly Glu Lys Gly Glu Pro Gly Asp Asp Gly Pro Ser Gly Pro Pro
        35                  40                  45

Gly Pro Pro Gly Pro Pro Gly Pro Pro Gly Pro Pro Gly Pro Cys
    50                  55                  60

<210> SEQ ID NO 83
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
```

```
<222> LOCATION: (21)..(21)
<223> OTHER INFORMATION: 4Hyp
<220> FEATURE:
<221> NAME/KEY: MOD_RES
<222> LOCATION: (33)..(33)
<223> OTHER INFORMATION: 4Hyp

<400> SEQUENCE: 83

Gly Pro Cys Gly Pro Pro Gly Pro Pro Gly Pro Pro Gly Pro Pro Gly
1               5                   10                  15

Pro Pro Gly Glu Pro Gly Asp Asp Gly Pro Ser Gly Ala Glu Gly Pro
            20                  25                  30

Pro Gly Pro Gln Gly Leu Ala Gly Gln Arg Gly Ile Val Gly Pro Pro
        35                  40                  45

Gly Pro Pro Gly Pro Pro Gly Pro Pro Gly Pro Pro Gly Pro Cys
    50                  55                  60

<210> SEQ ID NO 84
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 84

Gly Pro Cys Gly Pro Pro Gly Pro Pro Gly Pro Pro Gly Pro Pro Gly
1               5                   10                  15

Pro Pro Gly Leu Ala Gly Gln Arg Gly Ile Val Gly Leu Pro Gly Gln
            20                  25                  30

Arg Gly Glu Arg Gly Phe Pro Gly Leu Pro Gly Pro Ser Gly Pro Pro
        35                  40                  45

Gly Pro Pro Gly Pro Pro Gly Pro Pro Gly Pro Pro Gly Pro Cys
    50                  55                  60

<210> SEQ ID NO 85
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
```

```
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 85

Gly Pro Cys Gly Pro Pro Gly Pro Pro Gly Pro Pro Gly Pro Pro Gly
1               5                   10                  15

Pro Pro Gly Phe Pro Gly Leu Pro Gly Pro Ser Gly Glu Pro Gly Lys
            20                  25                  30

Gln Gly Ala Pro Gly Ala Ser Gly Asp Arg Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 86
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 86

Gly Pro Cys Gly Pro Pro Gly Pro Pro Gly Pro Pro Gly Pro Pro Gly
1               5                   10                  15

Pro Pro Gly Ala Ser Gly Asp Arg Gly Pro Pro Gly Pro Val Gly Pro
            20                  25                  30

Pro Gly Leu Thr Gly Pro Ala Gly Glu Pro Gly Arg Glu Gly Pro Pro
        35                  40                  45

Gly Pro Pro Gly Pro Pro Gly Pro Pro Gly Pro Pro Gly Pro Cys
    50                  55                  60

<210> SEQ ID NO 87
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 87
```

```
Gly Pro Cys Gly Pro Pro Gly Pro Pro Gly Pro Pro Gly
1               5                   10                  15

Pro Pro Gly Pro Ala Gly Glu Pro Gly Arg Glu Gly Ser Pro Gly Ala
            20                  25                  30

Asp Gly Pro Pro Gly Arg Asp Gly Ala Ala Gly Val Lys Gly Pro Pro
                35                  40                  45

Gly Pro Pro Gly Pro Pro Gly Pro Pro Gly Pro Pro Gly Pro Cys
    50                  55                  60
```

<210> SEQ ID NO 88
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 88

```
Gly Pro Cys Gly Pro Pro Gly Pro Pro Gly Pro Pro Gly
1               5                   10                  15

Pro Pro Gly Arg Asp Gly Ala Ala Gly Val Lys Gly Asp Arg Gly Glu
            20                  25                  30

Thr Gly Ala Val Gly Ala Pro Gly Ala Pro Gly Pro Pro Gly Pro Pro
                35                  40                  45

Gly Pro Pro Gly Pro Pro Gly Pro Pro Gly Pro Pro Gly Pro Cys
    50                  55                  60
```

<210> SEQ ID NO 89
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 89

```
Gly Pro Cys Gly Pro Pro Gly Pro Pro Gly Pro Pro Gly
1               5                   10                  15
```

```
Pro Pro Gly Ala Pro Gly Ala Pro Gly Pro Pro Gly Ser Pro Gly Pro
            20                  25                  30

Ala Gly Pro Thr Gly Lys Gln Gly Asp Arg Gly Glu Ala Gly Pro Pro
            35                  40                  45

Gly Pro Pro Gly Pro Pro Gly Pro Pro Gly Pro Pro Gly Pro Cys
            50                  55                  60
```

<210> SEQ ID NO 90
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)

<400> SEQUENCE: 90

```
Gly Pro Cys Gly Pro Pro Gly Pro Pro Gly Pro Pro Gly Pro Pro Gly
1               5                   10                  15

Pro Pro Gly Lys Gln Gly Asp Arg Gly Glu Ala Gly Ala Gln Gly Pro
            20                  25                  30

Met Gly Pro Ser Gly Pro Ala Gly Ala Arg Gly Ile Gln Gly Pro Pro
            35                  40                  45

Gly Pro Pro Gly Pro Pro Gly Pro Pro Gly Pro Pro Gly Pro Cys
            50                  55                  60
```

<210> SEQ ID NO 91
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (42)..(42)
<223> OTHER INFORMATION: 4Hyp

<400> SEQUENCE: 91

```
Gly Pro Cys Gly Pro Pro Gly Pro Pro Gly Pro Pro Gly Pro Pro Gly
1               5                   10                  15

Pro Pro Gly Pro Ala Gly Ala Arg Gly Ile Gln Gly Pro Gln Gly Pro
            20                  25                  30

Arg Gly Asp Lys Gly Glu Ala Gly Glu Pro Gly Glu Arg Gly Pro Pro
            35                  40                  45

Gly Pro Pro Gly Pro Pro Gly Pro Pro Gly Pro Pro Gly Pro Cys
            50                  55                  60
```

<210> SEQ ID NO 92
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 92

Gly Pro Cys Gly Pro Pro Gly Pro Pro Gly Pro Pro Gly Pro Pro Gly
1               5                   10                  15

Pro Pro Gly Glu Ala Gly Glu Pro Gly Glu Arg Gly Leu Lys Gly His
            20                  25                  30

Arg Gly Phe Thr Gly Leu Gln Gly Leu Pro Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 93
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 93

Gly Pro Cys Gly Pro Pro Gly Pro Pro Gly Pro Pro Gly Pro Pro Gly
1               5                   10                  15

Pro Pro Gly Leu Gln Gly Leu Pro Gly Pro Pro Gly Pro Ser Gly Asp
            20                  25                  30

Gln Gly Ala Ser Gly Pro Ala Gly Pro Ser Gly Pro Arg Gly Pro Pro
        35                  40                  45

Gly Pro Pro Gly Pro Pro Gly Pro Pro Gly Pro Pro Gly Pro Cys
    50                  55                  60

<210> SEQ ID NO 94
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 94

Gly Pro Cys Gly Pro Pro Gly Pro Pro Gly Pro Pro Gly Pro Pro Gly
1               5                   10                  15

Pro Pro Gly Pro Ala Gly Pro Ser Gly Pro Arg Gly Pro Pro Gly Pro
            20                  25                  30

Val Gly Pro Ser Gly Lys Asp Gly Ala Asn Gly Ile Pro Gly Pro Pro
        35                  40                  45

Gly Pro Pro Gly Pro Pro Gly Pro Pro Gly Pro Pro Gly Pro Cys
    50                  55                  60

```
<210> SEQ ID NO 95
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp

<400> SEQUENCE: 95

Gly Pro Cys Gly Pro Pro Gly Pro Pro Gly Pro Pro Gly Pro Pro Gly
1               5                   10                  15

Pro Pro Gly Lys Asp Gly Ala Asn Gly Ile Pro Gly Pro Ile Gly Pro
            20                  25                  30

Pro Gly Pro Arg Gly Arg Ser Gly Glu Thr Gly Pro Ala Gly Pro Pro
        35                  40                  45

Gly Pro Pro Gly Pro Pro Gly Pro Pro Gly Pro Pro Gly Pro Cys
    50                  55                  60

<210> SEQ ID NO 96
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-II collagen peptide library (collagen II
      toolkit)
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 96

Gly Pro Cys Gly Pro Pro Gly Pro Pro Gly Pro Pro Gly Pro Pro Gly
1               5                   10                  15

Pro Pro Gly Pro Arg Gly Arg Ser Gly Glu Thr Gly Pro Ala Gly Pro
            20                  25                  30

Pro Gly Asn Pro Gly Pro Pro Gly Pro Pro Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 97
<211> LENGTH: 63
```

```
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 97

Gly Pro Cys Gly Pro Pro Gly Pro Pro Gly Pro Pro Gly Pro Pro Gly
1               5                   10                  15

Pro Pro Gly Leu Ala Gly Tyr Pro Gly Pro Ala Gly Pro Pro Gly Pro
                20                  25                  30

Pro Gly Pro Pro Gly Thr Ser Gly His Pro Gly Ser Pro Gly Pro Pro
            35                  40                  45

Gly Pro Pro Gly Pro Pro Gly Pro Pro Gly Pro Pro Gly Pro Cys
        50                  55                  60

<210> SEQ ID NO 98
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 98

Gly Pro Cys Gly Pro Pro Gly Pro Pro Gly Pro Pro Gly Pro Pro Gly
1               5                   10                  15
```

```
Pro Pro Gly Thr Ser Gly His Pro Gly Ser Pro Gly Ser Pro Gly Tyr
        20                  25                  30

Gln Gly Pro Pro Gly Glu Pro Gly Gln Ala Gly Pro Ser Gly Pro Pro
        35                  40                  45

Gly Pro Pro Gly Pro Pro Gly Pro Pro Gly Pro Pro Gly Pro Pro Cys
        50                  55                  60
```

<210> SEQ ID NO 99
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp

<400> SEQUENCE: 99

```
Gly Pro Cys Gly Pro Pro Gly Pro Pro Gly Pro Pro Gly Pro Pro Gly
1               5                   10                  15

Pro Pro Gly Glu Pro Gly Gln Ala Gly Pro Ser Gly Pro Pro Gly Pro
        20                  25                  30

Pro Gly Ala Ile Gly Pro Ser Gly Pro Ala Gly Lys Asp Gly Pro Pro
        35                  40                  45

Gly Pro Pro Gly Pro Pro Gly Pro Pro Gly Pro Pro Gly Pro Pro Cys
        50                  55                  60
```

<210> SEQ ID NO 100
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 100

```
Gly Pro Cys Gly Pro Pro Gly Pro Pro Gly Pro Pro Gly Pro Pro Gly
1               5                   10                  15

Pro Pro Gly Pro Ser Gly Pro Ala Gly Lys Asp Gly Glu Ser Gly Arg
        20                  25                  30

Pro Gly Arg Pro Gly Glu Arg Gly Leu Pro Gly Pro Pro Gly Pro Pro
```

35                  40                  45
Gly Pro Pro Gly Pro Pro Gly Pro Pro Gly Pro Cys
    50                  55                  60

<210> SEQ ID NO 101
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 101

Gly Pro Cys Gly Pro Pro Gly Pro Pro Gly Pro Pro Gly
1               5                   10                  15

Pro Pro Gly Glu Arg Gly Leu Pro Gly Pro Pro Gly Ile Lys Gly Pro
            20                  25                  30

Ala Gly Ile Pro Gly Phe Pro Gly Met Lys Gly His Arg Gly Pro Pro
        35                  40                  45

Gly Pro Pro Gly Pro Pro Gly Pro Pro Gly Pro Pro Gly Pro Cys
    50                  55                  60

<210> SEQ ID NO 102
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 102

Gly Pro Cys Gly Pro Pro Gly Pro Pro Gly Pro Pro Gly Pro Pro Gly
1               5                   10                  15

Pro Pro Gly Phe Pro Gly Met Lys Gly His Arg Gly Phe Asp Gly Arg
            20                  25                  30

Asn Gly Glu Lys Gly Glu Thr Gly Ala Pro Gly Leu Lys Gly Pro Pro
        35                  40                  45

Gly Pro Pro Gly Pro Pro Gly Pro Pro Gly Pro Pro Gly Pro Cys
    50                  55                  60

<210> SEQ ID NO 103
<211> LENGTH: 63

```
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 103

Gly Pro Cys Gly Pro Pro Gly Pro Pro Gly Pro Pro Gly Pro Pro Gly
1               5                   10                  15

Pro Pro Gly Glu Thr Gly Ala Pro Gly Leu Lys Gly Glu Asn Gly Leu
                20                  25                  30

Pro Gly Glu Asn Gly Ala Pro Gly Pro Met Gly Pro Arg Gly Pro Pro
            35                  40                  45

Gly Pro Pro Gly Pro Pro Gly Pro Pro Gly Pro Pro Gly Pro Cys
        50                  55                  60

<210> SEQ ID NO 104
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 104

Gly Pro Cys Gly Pro Pro Gly Pro Pro Gly Pro Pro Gly Pro Pro Gly
1               5                   10                  15

Pro Pro Gly Ala Pro Gly Pro Met Gly Pro Arg Gly Ala Pro Gly Glu
                20                  25                  30

Arg Gly Arg Pro Gly Leu Pro Gly Ala Ala Gly Ala Arg Gly Pro Pro
            35                  40                  45

Gly Pro Pro Gly Pro Pro Gly Pro Pro Gly Pro Pro Gly Pro Cys
        50                  55                  60

<210> SEQ ID NO 105
<211> LENGTH: 63
<212> TYPE: PRT
<213> ORGANISM: Artificial sequence
<220> FEATURE:
<223> OTHER INFORMATION: Synthetic sequence: Sequence of the overlapping
```

-continued homotrimeric type-III collagen peptide library (collagen III
toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 105

Gly Pro Cys Gly Pro Pro Gly Pro Pro Gly Pro Pro Gly Pro Pro Gly
1               5                   10                  15

Pro Pro Gly Leu Pro Gly Ala Ala Gly Ala Arg Gly Asn Asp Gly Ala
            20                  25                  30

Arg Gly Ser Asp Gly Gln Pro Gly Pro Pro Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 106
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 106

Gly Pro Cys Gly Pro Pro Gly Pro Pro Gly Pro Pro Gly Pro Pro Gly
1               5                   10                  15

Pro Pro Gly Gln Pro Gly Pro Pro Gly Pro Pro Gly Thr Ala Gly Phe
            20                  25                  30

Pro Gly Ser Pro Gly Ala Lys Gly Glu Val Gly Pro Ala Gly Pro Pro
        35                  40                  45

Gly Pro Pro Gly Pro Pro Gly Pro Pro Gly Pro Pro Gly Pro Cys
    50                  55                  60

<210> SEQ ID NO 107
<211> LENGTH: 63

```
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 107

Gly Pro Cys Gly Pro Pro Gly Pro Pro Gly Pro Pro Gly Pro Pro Gly
1               5                   10                  15

Pro Pro Gly Ala Lys Gly Glu Val Gly Pro Ala Gly Ser Pro Gly Ser
            20                  25                  30

Asn Gly Ala Pro Gly Gln Arg Gly Glu Pro Gly Pro Gln Gly Pro Pro
        35                  40                  45

Gly Pro Pro Gly Pro Pro Gly Pro Pro Gly Pro Pro Gly Pro Cys
    50                  55                  60

<210> SEQ ID NO 108
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 108

Gly Pro Cys Gly Pro Pro Gly Pro Pro Gly Pro Pro Gly Pro Pro Gly
1               5                   10                  15

Pro Pro Gly Gln Arg Gly Glu Pro Gly Pro Gln Gly His Ala Gly Ala
            20                  25                  30

Gln Gly Pro Pro Gly Pro Pro Gly Ile Asn Gly Ser Pro Gly Pro Pro
        35                  40                  45

Gly Pro Pro Gly Pro Pro Gly Pro Pro Gly Pro Pro Gly Pro Cys
    50                  55                  60

<210> SEQ ID NO 109
<211> LENGTH: 63
<212> TYPE: PRT
<213> ORGANISM: Artificial sequence
<220> FEATURE:
<223> OTHER INFORMATION: Synthetic sequence: Sequence of the overlapping
``` homotrimeric type-III collagen peptide library (collagen III
toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 109

Gly Pro Cys Gly Pro Pro Gly Pro Pro Gly Pro Pro Gly Pro Pro Gly
1               5                   10                  15

Pro Pro Gly Pro Pro Gly Ile Asn Gly Ser Pro Gly Gly Lys Gly Glu
                20                  25                  30

Met Gly Pro Ala Gly Ile Pro Gly Ala Pro Gly Leu Met Gly Pro Pro
            35                  40                  45

Gly Pro Pro Gly Pro Pro Gly Pro Pro Gly Pro Pro Gly Pro Cys
        50                  55                  60

<210> SEQ ID NO 110
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 110

Gly Pro Cys Gly Pro Pro Gly Pro Pro Gly Pro Pro Gly Pro Pro Gly
1               5                   10                  15

Pro Pro Gly Ile Pro Gly Ala Pro Gly Leu Met Gly Ala Arg Gly Pro
                20                  25                  30

Pro Gly Pro Ala Gly Ala Asn Gly Ala Pro Gly Leu Arg Gly Pro Pro
            35                  40                  45

Gly Pro Pro Gly Pro Pro Gly Pro Pro Gly Pro Pro Gly Pro Cys
        50                  55                  60

<210> SEQ ID NO 111
<211> LENGTH: 63
<212> TYPE: PRT
<213> ORGANISM: Artificial sequence
<220> FEATURE:
<223> OTHER INFORMATION: Synthetic sequence: Sequence of the overlapping -continued

```
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 111

Gly Pro Cys Gly Pro Pro Gly Pro Pro Gly Pro Pro Gly Pro Pro Gly
1               5                   10                  15

Pro Pro Gly Ala Asn Gly Ala Pro Gly Leu Arg Gly Gly Ala Gly Glu
            20                  25                  30

Pro Gly Lys Asn Gly Ala Lys Gly Glu Pro Gly Pro Arg Gly Pro Pro
        35                  40                  45

Gly Pro Pro Gly Pro Pro Gly Pro Pro Gly Pro Pro Gly Pro Cys
    50                  55                  60

<210> SEQ ID NO 112
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 112

Gly Pro Cys Gly Pro Pro Gly Pro Pro Gly Pro Pro Gly Pro Pro Gly
1               5                   10                  15

Pro Pro Gly Ala Lys Gly Glu Pro Gly Pro Arg Gly Glu Arg Gly Glu
            20                  25                  30

Ala Gly Ile Pro Gly Val Pro Gly Ala Lys Gly Glu Asp Gly Pro Pro
        35                  40                  45

Gly Pro Pro Gly Pro Pro Gly Pro Pro Gly Pro Pro Gly Pro Cys
    50                  55                  60

<210> SEQ ID NO 113
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
```

```
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 113

Gly Pro Cys Gly Pro Pro Gly Pro Pro Gly Pro Pro Gly Pro Pro Gly
1               5                   10                  15

Pro Pro Gly Val Pro Gly Ala Lys Gly Glu Asp Gly Lys Asp Gly Ser
            20                  25                  30

Pro Gly Glu Pro Gly Ala Asn Gly Leu Pro Gly Ala Ala Gly Pro Pro
        35                  40                  45

Gly Pro Pro Gly Pro Pro Gly Pro Pro Gly Pro Pro Gly Pro Cys
    50                  55                  60

<210> SEQ ID NO 114
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 114

Gly Pro Cys Gly Pro Pro Gly Pro Pro Gly Pro Pro Gly Pro Pro Gly
1               5                   10                  15

Pro Pro Gly Ala Asn Gly Leu Pro Gly Ala Ala Gly Glu Arg Gly Ala
            20                  25                  30

Pro Gly Phe Arg Gly Pro Ala Gly Pro Asn Gly Ile Pro Gly Pro Pro
        35                  40                  45

Gly Pro Pro Gly Pro Pro Gly Pro Pro Gly Pro Pro Gly Pro Cys
    50                  55                  60

<210> SEQ ID NO 115
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 115
```

```
Gly Pro Cys Gly Pro Pro Gly Pro Pro Gly Pro Pro Gly
1               5                   10                  15

Pro Pro Gly Pro Ala Gly Pro Asn Gly Ile Pro Gly Glu Lys Gly Pro
                20              25                  30

Ala Gly Glu Arg Gly Ala Pro Gly Pro Ala Gly Pro Arg Gly Pro Pro
            35                  40                  45

Gly Pro Pro Gly Pro Pro Gly Pro Pro Gly Pro Pro Gly Pro Cys
    50                  55                  60
```

<210> SEQ ID NO 116
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 116

```
Gly Pro Cys Gly Pro Pro Gly Pro Pro Gly Pro Pro Gly
1               5                   10                  15

Pro Pro Gly Ala Pro Gly Pro Ala Gly Pro Arg Gly Ala Ala Gly Glu
                20              25                  30

Pro Gly Arg Asp Gly Val Pro Gly Gly Pro Gly Met Arg Gly Pro Pro
            35                  40                  45

Gly Pro Pro Gly Pro Pro Gly Pro Pro Gly Pro Pro Gly Pro Cys
    50                  55                  60
```

<210> SEQ ID NO 117
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES

```
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 117

Gly Pro Cys Gly Pro Pro Gly Pro Pro Gly Pro Pro Gly Pro Pro Gly
1               5                   10                  15

Pro Pro Gly Val Pro Gly Gly Pro Gly Met Arg Gly Met Pro Gly Ser
            20                  25                  30

Pro Gly Gly Pro Gly Ser Asp Gly Lys Pro Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 118
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 118

Gly Pro Cys Gly Pro Pro Gly Pro Pro Gly Pro Pro Gly Pro Pro Gly
1               5                   10                  15

Pro Pro Gly Ser Asp Gly Lys Pro Gly Pro Pro Gly Ser Gln Gly Glu
            20                  25                  30

Ser Gly Arg Pro Gly Pro Pro Gly Pro Ser Gly Pro Arg Gly Pro Pro
        35                  40                  45

Gly Pro Pro Gly Pro Pro Gly Pro Pro Gly Pro Pro Gly Pro Cys
    50                  55                  60

<210> SEQ ID NO 119
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
```

```
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 119

Gly Pro Cys Gly Pro Pro Gly Pro Pro Gly Pro Pro Gly Pro Pro Gly
1               5                   10                  15

Pro Pro Gly Pro Pro Gly Pro Ser Gly Pro Arg Gly Gln Pro Gly Val
            20                  25                  30

Met Gly Phe Pro Gly Pro Lys Gly Asn Asp Gly Ala Pro Gly Pro Pro
        35                  40                  45

Gly Pro Pro Gly Pro Pro Gly Pro Pro Gly Pro Pro Gly Pro Cys
    50                  55                  60

<210> SEQ ID NO 120
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 120

Gly Pro Cys Gly Pro Pro Gly Pro Pro Gly Pro Pro Gly Pro Pro Gly
1               5                   10                  15

Pro Pro Gly Pro Lys Gly Asn Asp Gly Ala Pro Gly Lys Asn Gly Glu
            20                  25                  30

Arg Gly Gly Pro Gly Gly Pro Gly Pro Gln Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 121
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
```

<222> LOCATION: (27)..(27)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 121

Gly Pro Cys Gly Pro Pro Gly Pro Pro Gly Pro Pro Gly Pro Pro Gly
1               5                   10                  15

Pro Pro Gly Gly Pro Gly Pro Gln Gly Pro Pro Gly Lys Asn Gly Glu
            20                  25                  30

Thr Gly Pro Gln Gly Pro Pro Gly Pro Thr Gly Pro Gly Pro Pro
        35                  40                  45

Gly Pro Pro Gly Pro Pro Gly Pro Pro Gly Pro Pro Gly Pro Cys
    50                  55                  60

<210> SEQ ID NO 122
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 122

Gly Pro Cys Gly Pro Pro Gly Pro Pro Gly Pro Pro Gly Pro Pro Gly
1               5                   10                  15

Pro Pro Gly Pro Pro Gly Pro Thr Gly Pro Gly Gly Asp Lys Gly Asp
            20                  25                  30

Thr Gly Pro Pro Gly Pro Gln Gly Leu Gln Gly Leu Pro Gly Pro Pro
        35                  40                  45

Gly Pro Pro Gly Pro Pro Gly Pro Pro Gly Pro Pro Gly Pro Cys
    50                  55                  60

<210> SEQ ID NO 123
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES

```
<222> LOCATION: (42)..(42)
<223> OTHER INFORMATION: 4Hyp

<400> SEQUENCE: 123

Gly Pro Cys Gly Pro Pro Gly Pro Pro Gly Pro Pro Gly
1               5                   10                  15

Pro Pro Gly Pro Gln Gly Leu Gln Gly Leu Pro Gly Thr Gly Pro
            20                  25                  30

Pro Gly Glu Asn Gly Lys Pro Gly Glu Pro Gly Pro Lys Gly Pro Pro
            35                  40                  45

Gly Pro Pro Gly Pro Pro Gly Pro Pro Gly Pro Pro Gly Pro Cys
        50                  55                  60

<210> SEQ ID NO 124
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 124

Gly Pro Cys Gly Pro Pro Gly Pro Pro Gly Pro Gly Pro Gly
1               5                   10                  15

Pro Pro Gly Lys Pro Gly Glu Pro Gly Pro Lys Gly Asp Ala Gly Ala
            20                  25                  30

Pro Gly Ala Pro Gly Gly Lys Gly Asp Ala Gly Ala Pro Gly Pro Pro
            35                  40                  45

Gly Pro Pro Gly Pro Pro Gly Pro Pro Gly Pro Pro Gly Pro Cys
        50                  55                  60

<210> SEQ ID NO 125
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
```

```
<222> LOCATION: (39)..(39)
<223> OTHER INFORMATION: 4Hyp

<400> SEQUENCE: 125

Gly Pro Cys Gly Pro Pro Gly Pro Pro Gly Pro Pro Gly Pro Pro Gly
1               5                   10                  15

Pro Pro Gly Gly Lys Gly Asp Ala Gly Ala Pro Gly Glu Arg Gly Pro
            20                  25                  30

Pro Gly Leu Ala Gly Ala Pro Gly Leu Arg Gly Gly Ala Gly Pro Pro
        35                  40                  45

Gly Pro Pro Gly Pro Pro Gly Pro Pro Gly Pro Pro Gly Pro Cys
    50                  55                  60

<210> SEQ ID NO 126
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 126

Gly Pro Cys Gly Pro Pro Gly Pro Pro Gly Pro Pro Gly Pro Pro Gly
1               5                   10                  15

Pro Pro Gly Ala Pro Gly Leu Arg Gly Gly Ala Gly Pro Pro Gly Pro
            20                  25                  30

Glu Gly Gly Lys Gly Ala Ala Gly Pro Pro Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 127
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
```

```
<222> LOCATION: (39)..(39)
<223> OTHER INFORMATION: 4Hyp

<400> SEQUENCE: 127

Gly Pro Cys Gly Pro Pro Gly Pro Pro Gly Pro Pro Gly Pro Pro Gly
1               5                   10                  15

Pro Pro Gly Ala Ala Gly Pro Pro Gly Pro Pro Gly Ala Ala Gly Thr
                20                  25                  30

Pro Gly Leu Gln Gly Met Pro Gly Glu Arg Gly Leu Gly Pro Pro
        35                  40                  45

Gly Pro Pro Gly Pro Pro Gly Pro Pro Gly Pro Pro Gly Pro Cys
    50                  55                  60

<210> SEQ ID NO 128
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 128

Gly Pro Cys Gly Pro Pro Gly Pro Pro Gly Pro Pro Gly Pro Pro Gly
1               5                   10                  15

Pro Pro Gly Met Pro Gly Glu Arg Gly Gly Leu Gly Ser Pro Gly Pro
                20                  25                  30

Lys Gly Asp Lys Gly Glu Pro Gly Gly Pro Gly Ala Asp Gly Pro Pro
        35                  40                  45

Gly Pro Pro Gly Pro Pro Gly Pro Pro Gly Pro Pro Gly Pro Cys
    50                  55                  60

<210> SEQ ID NO 129
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
```

<222> LOCATION: (45)..(45)
<223> OTHER INFORMATION: 4Hyp

<400> SEQUENCE: 129

Gly Pro Cys Gly Pro Pro Gly Pro Pro Gly Pro Pro Gly Pro Pro Gly
1               5                   10                  15

Pro Pro Gly Glu Pro Gly Pro Gly Ala Asp Gly Val Pro Gly Lys
            20                  25                  30

Asp Gly Pro Arg Gly Pro Thr Gly Pro Ile Gly Pro Pro Gly Pro Pro
            35                  40                  45

Gly Pro Pro Gly Pro Pro Gly Pro Pro Gly Pro Pro Gly Pro Cys
        50                  55                  60

<210> SEQ ID NO 130
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 130

Gly Pro Cys Gly Pro Pro Gly Pro Pro Gly Pro Pro Gly Pro Pro Gly
1               5                   10                  15

Pro Pro Gly Pro Thr Gly Pro Ile Gly Pro Pro Gly Pro Ala Gly Gln
            20                  25                  30

Pro Gly Asp Lys Gly Glu Gly Ala Pro Gly Leu Pro Gly Pro Pro
            35                  40                  45

Gly Pro Pro Gly Pro Pro Gly Pro Pro Gly Pro Pro Gly Pro Cys
        50                  55                  60

<210> SEQ ID NO 131
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 131

Gly Pro Cys Gly Pro Pro Gly Pro Pro Gly Pro Pro Gly
1               5                   10                  15

Pro Pro Gly Glu Gly Gly Ala Pro Gly Leu Pro Gly Ile Ala Gly Pro
            20                  25                  30

Arg Gly Ser Pro Gly Glu Arg Gly Glu Thr Gly Pro Pro Gly Pro Pro
        35                  40                  45

Gly Pro Pro Gly Pro Pro Gly Pro Pro Gly Pro Pro Gly Pro Cys
    50                  55                  60

<210> SEQ ID NO 132
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 132

Gly Pro Cys Gly Pro Pro Gly Pro Pro Gly Pro Pro Gly
1               5                   10                  15

Pro Pro Gly Glu Arg Gly Glu Thr Gly Pro Pro Gly Pro Ala Gly Phe
            20                  25                  30

Pro Gly Ala Pro Gly Gln Asn Gly Glu Pro Gly Gly Lys Gly Pro Pro
        35                  40                  45

Gly Pro Pro Gly Pro Pro Gly Pro Pro Gly Pro Pro Gly Pro Cys
    50                  55                  60

<210> SEQ ID NO 133
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 133

```
Gly Pro Cys Gly Pro Pro Gly Pro Pro Gly Pro Pro Gly
1               5                   10                  15

Pro Pro Gly Gln Asn Gly Glu Pro Gly Lys Gly Glu Arg Gly Ala
            20                  25                  30

Pro Gly Glu Lys Gly Glu Gly Pro Pro Gly Val Ala Gly Pro Pro
        35                  40                  45

Gly Pro Pro Gly Pro Pro Gly Pro Pro Gly Pro Pro Gly Pro Cys
    50                  55                  60
```

<210> SEQ ID NO 134
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 134

```
Gly Pro Cys Gly Pro Pro Gly Pro Pro Gly Pro Pro Gly
1               5                   10                  15

Pro Pro Gly Glu Gly Gly Pro Pro Gly Val Ala Gly Pro Pro Gly Gly
            20                  25                  30

Ser Gly Pro Ala Gly Pro Pro Gly Pro Gln Gly Val Lys Gly Pro Pro
        35                  40                  45

Gly Pro Pro Gly Pro Pro Gly Pro Pro Gly Pro Pro Gly Pro Cys
    50                  55                  60
```

<210> SEQ ID NO 135
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 135

```
Gly Pro Cys Gly Pro Pro Gly Pro Pro Gly Pro Pro Gly
1               5                   10                  15
```

-continued

Pro Pro Gly Pro Pro Gly Pro Gln Gly Val Lys Gly Glu Arg Gly Ser
            20                  25                  30

Pro Gly Gly Pro Gly Ala Ala Gly Phe Pro Gly Ala Arg Gly Pro Pro
            35                  40                  45

Gly Pro Pro Gly Pro Pro Gly Pro Pro Gly Pro Pro Gly Pro Cys
        50                  55                  60

<210> SEQ ID NO 136
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 136

Gly Pro Cys Gly Pro Pro Gly Pro Pro Gly Pro Pro Gly Pro Pro Gly
1               5                   10                  15

Pro Pro Gly Ala Ala Gly Phe Pro Gly Ala Arg Gly Leu Pro Gly Pro
            20                  25                  30

Pro Gly Ser Asn Gly Asn Pro Gly Pro Pro Gly Pro Ser Gly Pro Pro
            35                  40                  45

Gly Pro Pro Gly Pro Pro Gly Pro Pro Gly Pro Pro Gly Pro Cys
        50                  55                  60

<210> SEQ ID NO 137
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES

```
<222> LOCATION: (45)..(45)
<223> OTHER INFORMATION: 4Hyp

<400> SEQUENCE: 137

Gly Pro Cys Gly Pro Pro Gly Pro Pro Gly Pro Pro Gly Pro Pro Gly
1               5                   10                  15

Pro Pro Gly Asn Pro Gly Pro Pro Gly Pro Ser Gly Ser Pro Gly Lys
            20                  25                  30

Asp Gly Pro Pro Gly Pro Ala Gly Asn Thr Gly Ala Pro Gly Pro Pro
            35                  40                  45

Gly Pro Pro Gly Pro Pro Gly Pro Pro Gly Pro Pro Gly Pro Cys
        50                  55                  60

<210> SEQ ID NO 138
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 138

Gly Pro Cys Gly Pro Pro Gly Pro Pro Gly Pro Pro Gly Pro Pro Gly
1               5                   10                  15

Pro Pro Gly Pro Ala Gly Asn Thr Gly Ala Pro Gly Ser Pro Gly Val
            20                  25                  30

Ser Gly Pro Lys Gly Asp Ala Gly Gln Pro Gly Glu Lys Gly Pro Pro
            35                  40                  45

Gly Pro Pro Gly Pro Pro Gly Pro Pro Gly Pro Pro Gly Pro Cys
        50                  55                  60

<210> SEQ ID NO 139
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 139
```

```
Gly Pro Cys Gly Pro Pro Gly Pro Pro Gly Pro Pro Gly
1               5                   10                  15

Pro Pro Gly Asp Ala Gly Gln Pro Gly Glu Lys Gly Ser Pro Gly Ala
            20                  25                  30

Gln Gly Pro Pro Gly Ala Pro Gly Pro Leu Gly Ile Ala Gly Pro Pro
        35                  40                  45

Gly Pro Pro Gly Pro Pro Gly Pro Pro Gly Pro Pro Gly Pro Cys
    50                  55                  60
```

<210> SEQ ID NO 140
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 140

```
Gly Pro Cys Gly Pro Pro Gly Pro Pro Gly Pro Pro Gly
1               5                   10                  15

Pro Pro Gly Ala Pro Gly Pro Leu Gly Ile Ala Gly Ile Thr Gly Ala
            20                  25                  30

Arg Gly Leu Ala Gly Pro Pro Gly Met Pro Gly Pro Arg Gly Pro Pro
        35                  40                  45

Gly Pro Pro Gly Pro Pro Gly Pro Pro Gly Pro Pro Gly Pro Cys
    50                  55                  60
```

<210> SEQ ID NO 141
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 141

```
Gly Pro Cys Gly Pro Pro Gly Pro Pro Gly Pro Pro Gly
1               5                   10                  15
```

```
Pro Pro Gly Pro Pro Gly Met Pro Gly Pro Arg Gly Ser Pro Gly Pro
            20                  25                  30

Gln Gly Val Lys Gly Glu Ser Gly Lys Pro Gly Ala Asn Gly Pro Pro
            35                  40                  45

Gly Pro Pro Gly Pro Pro Gly Pro Pro Gly Pro Pro Gly Pro Cys
            50                  55                  60

<210> SEQ ID NO 142
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 142

Gly Pro Cys Gly Pro Pro Gly Pro Gly Pro Pro Gly Pro Pro Gly
1               5                   10                  15

Pro Pro Gly Glu Ser Gly Lys Pro Gly Ala Asn Gly Leu Ser Gly Glu
            20                  25                  30

Arg Gly Pro Pro Gly Pro Gln Gly Leu Pro Gly Leu Ala Gly Pro Pro
            35                  40                  45

Gly Pro Pro Gly Pro Pro Gly Pro Pro Gly Pro Pro Gly Pro Cys
            50                  55                  60

<210> SEQ ID NO 143
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 143

Gly Pro Cys Gly Pro Pro Gly Pro Gly Pro Pro Gly Pro Pro Gly
1               5                   10                  15

Pro Pro Gly Pro Gln Gly Leu Pro Gly Leu Ala Gly Thr Ala Gly Glu
            20                  25                  30

Pro Gly Arg Asp Gly Asn Pro Gly Ser Asp Gly Leu Pro Gly Pro Pro
```

```
                35                  40                  45
Gly Pro Pro Gly Pro Pro Gly Pro Pro Gly Pro Cys
        50                  55                  60

<210> SEQ ID NO 144
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 144

Gly Pro Cys Gly Pro Pro Gly Pro Pro Gly Pro Pro Gly Pro Pro Gly
1               5                   10                  15

Pro Pro Gly Asn Pro Gly Ser Asp Gly Leu Pro Gly Arg Asp Gly Ser
            20                  25                  30

Pro Gly Gly Lys Gly Asp Arg Gly Glu Asn Gly Ser Pro Gly Pro Pro
        35                  40                  45

Gly Pro Pro Gly Pro Pro Gly Pro Pro Gly Pro Cys
        50                  55                  60

<210> SEQ ID NO 145
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp

<400> SEQUENCE: 145

Gly Pro Cys Gly Pro Pro Gly Pro Pro Gly Pro Pro Gly Pro Pro Gly
1               5                   10                  15
```

-continued

```
Pro Pro Gly Asp Arg Gly Glu Asn Gly Ser Pro Gly Ala Pro Gly Ala
            20                  25                  30

Pro Gly His Pro Gly Pro Pro Gly Pro Val Gly Pro Ala Gly Pro Pro
        35                  40                  45

Gly Pro Pro Gly Pro Pro Gly Pro Pro Gly Pro Pro Gly Pro Cys
    50                  55                  60

<210> SEQ ID NO 146
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 146

Gly Pro Cys Gly Pro Pro Gly Pro Gly Pro Pro Gly Pro Pro Gly
1               5                   10                  15

Pro Pro Gly Pro Gly Pro Val Gly Pro Ala Gly Lys Ser Gly Asp
            20                  25                  30

Arg Gly Glu Ser Gly Pro Ala Gly Pro Ala Gly Ala Pro Gly Pro Pro
        35                  40                  45

Gly Pro Pro Gly Pro Pro Gly Pro Pro Gly Pro Pro Gly Pro Cys
    50                  55                  60

<210> SEQ ID NO 147
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 147

Gly Pro Cys Gly Pro Pro Gly Pro Pro Gly Pro Pro Gly Pro Pro Gly
1               5                   10                  15

Pro Pro Gly Pro Ala Gly Pro Ala Gly Ala Pro Gly Pro Ala Gly Ser
            20                  25                  30

Arg Gly Ala Pro Gly Pro Gln Gly Pro Arg Gly Asp Lys Gly Pro Pro
        35                  40                  45

Gly Pro Pro Gly Pro Pro Gly Pro Pro Gly Pro Pro Gly Pro Cys
    50                  55                  60

<210> SEQ ID NO 148
<211> LENGTH: 63
<212> TYPE: PRT
<213> ORGANISM: Artificial sequence
<220> FEATURE:
<223> OTHER INFORMATION: Synthetic sequence: Sequence of the overlapping
``` homotrimeric type-III collagen peptide library (collagen III toolkit)
<220> FEATURE:
<221> NAME/KEY: MOD_RES
<222> LOCATION: (45)..(45)
<223> OTHER INFORMATION: 4Hyp

<400> SEQUENCE: 148

Gly Pro Cys Gly Pro Pro Gly Pro Pro Gly Pro Pro Gly Pro Pro Gly
1               5                   10                  15

Pro Pro Gly Pro Gln Gly Pro Arg Gly Asp Lys Gly Glu Thr Gly Glu
            20                  25                  30

Arg Gly Ala Ala Gly Ile Lys Gly His Arg Gly Phe Pro Gly Pro Pro
        35                  40                  45

Gly Pro Pro Gly Pro Pro Gly Pro Pro Gly Pro Pro Gly Pro Cys
    50                  55                  60

<210> SEQ ID NO 149
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 149

Gly Pro Cys Gly Pro Pro Gly Pro Pro Gly Pro Pro Gly Pro Pro Gly
1               5                   10                  15

Pro Pro Gly Ile Lys Gly His Arg Gly Phe Pro Gly Asn Pro Gly Ala
            20                  25                  30

Pro Gly Ser Pro Gly Pro Ala Gly Gln Gln Gly Ala Ile Gly Pro Pro
        35                  40                  45

Gly Pro Pro Gly Pro Pro Gly Pro Pro Gly Pro Pro Gly Pro Cys
    50                  55                  60

<210> SEQ ID NO 150
<211> LENGTH: 63
<212> TYPE: PRT
<213> ORGANISM: Artificial sequence
<220> FEATURE:
<223> OTHER INFORMATION: Synthetic sequence: Sequence of the overlapping homotrimeric type-III collagen peptide library (collagen III toolkit)
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 150

Gly Pro Cys Gly Pro Pro Gly Pro Pro Gly Pro Pro Gly Pro Pro Gly
1               5                   10                  15

Pro Pro Gly Pro Ala Gly Gln Gln Gly Ala Ile Gly Ser Pro Gly Pro
            20                  25                  30

Ala Gly Pro Arg Gly Pro Val Gly Pro Ser Gly Pro Pro Gly Pro Pro
                35                  40                  45

Gly Pro Pro Gly Pro Pro Gly Pro Pro Gly Pro Pro Gly Pro Cys
            50                  55                  60

<210> SEQ ID NO 151
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 151

Gly Pro Cys Gly Pro Pro Gly Pro Pro Gly Pro Pro Gly Pro Pro Gly
1               5                   10                  15

Pro Pro Gly Pro Val Gly Pro Ser Gly Pro Pro Gly Lys Asp Gly Thr
            20                  25                  30

Ser Gly His Pro Gly Pro Ile Gly Pro Pro Gly Pro Arg Gly Pro Pro
                35                  40                  45

Gly Pro Pro Gly Pro Pro Gly Pro Pro Gly Pro Pro Gly Pro Cys
            50                  55                  60

<210> SEQ ID NO 152
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (24)..(24)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp
<220> FEATURE:
<221> NAME/KEY: MOD_RES
<222> LOCATION: (45)..(45)
<223> OTHER INFORMATION: 4Hyp

<400> SEQUENCE: 152

Gly Pro Cys Gly Pro Pro Gly Pro Pro Gly Pro Pro Gly Pro Pro Gly
1               5                   10                  15

```
Pro Pro Gly Pro Ile Gly Pro Pro Gly Pro Arg Gly Asn Arg Gly Glu
            20                  25                  30

Arg Gly Ser Glu Gly Ser Pro Gly His Pro Gly Gln Pro Gly Pro Pro
        35                  40                  45

Gly Pro Pro Gly Pro Pro Gly Pro Pro Gly Pro Pro Gly Pro Cys
    50                  55                  60

<210> SEQ ID NO 153
<211> LENGTH: 63
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp
<220> FEATURE:
<221> NAME/KEY: MOD_RES
<222> LOCATION: (39)..(39)
<223> OTHER INFORMATION: 4Hyp
<220> FEATURE:
<221> NAME/KEY: MOD_RES
<222> LOCATION: (42)..(42)
<223> OTHER INFORMATION: 4Hyp

<400> SEQUENCE: 153

Gly Pro Cys Gly Pro Pro Gly Pro Pro Gly Pro Pro Gly Pro Pro Gly
1               5                   10                  15

Pro Pro Gly Glu Arg Gly Ser Glu Gly Ser Pro Gly His Pro Gly Gln
            20                  25                  30

Pro Gly Pro Pro Gly Pro Pro Gly Ala Pro Gly Pro Cys Gly Pro Pro
        35                  40                  45

Gly Pro Pro Gly Pro Pro Gly Pro Pro Gly Pro Pro Gly Pro Cys
    50                  55                  60

<210> SEQ ID NO 154
<211> LENGTH: 36
<212> TYPE: PRT
<213> ORGANISM: Artificial sequence
<220> FEATURE:
<223> OTHER INFORMATION: Synthetic sequence: Sequence of the overlapping
      homotrimeric type-III collagen peptide library (collagen III
      toolkit)

<400> SEQUENCE: 154

Gly Pro Cys Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Cys
        35

<210> SEQ ID NO 155
```

```
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 155

Gly Pro Cys Gly Pro Pro Gly Pro Pro Gly Pro Pro Gly Pro Pro Gly
 1               5                  10                  15

Pro Pro Gly Ala Pro Gly Pro Ala Gly Glu Ala Gly Pro Pro Gly Pro
            20                  25                  30

Pro Gly Pro Pro Gly Pro Pro Gly Pro Pro Gly Pro Cys
        35                  40                  45

<210> SEQ ID NO 156
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 156

Gly Pro Cys Gly Pro Pro Gly Pro Pro Gly Pro Pro Gly Pro Pro Gly
 1               5                  10                  15

Pro Pro Gly Lys Pro Gly Pro Ala Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 157
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 157

Gly Pro Cys Gly Pro Pro Gly Pro Pro Gly Pro Pro Gly Pro Pro Gly
 1               5                  10                  15

Pro Pro Gly Ala Pro Gly Val Met Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 158
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
```

```
<222> LOCATION: (27)..(27)
<223> OTHER INFORMATION: 4Hyp

<400> SEQUENCE: 158

Gly Pro Cys Gly Pro Pro Gly Pro Pro Gly Pro Pro Gly Pro Pro Gly
1               5                   10                  15

Pro Pro Gly Leu Pro Gly Pro Ser Gly Glu Pro Gly Pro Pro Gly Pro
                20                  25                  30

Pro Gly Pro Pro Gly Pro Pro Gly Pro Pro Gly Pro Cys
            35                  40                  45

<210> SEQ ID NO 159
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 159

Gly Pro Cys Gly Pro Pro Gly Pro Pro Gly Pro Pro Gly Pro Pro Gly
1               5                   10                  15

Pro Pro Gly Phe Pro Gly Leu Pro Gly Pro Ser Gly Pro Pro Gly Pro
                20                  25                  30

Pro Gly Pro Pro Gly Pro Pro Gly Pro Pro Gly Pro Cys
            35                  40                  45

<210> SEQ ID NO 160
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 160

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Ala Gly Glu Ala Gly Pro
                20                  25                  30

Pro Gly Pro Pro Gly Pro Pro Gly Pro Pro Gly Pro Cys
            35                  40                  45

<210> SEQ ID NO 161
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 161

Gly Pro Cys Gly Pro Pro Gly Pro Pro Gly Pro Pro Gly Pro Pro Gly
1               5                   10                  15
```

```
Pro Pro Gly Phe Pro Gly Pro Ala Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 162
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 162

Gly Pro Cys Gly Pro Pro Gly Pro Pro Gly Pro Pro Gly Pro Pro Gly
1               5                   10                  15

Pro Pro Gly Pro Pro Gly Pro Ala Gly Phe Pro Gly Ala Pro Gly Pro
            20                  25                  30

Pro Gly Pro Pro Gly Pro Pro Gly Pro Pro Gly Pro Cys
        35                  40                  45

<210> SEQ ID NO 163
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 163

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Pro Gly Ala Pro Gly Pro
            20                  25                  30

Pro Gly Pro Pro Gly Pro Pro Gly Pro Pro Gly Pro Cys
        35                  40                  45

<210> SEQ ID NO 164
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
```

```
<220> FEATURE:
<221> NAME/KEY: MOD_RES
<222> LOCATION: (30)..(30)
<223> OTHER INFORMATION: 4Hyp

<400> SEQUENCE: 164

Gly Pro Cys Gly Pro Pro Gly Pro Pro Gly Pro Pro Gly Pro Pro Gly
1               5                   10                  15

Pro Pro Gly Pro Pro Gly Pro Ala Gly Phe Ala Gly Ala Pro Gly Pro
                20                  25                  30

Pro Gly Pro Pro Gly Pro Pro Gly Pro Pro Gly Pro Cys
        35                  40                  45

<210> SEQ ID NO 165
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 165

Gly Pro Cys Gly Pro Pro Gly Pro Pro Gly Pro Pro Gly Pro Pro Gly
1               5                   10                  15

Pro Pro Gly Ala Pro Gly Pro Ala Gly Ser Ala Gly Pro Pro Gly Pro
                20                  25                  30

Pro Gly Pro Pro Gly Pro Pro Gly Pro Cys
        35                  40                  45

<210> SEQ ID NO 166
<211> LENGTH: 57
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (33)..(33)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 166

Gly Pro Cys Gly Pro Pro Gly Pro Pro Gly Pro Pro Gly Pro Pro Gly
1               5                   10                  15

Pro Pro Gly Glu Arg Gly Glu Thr Gly Pro Pro Gly Pro Ala Gly Phe
                20                  25                  30

Pro Gly Ala Pro Gly Gln Asn Gly Pro Pro Gly Pro Pro Gly Pro Pro
        35                  40                  45

Gly Pro Pro Gly Pro Pro Gly Pro Cys
    50                  55

<210> SEQ ID NO 167
<211> LENGTH: 57
<212> TYPE: PRT
<213> ORGANISM: Artificial sequence
<220> FEATURE:
<223> OTHER INFORMATION: Synthetic sequence: III-36 peptide derivative
```

-continued

```
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp
<220> FEATURE:
<221> NAME/KEY: MOD_RES
<222> LOCATION: (36)..(36)
<223> OTHER INFORMATION: 4Hyp

<400> SEQUENCE: 167

Gly Pro Cys Gly Pro Pro Gly Pro Pro Gly Pro Pro Gly Pro Pro Gly
1               5                   10                  15

Pro Pro Gly Pro Pro Gly Pro Ala Gly Phe Pro Gly Ala Pro Gly Gln
            20                  25                  30

Asn Gly Glu Pro Gly Gly Lys Gly Pro Pro Gly Pro Pro Gly Pro Pro
        35                  40                  45

Gly Pro Pro Gly Pro Pro Gly Pro Cys
        50                  55

<210> SEQ ID NO 168
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 168

Gly Pro Cys Gly Pro Pro Gly Pro Pro Gly Pro Pro Gly Pro Pro Gly
1               5                   10                  15

Pro Pro Gly Pro Pro Gly Ala Ala Gly Phe Pro Gly Ala Pro Gly Pro
            20                  25                  30

Pro Gly Pro Pro Gly Pro Pro Gly Pro Pro Gly Pro Pro Gly Pro Cys
        35                  40                  45

<210> SEQ ID NO 169
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
```

<223> OTHER INFORMATION: 4Hyp

<400> SEQUENCE: 169

Gly Pro Cys Gly Pro Pro Gly Pro Pro Gly Pro Pro Gly Pro Pro Gly
1               5                   10                  15

Pro Pro Gly Pro Pro Gly Pro Ala Gly Ala Pro Gly Ala Pro Gly Pro
                20                  25                  30

Pro Gly Pro Pro Gly Pro Pro Gly Pro Pro Gly Pro Cys
            35                  40                  45

<210> SEQ ID NO 170
<211> LENGTH: 48
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 170

Gly Pro Cys Gly Pro Pro Gly Pro Pro Gly Pro Pro Gly Pro Pro Gly
1               5                   10                  15

Pro Pro Gly Pro Pro Gly Pro Ala Gly Phe Pro Gly Ala Ala Gly Pro
                20                  25                  30

Pro Gly Pro Pro Gly Pro Pro Gly Pro Pro Gly Pro Cys
            35                  40                  45

<210> SEQ ID NO 171
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 171

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Ala Gly Pro Pro Gly Pro
                20                  25                  30

Pro Gly Pro Pro Gly Pro Pro Gly Pro Cys
            35                  40                  45

<210> SEQ ID NO 172
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 172

Gly Pro Cys Gly Pro Pro Gly Pro Pro Gly Pro Pro Gly Pro Pro Gly
1               5                   10                  15

Pro Pro Gly Ala Pro Gly Ala Ala Gly Phe Ala Gly Pro Pro Gly Pro
            20                  25                  30

Pro Gly Pro Pro Gly Pro Pro Gly Pro Cys
        35                  40                  45

<210> SEQ ID NO 173
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 173

Gly Pro Cys Gly Pro Pro Gly Pro Pro Gly Pro Pro Gly Pro Pro Gly
1               5                   10                  15

Pro Pro Gly Ala Pro Gly Pro Pro Gly Phe Ala Gly Pro Pro Gly Pro
            20                  25                  30

Pro Gly Pro Pro Gly Pro Pro Gly Pro Cys
        35                  40                  45

<210> SEQ ID NO 174
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 174

Gly Pro Cys Gly Pro Pro Gly Pro Pro Gly Pro Pro Gly Pro Pro Gly
1               5                   10                  15

Pro Pro Gly Ala Pro Gly Pro Pro Gly Phe Ala Gly Pro Pro Gly Pro
            20                  25                  30

Pro Gly Pro Pro Gly Pro Pro Gly Pro Cys
        35                  40                  45

<210> SEQ ID NO 175
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 175

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Asp Gly Pro Pro Gly Pro
            20                  25                  30

Pro Gly Pro Pro Gly Pro Pro Gly Pro Cys
        35                  40                  45

```
<210> SEQ ID NO 176
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 176

Gly Pro Cys Gly Pro Pro Gly Pro Pro Gly Pro Pro Gly Pro Pro Gly
1               5                   10                  15

Pro Pro Gly Gln Pro Gly Pro Ala Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 177
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 177

Gly Pro Cys Gly Pro Pro Gly Pro Pro Gly Pro Pro Gly Pro Pro Gly
1               5                   10                  15

Pro Pro Gly Glu Pro Gly Pro Ala Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 178
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 178

Gly Pro Cys Gly Pro Pro Gly Pro Pro Gly Pro Pro Gly Pro Pro Gly
1               5                   10                  15

Pro Pro Gly Ala Pro Gly Pro Gln Gly Phe Ala Gly Pro Pro Gly Pro
            20                  25                  30

Pro Gly Pro Pro Gly Pro Pro Gly Pro Pro Gly Pro Cys
        35                  40                  45

<210> SEQ ID NO 179
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp
```

-continued

```
<400> SEQUENCE: 179

Gly Pro Cys Gly Pro Pro Gly Pro Pro Gly Pro Pro Gly Pro Pro Gly
1               5                   10                  15

Pro Pro Gly Ala Pro Gly Gln Ala Gly Pro Ala Gly Pro Pro Gly Pro
            20                  25                  30

Pro Gly Pro Pro Gly Pro Pro Gly Pro Pro Gly Pro Cys
        35                  40                  45

<210> SEQ ID NO 180
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 180

Gly Pro Cys Gly Pro Pro Gly Pro Pro Gly Pro Pro Gly Pro Pro Gly
1               5                   10                  15

Pro Pro Gly Ala Pro Gly Ala Ser Gly Asp Arg Gly Pro Pro Gly Pro
            20                  25                  30

Pro Gly Pro Pro Gly Pro Pro Gly Pro Pro Gly Pro Cys
        35                  40                  45

<210> SEQ ID NO 181
<211> LENGTH: 45
<212> TYPE: PRT
<213> ORGANISM: Artificial sequence
<220> FEATURE:
<223> OTHER INFORMATION: Synthetic sequence: III-36 peptide derivative
<220> FEATURE:
<221> NAME/KEY: MOD_RES
<222> LOCATION: (21)..(21)
<223> OTHER INFORMATION: 4Hyp

<400> SEQUENCE: 181

Gly Pro Cys Gly Pro Pro Gly Pro Pro Gly Pro Pro Gly Pro Pro Gly
1               5                   10                  15

Pro Pro Gly Ala Pro Gly Pro Ala Gly Tyr Ala Gly Pro Pro Gly Pro
            20                  25                  30

Pro Gly Pro Pro Gly Pro Pro Gly Pro Pro Gly Pro Cys
        35                  40                  45

<210> SEQ ID NO 182
<211> LENGTH: 37
<212> TYPE: PRT
<213> ORGANISM: Artificial sequence
<220> FEATURE:
<223> OTHER INFORMATION: Synthetic sequence: III-36 peptide derivative

<400> SEQUENCE: 182

Gly Pro Cys Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Cys Gly
        35

<210> SEQ ID NO 183
<211> LENGTH: 20
<212> TYPE: DNA
```

```
<213> ORGANISM: Artificial sequence
<220> FEATURE:
<223> OTHER INFORMATION: Synthetic sequence: Primer

<400> SEQUENCE: 183
ttcatcctgg cccacatatg                                              20

<210> SEQ ID NO 184
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 184
tatctgtatg gtcgtggctc                                              20

<210> SEQ ID NO 185
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 185
caagtcgaat ctccagacac                                              20

<210> SEQ ID NO 186
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 186
aggaggtcca gagtgaaaag                                              20

<210> SEQ ID NO 187
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 187
tctggcagct aaggttcttg                                              20

<210> SEQ ID NO 188
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 188
caacgaagcc ttagcaagac                                              20

<210> SEQ ID NO 189
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 189
attccacagc ccaaagtgtg                                              20
```

```
<210> SEQ ID NO 190
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 190
tgaatgcaag gtgaagccag                                               20

<210> SEQ ID NO 191
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 191
gtagacgctg cttgttcatc                                               20

<210> SEQ ID NO 192
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 192
aagggctcat gaccacagtc                                               20

<210> SEQ ID NO 193
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 193
ggcccctcct gttattatgg                                               20

<210> SEQ ID NO 194
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 194
actgctggta acggatcagc                                               20

<210> SEQ ID NO 195
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 195
tccaaggagc cagaaccttc                                               20

<210> SEQ ID NO 196
<211> LENGTH: 273
<212> TYPE: PRT
<213> ORGANISM: Rattus norvegicus

<400> SEQUENCE: 196
```

```
Met Val Leu Leu Leu Ile Leu Gln Leu Ser Thr Cys Glu Leu Ser
1               5                   10                  15

Leu Pro Trp Pro Val Cys His Ala Asp Phe Thr Ser Pro Val Pro Leu
            20                  25                  30

Ala Ser Tyr Pro Lys Pro Trp Leu Gly Ala His Pro Ala Ala Ile Val
            35                  40                  45

Thr Pro Gly Ile Asn Val Thr Leu Ile Cys Arg Ala Pro Gln Pro Ala
            50                  55                  60

Trp Gly Phe Gly Leu Phe Lys Thr Gly Leu Ala Thr Pro Leu Leu Leu
65              70                  75                  80

Arg Asn Val Ser Ile Gly Leu Ala Glu Phe Phe Leu Glu Lys Val Thr
                85                  90                  95

Ser Val Gln Glu Gly Ser Tyr His Cys Arg Tyr Arg Lys Thr Asp Trp
            100                 105                 110

Gly Pro Gly Val Trp Ser Gln Pro Ser Asn Ala Leu Glu Leu Leu Val
            115                 120                 125

Thr Asp Gln Leu Pro Arg Pro Ser Leu Val Ala Ile Pro Gly Pro Val
    130                 135                 140

Val Ala Pro Glu Thr Thr Val Ser Leu Arg Cys Ala Gly Arg Ile Pro
145                 150                 155                 160

Gly Met Ser Phe Ala Leu Tyr Arg Ala Asp Val Ala Thr Pro Leu Gln
                165                 170                 175

Tyr Ile Asp Ser Val Gln Pro Trp Ala Asp Phe Leu Leu Asn Ser Ala
            180                 185                 190

Asn Ala Pro Gly Thr Tyr Tyr Cys Tyr Tyr His Thr Pro Ser Ser Pro
            195                 200                 205

Tyr Val Leu Ser Glu Arg Ser Gln Pro Leu Val Ile Ser Ser Glu Gly
    210                 215                 220

Ser Gly Ser Leu Asp Tyr Thr Gln Gly Asn Leu Val Arg Leu Gly Leu
225                 230                 235                 240

Ala Gly Leu Val Leu Ile Cys Leu Gly Ile Ile Val Thr Phe Asp Trp
                245                 250                 255

His Ser Arg Arg Ser Ala Phe Val Arg Leu Leu Pro Gln Gln Asn Trp
            260                 265                 270

Val

<210> SEQ ID NO 197
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 197

Gly Pro Met Gly Pro Met Gly Pro Arg Gly Pro Pro Gly Pro Ala Gly
1               5                   10                  15

Ala Pro Gly Pro Gln Gly Phe Gln Gly Asn Pro
```

<210> SEQ ID NO 198
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 198

Gly Glu Arg Gly Glu Gln Gly Ala Pro Gly Pro Ser Gly Phe Gln Gly
1               5                   10                  15

Leu Pro Gly Pro Pro Gly Pro Pro Gly Glu Gly
            20                  25

<210> SEQ ID NO 199
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 199

Gly Ser Ala Gly Ala Arg Gly Ala Pro Gly Glu Arg Gly Glu Thr Gly
1               5                   10                  15

Pro Pro Gly Pro Ala Gly Phe Ala Gly Pro Pro
            20                  25

<210> SEQ ID NO 200
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp

```
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (27)..(27)
<223> OTHER INFORMATION: 4Hyp

<400> SEQUENCE: 200

Gly Phe Pro Gly Leu Pro Gly Pro Ser Gly Glu Pro Gly Lys Gln Gly
1               5                   10                  15

Ala Pro Gly Ala Ser Gly Asp Arg Gly Pro Pro
            20                  25

<210> SEQ ID NO 201
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 201

Gly Glu Arg Gly Glu Thr Gly Pro Pro Gly Pro Ala Gly Phe Pro Gly
1               5                   10                  15

Ala Pro Gly Gln Asn Gly Glu Pro Gly Gly Lys
            20                  25

<210> SEQ ID NO 202
<211> LENGTH: 27
<212> TYPE: PRT
<213> ORGANISM: Artificial sequence
<220> FEATURE:
<223> OTHER INFORMATION: Synthetic sequence: Homotrimeric collagen-based
      peptide sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 202
```

```
Gly Pro Pro Gly Pro Gln Gly Val Lys Gly Glu Arg Gly Ser Pro Gly
1               5                   10                  15

Gly Pro Gly Ala Ala Gly Phe Pro Gly Ala Arg
                20                  25

<210> SEQ ID NO 203
<211> LENGTH: 12
<212> TYPE: PRT
<213> ORGANISM: Artificial sequence
<220> FEATURE:
<223> OTHER INFORMATION: Synthetic sequence: Consensus among highest
      affinity Toolkit peptides
<220> FEATURE:
<221> NAME/KEY: VARIANT
<222> LOCATION: (2)..(2)
<223> OTHER INFORMATION: Xaa = no overall consensus
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (6)..(6)
<223> OTHER INFORMATION: Xaa = no overall consensus
<220> FEATURE:
<221> NAME/KEY: MOD_RES
<222> LOCATION: (9)..(9)
<223> OTHER INFORMATION: 4Hyp
<220> FEATURE:
<221> NAME/KEY: VARIANT
<222> LOCATION: (11)..(11)
<223> OTHER INFORMATION: Xaa = no overall consensus
<220> FEATURE:
<221> NAME/KEY: MOD_RES
<222> LOCATION: (12)..(12)
<223> OTHER INFORMATION: 4Hyp

<400> SEQUENCE: 203

Gly Xaa Pro Gly Pro Xaa Gly Phe Pro Gly Xaa Pro
1               5                   10

<210> SEQ ID NO 204
<211> LENGTH: 9
<212> TYPE: PRT
<213> ORGANISM: Artificial sequence
<220> FEATURE:
<223> OTHER INFORMATION: Synthetic sequence: Putative OSCAR binding site
<220> FEATURE:
<221> NAME/KEY: VARIANT
<222> LOCATION: (2)..(2)
<223> OTHER INFORMATION: Xaa = Ala or Pro or Gly
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (5)..(5)
<223> OTHER INFORMATION: Xaa = Pro or Ala
<220> FEATURE:
<221> NAME/KEY: VARIANT
<222> LOCATION: (6)..(6)
<223> OTHER INFORMATION: Xaa = Ala or Ser
<220> FEATURE:
<221> NAME/KEY: VARIANT
<222> LOCATION: (8)..(8)
<223> OTHER INFORMATION: Xaa = Phe, Asp, Ser, or Tyr
<220> FEATURE:
<221> NAME/KEY: VARIANT
<222> LOCATION: (9)..(9)
<223> OTHER INFORMATION: Xaa = Ala, Arg, Hydroxyproline, or Gln

<400> SEQUENCE: 204

Gly Xaa Pro Gly Xaa Xaa Gly Xaa Xaa
```

-continued

```
<210> SEQ ID NO 205
<211> LENGTH: 9
<212> TYPE: PRT
<213> ORGANISM: Artificial sequence
<220> FEATURE:
<223> OTHER INFORMATION: Synthetic sequence: Collagen peptide
<220> FEATURE:
<221> NAME/KEY: VARIANT
<222> LOCATION: (2)..(2)
<223> OTHER INFORMATION: Xaa is independently Ala, Pro or Gly,
      preferably Pro or Ala, more preferably Ala
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (5)..(5)
<223> OTHER INFORMATION: Xaa is independently Pro, Ala, or Val, more
      preferably Pro or Ala
<220> FEATURE:
<221> NAME/KEY: VARIANT
<222> LOCATION: (6)..(6)
<223> OTHER INFORMATION: Xaa is independently Ala, Met, Pro,
      hydroxyproline, Gln, or Ser; more preferably Ala or Ser
<220> FEATURE:
<221> NAME/KEY: VARIANT
<222> LOCATION: (8)..(8)
<223> OTHER INFORMATION: Xaa is independently Phe, Ser, Asp, Tyr, Ala or
      Glu; preferably Phe, Ser, Asp or Tyr, most preferably Phe
<220> FEATURE:
<221> NAME/KEY: VARIANT
<222> LOCATION: (9)..(9)
<223> OTHER INFORMATION: Xaa is independently hydroxyproline, Ala, Arg
      or Gln, preferably hydroxyproline

<400> SEQUENCE: 205

Gly Xaa Pro Gly Xaa Xaa Gly Xaa Xaa
1               5

<210> SEQ ID NO 206
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (2)..(2)
<223> OTHER INFORMATION: Xaa is independently Ala, Pro or Gly,
      preferably Pro or Ala, more preferably Ala
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (6)..(6)
<223> OTHER INFORMATION: Xaa is independently Ala, Met, Pro,
      hydroxyproline, Gln, or Ser; more preferably Ala or Ser
<220> FEATURE:
<221> NAME/KEY: VARIANT
<222> LOCATION: (9)..(9)
<223> OTHER INFORMATION: Xaa is independently hydroxyproline, Ala, Arg
      or Gln, preferably hydroxyproline

<400> SEQUENCE: 206

Gly Xaa Pro Gly Pro Xaa Gly Phe Xaa
1               5

<210> SEQ ID NO 207
<211> LENGTH: 9
<212> TYPE: PRT
```

```
<213> ORGANISM: Artificial sequence
<220> FEATURE:
<223> OTHER INFORMATION: Synthetic sequence
<220> FEATURE:
<221> NAME/KEY: VARIANT
<222> LOCATION: (2)..(2)
<223> OTHER INFORMATION: Xaa is independently Ala, Pro or Gly,
      preferably Pro or Ala, more preferably Ala
<220> FEATURE:
<221> NAME/KEY: MOD_RES
<222> LOCATION: (3)..(3)
<223> OTHER INFORMATION: 4Hyp
<220> FEATURE:
<221> NAME/KEY: VARIANT
<222> LOCATION: (6)..(6)
<223> OTHER INFORMATION: Xaa is independently Ala, Met, Pro,
      hydroxyproline, Gln, or Ser; more preferably Ala or Ser
<220> FEATURE:
<221> NAME/KEY: MOD_RES
<222> LOCATION: (9)..(9)
<223> OTHER INFORMATION: 4Hyp

<400> SEQUENCE: 207

Gly Xaa Pro Gly Pro Xaa Gly Phe Pro
1               5

<210> SEQ ID NO 208
<211> LENGTH: 30
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (1)..(3)
<223> OTHER INFORMATION: Sequence repeat. Any 9 sequence repeats may be
      present or absent - represents the formula (GXaXb)n wherein n is 1
      to 10
<220> FEATURE:
<221> NAME/KEY: VARIANT
<222> LOCATION: (2)..(3)
<223> OTHER INFORMATION: Each Xaa is independently any amino acid except
      glycine
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: VARIANT
<222> LOCATION: (23)..(24)
<223> OTHER INFORMATION: Each Xaa is independently any amino acid except
      glycine
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
```

```
<222> LOCATION: (29)..(30)
<223> OTHER INFORMATION: Xaa can be any naturally occurring amino acid

<400> SEQUENCE: 208

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa
            20                  25                  30

<210> SEQ ID NO 209
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp

<400> SEQUENCE: 209

Gly Pro Pro Gly Pro Pro Gly Pro Pro
1               5

<210> SEQ ID NO 210
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 210

Gly Arg Pro Gly Glu Arg
1               5

<210> SEQ ID NO 211
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 211

Gly Phe Pro Gly Glu Arg Gly Ala Pro
1               5

<210> SEQ ID NO 212
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
```

```
<223> OTHER INFORMATION: 4Hyp

<400> SEQUENCE: 212

Gly Leu Pro Gly Glu Arg
1               5

<210> SEQ ID NO 213
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 213

Gly Phe Pro Gly Asp Arg
1               5

<210> SEQ ID NO 214
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 214

Gly Ala Pro Gly Glu Arg
1               5

<210> SEQ ID NO 215
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
<223> OTHER INFORMATION: Pro = Hydroxyproline

<400> SEQUENCE: 215

Gly Pro Ala Gly Pro Ala Gly Phe Pro Gly Ala Pro
1               5                   10

<210> SEQ ID NO 216
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 216

Gly Lys Pro Gly Pro Ala Gly Phe Ala
1               5
```

```
<210> SEQ ID NO 217
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (9)..(9)
<223> OTHER INFORMATION: 4Hyp

<400> SEQUENCE: 217

Gly Leu Pro Gly Pro Ser Gly Glu Pro
1               5

<210> SEQ ID NO 218
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp

<400> SEQUENCE: 218

Gly Phe Pro Gly Leu Pro Gly Pro Ser
1               5

<210> SEQ ID NO 219
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 219

Gly Phe Pro Gly Pro Ala Gly Phe Ala
1               5

<210> SEQ ID NO 220
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 220

Gly Gln Pro Gly Pro Ala Gly Phe Ala
1               5

<210> SEQ ID NO 221
<211> LENGTH: 9
<212> TYPE: PRT
<213> ORGANISM: Artificial sequence
```

```
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: 4Hyp

<400> SEQUENCE: 221

Gly Glu Pro Gly Pro Ala Gly Phe Ala
1               5

<210> SEQ ID NO 222
<211> LENGTH: 15
<212> TYPE: PRT
<213> ORGANISM: Artificial sequence
<220> FEATURE:
<223> OTHER INFORMATION: Synthetic sequence: Linear peptide containing
      the minimal OSCAR-binding sequence GPOGPAGFO (SEQ ID NO:10)
<220> FEATURE:
<221> NAME/KEY: MOD_RES
<222> LOCATION: (6)..(12)
<223> OTHER INFORMATION: 4Hyp

<400> SEQUENCE: 222

Gly Pro Cys Gly Pro Pro Gly Pro Ala Gly Phe Pro Gly Pro Cys
1               5                   10                  15

<210> SEQ ID NO 223
<211> LENGTH: 45
<212> TYPE: PRT
<213> ORGANISM: Artificial sequence
<220> FEATURE:
<223> OTHER INFORMATION: Synthetic sequence: Triple-helical peptide
      designed to the minimal OSCAR-binding sequence (GPP)5 -
      GPOGPAGFO - (GPP)5 (SEQ ID NO:11)
<220> FEATURE:
<221> NAME/KEY: MOD_RES
<222> LOCATION: (21)..(27)
<223> OTHER INFORMATION: 4Hyp

<400> SEQUENCE: 223

Gly Pro Cys Gly Pro Pro Gly Pro Pro Gly Pro Pro Gly Pro Pro Gly
1               5                   10                  15

Pro Pro Gly Pro Pro Gly Pro Ala Gly Phe Pro Gly Pro Pro Gly Pro
            20                  25                  30

Pro Gly Pro Pro Gly Pro Pro Gly Pro Pro Gly Pro Cys
        35                  40                  45

<210> SEQ ID NO 224
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (27)..(27)
<223> OTHER INFORMATION: 4Hyp
<220> FEATURE:
<221> NAME/KEY: MOD_RES
<222> LOCATION: (30)..(30)
<223> OTHER INFORMATION: 4Hyp

<400> SEQUENCE: 224

Gly Pro Cys Gly Pro Pro Gly Pro Pro Gly Pro Pro Gly Pro Pro Gly
1               5                   10                  15
```

```
Pro Pro Gly Pro Pro Gly Pro Ala Gly Phe Pro Gly Ala Pro Gly Pro
            20              25                  30

Pro Gly Pro Gly Pro Pro Gly Pro Pro Gly Pro Pro Gly Pro Cys
        35              40                  45

<210> SEQ ID NO 225
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (21)..(21)
<223> OTHER INFORMATION: 4Hyp

<400> SEQUENCE: 225

Gly Pro Cys Gly Pro Pro Gly Pro Pro Gly Pro Pro Gly Pro Pro Gly
1               5                   10                  15

Pro Pro Gly Ala Pro Gly Pro Ala Gly Phe Ala Gly Pro Pro Gly Pro
            20                  25                  30

Pro Gly Pro Pro Gly Pro Pro Gly Pro Pro Gly Pro Cys
        35              40                  45
```